United States Patent
Gravestock et al.

(10) Patent No.: US 7,192,974 B2
(45) Date of Patent: Mar. 20, 2007

(54) HYDROXYMETHYL SUBSTITUTED DIHYDROISOXAZOLE DERIVATIVES USEFUL AS ANTIBIOTIC AGENTS

(75) Inventors: Michael Barry Gravestock, Waltham, MA (US); Daniel Robert Carcanague, Waltham, MA (US); Neil James Hales, Macclesfield (GB)

(73) Assignee: AstraZeneca AB, Sodertajle (SE)

( * ) Notice: Subject to any disclaimer, the term of this patent is extended or adjusted under 35 U.S.C. 154(b) by 20 days.

(21) Appl. No.: 10/546,373

(22) PCT Filed: Feb. 24, 2004

(86) PCT No.: PCT/GB2004/000730

§ 371 (c)(1),
(2), (4) Date: Aug. 19, 2005

(87) PCT Pub. No.: WO2004/078753

PCT Pub. Date: Sep. 16, 2004

(65) Prior Publication Data

US 2006/0270637 A1   Nov. 30, 2006

(30) Foreign Application Priority Data

Mar. 1, 2003  (GB) .................. 0304723.0
Aug. 8, 2003  (GB) .................. 0318607.9

(51) Int. Cl.
*C07D 413/14*  (2006.01)
*A61K 31/4427*  (2006.01)

(52) U.S. Cl. .................. 514/340; 546/271.4

(58) Field of Classification Search ................ 514/340; 546/271.4
See application file for complete search history.

(56) References Cited

U.S. PATENT DOCUMENTS

2002/0115669 A1   8/2002   Marina et al.

FOREIGN PATENT DOCUMENTS

| WO | WO 01/94342 A | 12/2001 |
|---|---|---|
| WO | WO 03/022824 | 3/2003 |

Primary Examiner—Zinna N. Davis

(57) ABSTRACT

Compounds of the formula (I), or a pharmaceutically-acceptable salt, or an in-vivo-hydrolysable ester thereof, (I) R1a is NH(C=W)R$_5$ or (a); W is O or S; R$_2$ and R$_3$ are for example H or F; R$_1$ is for example hydrogen, or halogen; R$_5$ is selected from hydrogen, (2–6C)alkyl (optionally substituted); R$_6$ and R$_7$ are independently selected from hydrogen, and (1–4C)alkyl (optionally substituted); wherein R$_4$ is either a hydroxymethyl substituent on C-4' of the isoxazoline ring; or R$_4$ is a hydroxymethyl substituent on C-5' of the isoxazoline ring and the stereochemistry at C-5' of the isoxazoline ring and at C-5 of the oxazolidinone ring is selected, such that the compound of formula (I) is a single diastereomer; are useful as antibacterial agents; and processes for their manufacture and pharmaceutical compositions containing them are described

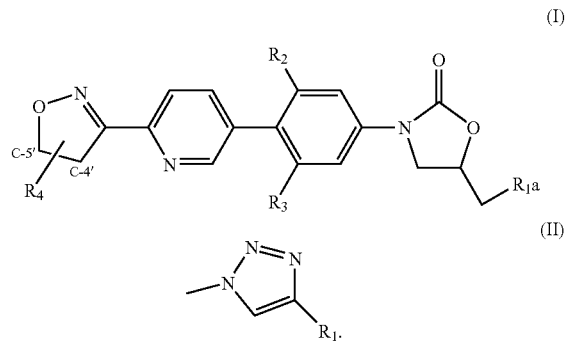

17 Claims, No Drawings

HYDROXYMETHYL SUBSTITUTED DIHYDROISOXAZOLE DERIVATIVES USEFUL AS ANTIBIOTIC AGENTS

CROSS-REFERENCE TO RELATED APPLICATIONS

This application is a US National Stage under 35 U.S.C § 371 of International Application No. PCT/GB2004/000730 (filed Feb. 24, 2004) which claims priority under 35 U.S.C. § 119(a)–(d) to Application Nos. GB 0304723.0 (filed Mar. 1, 2003) and GB 0318607.9 (filed Aug. 8, 2003), the specifications of which are incorporated herein by reference.

The present invention relates to antibiotic compounds and in particular to antibiotic compounds containing substituted oxazolidinone and isoxazoline rings. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded as effective against both Gram-positive and certain Gram-negative pathogens.

Gram-positive pathogens, for example Staphylococci, Enterococci, Streptococci and mycobacteria, are particularly important because of the development of resistant strains which are both difficult to treat and difficult to eradicate from the hospital environment once established. Examples of such strains are methicillin resistant *staphylococcus* (MRSA), methicillin resistant coagulase negative staphylococci (MRCNS), penicillin resistant *Streptococcus pneumoniae* and multiply resistant *Enterococcus faecium*.

The major clinically effective antibiotic for treatment of such resistant Gram-positive pathogens is vancomycin. Vancomycin is a glycopeptide and is associated with various toxicities, including nephrotoxicity. Furthermore, and most importantly, antibacterial resistance to vancomycin and other glycopeptides is also appearing. This resistance is increasing at a steady rate rendering these agents less and less effective in the treatment of Gram-positive pathogens. There is also now increasing resistance appearing towards agents such as β-lactams, quinolones and macrolides used for the treatment of upper respiratory tract infections, also caused by certain Gram negative strains including *H. influenzae* and *M. catarrhalis*.

Certain antibacterial compounds containing an oxazolidinone ring have been described in the art (for example, Walter A. Gregory et al in J. Med. Chem. 1990, 33, 2569–2578 and 1989, 32(8), 1673–81; Chung-Ho Park et al in J. Med. Chem. 1992, 35, 1156–1165). Bacterial resistance to known antibacterial agents may develop, for example, by (i) the evolution of active binding sites in the bacteria rendering a previously active pharmacophore less effective or redundant, and/or (ii) the evolution of means to chemically deactivate a given pharmacophore, and/or (iii) the evolution of efflux pathways. Therefore, there remains an ongoing need to find new antibacterial agents with a favourable pharmacological profile, in particular for compounds containing new, more potent, pharmacophores.

Additionally, certain antibacterial compounds containing an oxazolidinone ring have activity against the enzyme mono-amine oxidase (MAO), for instance compounds with amidomethyl or hydroxymethyl side chains at C-5 of the oxazolidinone ring. This may potentially lead to undesirable properties such as elevation in blood pressure when administered to a patient, or potentially cause drug-drug interactions. Therefore, there remains an ongoing need to find new antibacterial agents of the oxazolidinone class with a more favourable profile against MAO.

We have discovered a class of potentially bipharmacophoric antibiotic compounds containing a substituted oxazolidinone ring and a substituted isoxazoline ring which has useful activity against Gram-positive pathogens including MRSA and MRCNS and, in particular, against various strains exhibiting resistance to vancomycin and/or linezolid and against *E. faecium* strains resistant to both aminoglycosides and clinically used β-lactams, but also to fastidious Gram negative strains such as *H. influenzae, M. catarrhalis*, mycoplasma spp. and chlamydial strains. The compounds of the invention also demonstrate that a favourable, decreased, MAO potency may be derived from the sterochemistry of the substituent on the isoxazoline ring.

We use the term 'bipharmacophoric' to indicate that the substituted oxazolidinone and isoxazoline pharmacophores may independently bind at pharmacophore binding sites where the sites may be similar or different, where the similar or different sites may be occupied simultaneously or not simultaneously within a single organism, or where the relative importance of different binding modes to the similar or different sites may vary between two organisms of different genus. An illustrative example of binding to two sites which are different from each other is binding of one pharmacophore to a site causing antibacterial activity, with the other pharamacophore binding to a site giving rise to MAO activity.

Accordingly the present invention provides a compound of the formula (I),

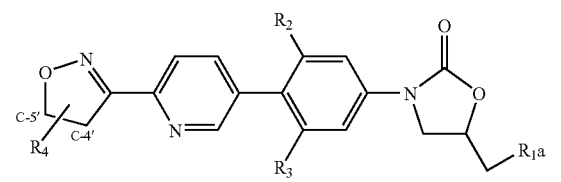

(I)

wherein:
$R_1a$ is —NH(C═W)$R_5$ or

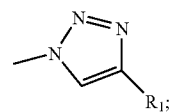

W is O or S;
$R_2$ and $R_3$ are independently selected from H, F, Cl, $CF_3$, OMe, SMe, Me and Et;
$R_1$ is selected from hydrogen, halogen, cyano, (1–4C)alkyl, cyano(1–4C)alkyl, halo(1–4C)alkyl, dihalo(1–4C)alkyl, trihalo(1–4C)alkyl, amino, (1–4C)alkylamino, di-(1–4C) alkylamino, (1–4C)alkylthio, (1–4C)alkoxy, (1–4C)

alkoxy(1–4C)alkyl, (2–4C)alkenyloxy, (2–4C)alkenyl, (2–4C)alkynyl, (3–6C)cycloalkyl, (3–6C)cycloalkenyl and (1–4C)alkoxycarbonyl;

and wherein at each occurrence of an $R_1$ substituent containing an alkyl, alkenyl, alkynyl, cycloalkyl or cycloalkenyl moiety each such moiety is optionally substituted on an available carbon atom with one, two, three or more substituents independently selected from F, Cl, Br, OH and CN;

$R_5$ is selected from hydrogen, (2–6C)alkyl (optionally substituted by 1, 2 or 3 substituents independently selected from methyl, chloro, bromo, fluoro, methoxy, methylthio, azido and cyano), methyl (optionally substituted by 1, 2 or 3 substituents independently selected from methyl, chloro, bromo, fluoro, methoxy, methylthio, hydroxy, benzyloxy, ethynyl, (1–4C)alkoxycarbonyl, azido and cyano), 5-halo-2-thienyl, —N($R_6$)$R_7$), —O$R_6$, —S$R_6$, (2–4C)alkenyl, -(1–8C)alkylaryl, per-halo(1–8C)alkyl, —(CH$_2$)p(3–6C cycloalkyl and —(CH$_2$)p(3–6C)cycloalkenyl wherein p is 0, 1 or 2;

$R_6$ and $R_7$ are independently selected from hydrogen, and (1–4C)alkyl (optionally substituted with one, two, three or more halogen atoms);

wherein $R_4$ is either a hydroxymethyl substituent on C-4' of the isoxazoline ring; or $R_4$ is a hydroxymethyl substituent on C-5' of the isoxazoline ring and the stereochemistry at C-5' of the isoxazoline ring and at C-5 of the oxazolidinone ring is selected, such that the compound of formula (I) is a single diastereomer; or pharmaceutically-acceptable salts or pro-drugs thereof.

It will be understood that where an $R_1$ substituent containing an alkyl, alkenyl, alkynyl, cycloalkyl or cycloalkenyl moiety is substituted on an available carbon atom with one, two, three or more substituents independently selected from F, Cl, Br, OH and CN, then the substitution is such that chemically stable compounds are formed. For example, an $R_1$ substituent may allowably contain a trifluoromethyl group but not a tri-hydroxymethyl group. The same convention is applied wherever such optional substituents are defined.

In this specification the term 'alkyl' includes straight chained and branched structures. For example, (1–4C)alkyl includes propyl and isopropyl. However, references to individual alkyl groups such as "propyl" are specific for the straight chained version only, and references to individual branched chain alkyl groups such as "isopropyl" are specific for the branched chain version only. In this specification, the terms 'alkenyl' and 'cycloalkenyl' include all positional and geometrical isomers. In this specification, the term 'aryl' is an unsubstituted carbocyclic aromatic group, in particular phenyl, 1- and 2-naphthyl.

There follow particular and suitable values for certain substituents and groups referred to in this specification. These values may be used where appropriate with any of the definitions and embodiments disclosed hereinbefore, or hereinafter. For the avoidance of doubt each stated species represents a particular and independent aspect of this invention.

Examples of (1–4C)alkyl include methyl, ethyl, propyl and isopropyl; examples of (2–6C)alkyl include ethyl, propyl, isopropyl, butyl, tert-butyl, pentyl and hexyl; examples of hydroxy(1–4C)alkyl include hydroxymethyl, 2-hydroxyethyl, 2-hydroxypropyl and 3-hydroxypropyl; examples of cyano(1–4C)alkyl include cyanomethyl, 2-cyanoethyl, 1-cyanopropyl, 2-cyanopropyl and 3-cyanopropyl; examples of halo(1–4C)alkyl include fluoromethyl, chloromethyl, bromomethyl, 1-fluoroethyl and 2-chloroethyl; examples of dihalo(1–4C)alkyl include difluoromethyl and dichloromethyl; examples of trihalo(1–4C)alkyl include trifluoromethyl; examples of (2–4C)alkenyl include vinyl, propenyl, alkyl, butenyl; examples of (2–4C)alkenyloxy include ethenyloxy, prop-2-enyloxy, but-2-enyloxy and but-3-enyloxy; examples of (2–4C)alkynyl include ethynyl, prop-2-ynyl, but-2-ynyl and but-3-ynyl; examples of (1–4C)alkoxycarbonyl include methoxycarbonyl, ethoxycarbonyl, propoxycarbonyl and pentoxycarbonyl; examples of (1–4C)alkoxy include methoxy, ethoxy and propoxy; examples of (1–4C) alkoxy(1–4C)alkyl include methoxymethyl, ethoxymethyl and propoxyethyl; examples of (1–4C)alkylamino include methylamino, ethylamino and propylamino; examples of di-(1–4C)alkylamino include dimethylamino, methylethylamino and ethylpropylamino; examples of (1–4C)alkylthio include methylthio and ethylthio; examples of (3–6C)cycloalkyl include cyclopropyl, cyclobutyl, cyclopentyl and cyclohexyl; examples of (3–6C)cycloalkenyl include cyclobutenyl, cyclopentenyl and cyclohexenyl; examples of halo groups include fluoro, chloro and bromo; example of -(1–8C)alkylaryl include benzyl; examples of —(CH$_2$)$_p$(3–6C)cycloalkyl (p is 0, 1 or 2) include (3–6C)cycloalkyl, methylcyclopropyl, ethylcyclopropyl, and methylcyclobutyl; examples of —(CH$_2$)p(3–6C)cycloalkenyl (p is 0, 1 or 2) include (3–6C)cycloalkenyl, methylcyclopropenyl, ethylcyclopropenyl, and methylcyclobutenyl.

Suitable pharmaceutically-acceptable salts include acid addition salts such as methanesulfonate, ethanesulfonate, fumarate, succinate, hydrochloride, citrate, maleate, tartrate and (less preferably) hydrobromide. Also suitable are salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N N-dibenzylethylamine, tris-(2-hydroxyethyl)amine, N-methyl d-glucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

It will be understood that certain compounds of the present invention may exist in solvated, for example hydrated, as well as unsolvated forms. It is to be understood that the present invention encompasses all such solvated forms which possess the claimed pharmaceutical activity.

The compounds of the invention may be administered in the form of a pro-drug which is broken down in the human or animal body to give a compound of the invention. A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the invention and pharmaceutically-acceptable salts thereof.

Various forms of prodrugs are known in the art, for examples see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);
d) H. Bundgaard, et al., Journal of Pharmaceutical Sciences, 77, 285 (1988); and
e) N. Kakeya, et al., Chem Pharm Bull, 32, 692 (1984).

Suitable pro-drugs for pyridine or triazole derivatives include acyloxymethyl pyridinium or triazolium salts eg halides; for example pro-drugs such as:

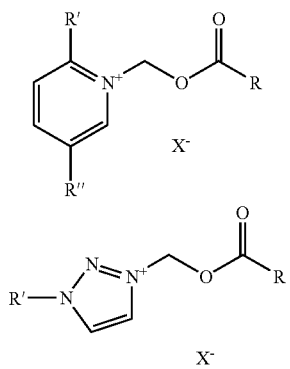

(Ref: T. Yamazaki et al. 42$^{nd}$ Interscience Conference on Antimicrobial Agents and Chemotherapy, San Diego, 2002; Abstract F820).

Suitable pro-drugs of hydroxy groups are glycosides, for example α- or β-glucosides, in the D- or L-configuration, such as the β-D glucoside of Example 40

Further suitable pro-drugs of hydroxyl groups are acyl esters of acetal-carbonate esters of formula RCOOC(R,R')OCO—, where R is (1–4C)alkyl and R' is (1–4C)alkyl or H. Further suitable prodrugs are carbonate and carbamate esters RCOO— and RNHCOO—.

A non-limiting example of a suitable pro-drug for a hydroxy group is provided herein by Example 6, and by Example 7, which are examples of pro-drugs for Example 1. Further examples of pro-drugs are provided by Examples 6 to 55. These pro-drugs are, in most cases, examples of in-vivo hydrolysable ester pro-drugs. Each of the Examples and each individual compound disclosed therein represents a separate and independent aspect of the invention.

An in-vivo hydrolysable ester of a compound of the formula (I) or a pharmaceutically-acceptable salt thereof containing carboxy or hydroxy group is, for example, a pharmaceutically-acceptable ester which is hydrolysed in the human or animal body to produce the parent acid or alcohol.

Suitable pharmaceutically-acceptable esters for carboxy include (1–6C)alkoxymethyl esters for example methoxymethyl, (1–6C)alkanoyloxymethyl esters for example pivaloyloxymethyl, phthalidyl esters, (3–8C)cycloalkoxycarbonyloxy(1–6C)alkyl esters for example 1-cyclohexylcarbonyloxyethyl; 1,3-dioxolan-2-onylmethyl esters for example 5-methyl-1,3-dioxolan-2-ylmethyl; and (1–6C)alkoxycarbonyloxyethyl esters for example 1-methoxycarbonyloxyethyl and may be formed at any carboxy group in the compounds of this invention.

An in-vivo hydrolysable ester of a compound of the invention or a pharmaceutically-acceptable salt thereof containing a hydroxy group or groups includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include (1–10C)alkanoyl, benzoyl, phenylacetyl and substituted benzoyl and phenylacetyl, (1–10C)alkoxycarbonyl (to give alkyl carbonate esters), di-(1–4C)alkylcarbamoyl and N-(di-(1–4C)alkylaminoethyl)-N-(1–4C)alkylcarbamoyl (to give carbamates), di-(1–4C)alkylaminoacetyl, carboxy(2–5C)alkylcarbonyl and carboxyacetyl. Examples of ring substituents on phenylacetyl and benzoyl include chloromethyl or aminomethyl, (1–4C)alkylaminomethyl and di-((1–4C)alkyl)aminomethyl, and morpholino or piperazino linked from a ring nitrogen atom via a methylene linking group to the 3- or 4-position of the benzoyl ring. Other interesting in-vivo hydrolysable esters include, for example, R$^4$C(O)O(1–6C)alkyl-CO— (wherein R$^4$ is for example, optionally substituted benzyloxy-(1–4C)alkyl, or optionally substituted phenyl; suitable substituents on a phenyl group in such esters include, for example, 4-(1–4C)piperazino-(1–4C)alkyl, piperazino-(1–4C)alkyl and morpholino-(1–4C)alkyl.

Further suitable in-vivo hydrolysable esters are those formed from amino acids. For examples, esters formed by reaction of a hydroxy group of a compound with the carboxylic acid of an amino acid. By the term "amino acid" herein we mean any α- or other amino substituted acid, naturally occurring or otherwise ie. non-naturally occurring, and derivatives thereof such as those formed by substitution (for example by alkylation on the nitrogen of the amino group). The use of either a natural or a non-natural amino acid represent particular and independent aspects of the invention. Examples of suitable α-amino acids and derivatives thereof, are valine, leucine, iso-leucine, N-methyl isoleucine, N-tert-butyl-isoleucine, lysine, glycine, N-methylglycine, N,N-dimethyl glycine, alanine, gluamine, asparagine, proline, and phenylalanine. In one embodiment, preferred amino acids are naturally occurring α-amino acids and N-alkylated derivatives thereof. Examples of such amino acid derived in-vivo hydrolysable esters are provided by Examples numbers 26, 41, 42, 46 and 55.

The use of amino acids having neutral and/or basic side chains represent particular and independent aspects of the invention.

Further in-vivo hydrolysable esters include phosphoramidic esters, and also compounds of invention in which any free hydroxy group independently forms a phosphoryl (npd is 1) or phosphiryl (npd is 0) ester of the formula (PD4):

(PD4)

For the avoidance of doubt, phosphono is —P(O)(OH)$_2$; (1–4C)alkoxy(hydroxy)phosphoryl is a mono-(1–4C)alkoxy derivative of —O—P(O)(OH)$_2$; and di-(1–4C)alkoxyphosphoryl is a di-(1–4C)alkoxy derivative of —O—P(O)(OH)$_2$.

Useful intermediates for the preparation of such esters include compounds containing a group/s of formula (PD4) in which either or both of the —OH groups in (PD4) is independently protected by (1–4C)alkyl (such compounds also being interesting compounds in their own right), phenyl or phenyl-(1–4C)alkyl (such phenyl groups being optionally substituted by 1 or 2 groups independently selected from (1–4C)alkyl, nitro, halo and (1–4C)alkoxy).

Thus, prodrugs containing groups such as (PD4) may be prepared by reaction of a compound of invention containing suitable hydroxy group/s with a suitably protected phosphorylating agent (for example, containing a chloro or dialkylamino leaving group), followed by oxidation (if necessary) and deprotection.

Other suitable prodrugs include phosphonooxymethyl ethers and their salts, for example a prodrug of R—OH such as:

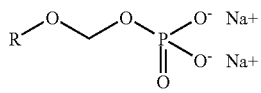

When a compound of invention contains a number of free hydroxy group, those groups not being converted into a prodrug functionality may be protected (for example, using a t-butyl-dimethylsilyl group), and later deprotected. Also, enzymatic methods may be used to selectively phosphorylate or dephosphorylate alcohol functionalities.

Where pharmaceutically-acceptable salts of an in-vivo hydrolysable ester may be formed this is achieved by conventional techniques. Thus, for example, compounds containing a group of formula (PD4) may ionise (partially or fully) to form salts with an appropriate number of counterions. Thus, by way of example, if an in-vivo hydrolysable ester prodrug of a compound of invention contains two (PD4) groups, there are four HO—P-functionalities present in the overall molecule, each of which may form an appropriate salt (i.e. the overall molecule may form, for example, a mono-, di-, tri- or tetra-sodium salt). A non-limiting example of pharmaceutically-acceptable salts of pro-drugs of compounds of the formula (I) is provided by Examples 20 and 26.

In one aspect, suitable pro-drugs of the invention are in-vivo hydrolysable esters such as (1–4C)alkyl esters; (1–4C)alkyl esters substituted with (1–4C)alkoxy, (1–4C) alkoxy(1–4C)alkoxy, carboxy, (1–4C)alkyl esters, amino, (1–4C)alkylamino, di(1–4C)alkylamino, tri(1–4C)alkylamino (thereby containing a quaternised nitrogen atom), aminocarbonyl, carbamates, amides or heterocyclyl groups (for example, an ester formed by reaction of the hydroxy group of $R^4$ with methoxy acetic acid, methoxypropionic acid, adipic acid momethylester, 4-dimethylaminobutanoic acid, 2-methylaminobutanoic acid, 5-amino pentanoic acid, β-alanine, N,N-diethylalanine, valine, leucine, iso-leucine, N-methyl isoleucine, N-tert-butyl-isoleucine, lysine, glycine, N,N-dimethyl glycine, alanine, sarcosine, glutamine, asparagine, proline, phenylalanine, nicotinic acid, nicotinic acid —N-oxide, pyrimidine-carboxylic acid (for example pyrimidine-5-carboxylic acid), pyrazine-carboxylic acid (for example pyrazine-2-carboxylic acid), or piperidine-4-carboxylic acid); (3–6C)cycloalkyl esters (optionally substituted by a (1–4C)alkoxycarbonyl, alkoxy or carboxy group); carbonates (for example (1–4C)alkylcarbonates and such carbonates substituted by (1–4C)alkoxy or di(1–4C)alkyl) amino); sulfates; phosphates and phosphate esters; and carbamates (see for example Example 10); and pharmaceutically acceptable salts thereof.

Further suitable pro-drugs are those formed by reaction of the hydroxy group of $R^4$ with carbonates, particularly alkoxysubstituted alkyl carbonates such as methoxypropylcarbonate, such as Example 29.

Further suitable pro-drugs are esters formed by reaction of the hydroxy group of $R^4$ with methoxy acetic acid, methoxypropionic acid, adipic acid momethylester, 4-dimethylaminobutanoic acid, 2-methylaminobutanoic acid, 5-amino pentanoic acid, β-alanine, N,N-diethylalanine, valine, leucine, iso-leucine, N-methyl isoleucine, N-tert-butyl-isoleucine, lysine, glycine, N,N-dimethyl glycine, alanine, sarcosine, glutamine, asparagine, proline, phenylalanine, nicotinic acid, nicotinic acid -N-oxide, pyrimidine-5-carboxylic acid, pyrazine-2-carboxylic acid, or piperidine-4-carboxylic acid, 2-carboxy-cyclohexane-1-carboxylic acid; and pharmaceutically acceptable salts thereof.

Particular compounds of the invention are in-vivo hydrolysable esters formed from amino acids, and pharmaceutically acceptable salts thereof.

Further particular compounds of the invention are in-vivo hydrolysable esters formed from 4-dimethylaminobutanoic acid, 2-methylaminobutanoic acid, 5-amino pentanoic acid, β-alanine, N,N-diethylalanine, valine, leucine, iso-leucine, N-methyl isoleucine, N-tert-butyl-isoleucine, lysine, glycine, N,N-dimethyl glycine, alanine, sarcosine, glutamine, asparagine, proline, phenylalanine; and pharmaceutically acceptable salts thereof.

Further particular compounds of the invention are in-vivo hydrolysable esters formed from valine, leucine, iso-leucine, N-methyl isoleucine, N-tert-butyl-isoleucine, lysine, glycine, N,N-dimethyl glycine, alanine, sarcosine, glutamine, asparagine, proline and phenylalanine; and pharmaceutically acceptable salts thereof.

Further particular compounds of the invention are in-vivo hydrolysable esters formed from iso-leucine, N-methyl isoleucine, N-tert-butyl-isoleucine, lysine, glycine, N,N-dimethyl glycine, alanine, sarcosine and proline; and pharmaceutically acceptable salts thereof.

Further particular compounds of the invention are in-vivo hydrolysable esters formed from iso-leucine, N-methyl isoleucine, lysine, glycine, N,N-dimethyl glycine, alanine, sarcosine and proline; and pharmaceutically acceptable salts thereof.

Further particular compounds of the invention are in-vivo hydrolysable esters formed from iso-leucine, glycine, N,N-dimethyl glycine, alanine, and sarcosine; and pharmaceutically acceptable salts thereof.

Further particular compounds of the invention are in-vivo hydrolysable esters formed from iso-leucine, N,N-dimethyl glycine, alanine, and sarcosine; and pharmaceutically acceptable salts thereof.

Most preferred compounds are in-vivo hydrolysable esters of Example 1 and pharmaceutically acceptable salts thereof; particularly esters formed by reaction with the carboxylic acid group of any amino acid as described hereinbefore.

In particular, most preferred compounds are in-vivo hydrolysable esters of Example 1 formed by reaction with the carboxylic acid group of iso-leucine, leucine, N,N-dimethyl glycine, alanine, phenylalanine, praline, valine or sarcosine and pharmaceutically acceptable salts thereof.

In one embodiment, a most preferred compound is the in-vivo hydrolysable ester of Example 1 formed by reaction with the carboxylic acid group of iso-leucine and pharmaceutically acceptable salts thereof.

In particular, a most preferred compound is the in-vivo hydrolysable ester of Example 1 formed by reaction with the carboxylic acid group of N,N-dimethyl glycine and pharmaceutically acceptable salts thereof.

In particular, a most preferred compound is the in-vivo hydrolysable ester of Example 1 formed by reaction with the carboxylic acid group of alanine and pharmaceutically acceptable salts thereof.

In particular, a most preferred compound is the in-vivo hydrolysable ester of Example 1 formed by reaction with the carboxylic acid group of sarcosine and pharmaceutically acceptable salts thereof.

In another embodiment, preferred compounds are in-vivo hydrolysable esters formed by reaction of a compound of the formula (I) with the carboxylic acid group of nicotinic acid; and pharmaceutically acceptable salts thereof.

In particular, a preferred compound is the in-vivo hydrolysable ester of Example 1 formed by reaction with the carboxylic acid group of nicotinic acid and pharmaceutically acceptable salts thereof.

In another embodiment, preferred compounds are in-vivo hydrolysable esters formed by reaction of a compound of the formula (I) with phosphates; and pharmaceutically acceptable salts thereof.

In particular, preferred compounds are the in-vivo hydrolysable esters of Example 1 formed by reaction with phosphoric acid or an ester thereof, and pharmaceutically acceptable salts thereof.

In another embodiment, preferred compounds are in-vivo hydrolysable esters formed by reaction of Example 1 with nicotinic acid derivatives and their pharmaceutically acceptable salts thereof.

The compounds of the present invention have a chiral centre at the C-5 position of the oxazolidinone ring and, at the C-4 or C-5 position of the isoxazoline ring. The pharmaceutically active diastereomer is of the formula (IA):

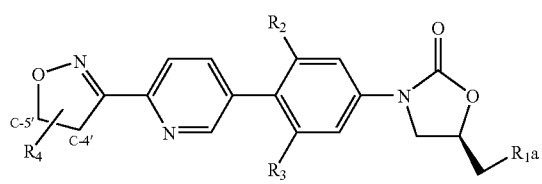

(IA)

and a preferred diastereomer is of the formula (IB):

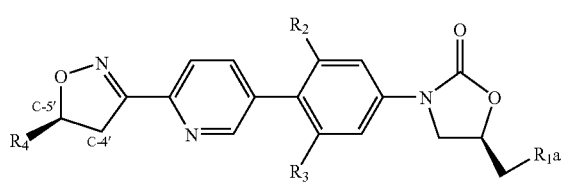

(IB)

Where $R_1a$ is N-linked-1,2,3-triazole, the pure diastereomer represented by (IB) has the (5R) configuration on the oxazolidinone ring. Where $R_1a$ is —NH(C=O)$R_5$, the pure diastereomer represented by (IB) has the (5S) configuration on the oxazolidinone ling. The diasteromer (IB) depicted above ($R_4$ is hydroxymethyl) has the (5'S) configuration on the isoxazoline ring. Where $R_4$ is at C-4', a similar convention applies to that described above for the substituent at C-5'.

If any mixture of epimers on the oxazolidinone chiral center is used, a larger amount (depending upon the ratio of the diastereoisomers) will be required to achieve the same effect as the same weight of the pharmaceutically active enantiomer.

Furthermore, some compounds of the invention may have other chiral centres, for example in $R_1a$. It is to be understood that the invention encompasses all such optical and diastereoisomers, and racemic mixtures, that possess antibacterial activity. It is well known in the art how to prepare optically-active forms (for example by resolution of the racemic form by recrystallisation techniques, by chiral synthesis, by enzymatic resolution, by biotransformation or by chromatographic separation) and how to determine antibacterial activity as described hereinafter.

Within the present invention it is to be understood that a compound of the formula (1) or a salt thereof may exhibit the phenomenon of tautomerism and that the formulae drawings within this specification can represent only one of the possible tautomeric forms. It is to be understood that the invention encompasses any tautomeric form which has antibacterial activity and is not to be limited merely to any one tautomeric form utilised within the formulae drawings.

As described hereinbefore, a preferred diastereomer is of the formula (IB). Compounds of the formula (IB) generally demonstrate a more favourable MAO profile in comparison with the C-5' epimer. Examples of MAO activity of preferred compounds of the invention are given below in comparison with their C-5' epimers showing that the (5'S) epimer has the higher Ki value (lower potency).

| Example No | Structure | MAO-A Ki (μM) |
|---|---|---|
| 1 | 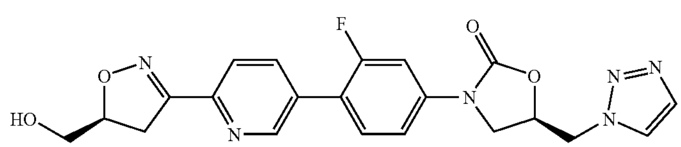 | 20 |
| 2 | 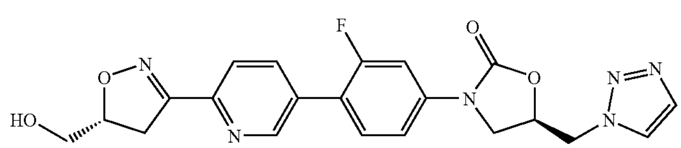 | 0.7 |
| 3 | 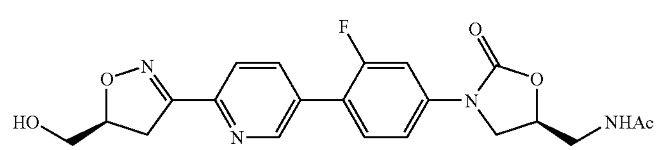 | 9 |

| Example No | Structure | MAO-A Ki (μM) |
|---|---|---|
| 4 | -continued ... (isoxazoline-pyridine-fluorophenyl-oxazolidinone-NHAc structure) | 3 |

It is also to be understood that certain compounds of the invention can exist in solvated as well as unsolvated forms such as, for example, hydrated forms. It is to be understood that the invention encompasses all such solvated forms which possess antibacterial activity.

It is also to be understood that certain compounds of the invention may exhibit polymorphism, and that the invention encompasses all such forms which possess antibacterial activity.

As stated before, we have discovered a range of compounds that have good activity against a broad range of Gram-positive pathogens including organisms known to be resistant to most commonly used antibiotics, together with activity against fastidious Gram negative pathogens such as *H. influenzae, M. catarrhalis, Mycoplasma* and *Chlamydia* strains. The following compounds possess preferred pharmaceutical and/or physical and/or pharmacokinetic properties. In particular, the following compounds possess favourable, decreased MAO potency.

Particularly preferred compounds of the invention comprise a compound of the invention, or a pharmaceutically-acceptable salt or an in-vivo hydrolysable ester thereof, wherein the substituents $R_1a$, $R_1$, $R_2$, $R_3$ and $R_4$ have values disclosed hereinbefore, or any of the following values (which may be used where appropriate with any of the definitions and embodiments disclosed hereinbefore or hereinafter).

In one aspect is provided a compound of the formula (I). In another aspect is provided a pharmaceutically acceptable salt of a compound of the formula (I). In another aspect is provided a pro-drug of a compound of the formula (I). In another aspect is provided an in-vivo hydrolysable ester of a compound of the formula (I). In a further aspect is provided a pharmaceutically acceptable salt of an in-vivo hydrolysable ester of a compound of the formula (I).

In one aspect, $R_2$ and $R_3$ are independently selected from hydrogen and fluorine. In one embodiment, $R_2$ and $R_3$ are both hydrogen. In another embodiment, $R_2$ is hydrogen and $R_3$ is fluorine.

In one aspect $R_1a$ is (N-linked 1,2,3-triazole substituted with $R_1$)

that is an N-linked 1,2,3-triazole which is substituted in the 4-position by $R_1$.

In another aspect $R_1a$ is —NH(C=W)$R_5$.

In one aspect W is oxygen. In another aspect, W is sulfur.

In one embodiment, $R_1$ is selected from hydrogen, halogen, cyano, (1–4C)alkyl, halo(1–4C)alkyl, dihalo(1–4C)alkyl and (2–4C)alkynyl.

In another embodiment, $R_1$ is selected from halogen, cyano, (1–4C)alkyl, halo(1–4C)alkyl, dihalo(1–4C)alkyl and (2–4C)alkynyl.

In another embodiment, $R_1$ is selected from hydrogen, halogen, cyano, halo(1–4C)alkyl, dihalo(1–4C)alkyl and (2–4C)alkynyl.

In another embodiment, $R_1$ is selected from halogen, cyano, (2–4C)alkyl, halo(1–4C)alkyl, dihalo(1–4C)alkyl and (2–4C)alkynyl.

In another embodiment, $R_1$ is selected from halogen, cyano, halo(1–4C)alkyl, dihalo(1–4C)alkyl and (2–4C)alkynyl.

Suitable values for $R_1$ are hydrogen, chloro, bromo, fluoro, methyl, fluoromethyl, chloromethyl, bromomethyl, difluoromethyl and dichloromethyl, ethynyl and propynyl.

Further suitable values for $R_1$ are chloro, bromo, fluoro, fluoromethyl, chloromethyl, bromomethyl, difluoromethyl and dichloromethyl, ethynyl and propynyl.

Further suitable values for $R_1$ are hydrogen, chloro, bromo, methyl and fluoromethyl.

Further suitable values for $R_1$ are hydrogen, chloro, bromo and fluoromethyl.

Further suitable values for $R_1$ are chloro, bromo, methyl and fluoromethyl.

Further suitable values for $R_1$ are chloro, bromo and fluoromethyl.

When W is O, suitably $R_5$ is selected from methyl, ethyl, dichloromethyl and cyclopropyl. Conveniently, when W is O, $R_5$ is selected from ethyl, dichloromethyl and cyclopropyl.

When W is S, suitably $R_5$ is selected from (1–4C)alkyl (optionally substituted by 1, 2 or 3 substituents independently selected from methyl, chloro, bromo, fluoro and methoxy), —N($R_6$)($R_7$) and —O$R_6$. More suitably, when W is S, $R_5$ is selected from —NH$_2$, —NHMe, —OMe, —SMe and methyl.

In one aspect $R_4$ is a substituent on C-4'. In another aspect $R_4$ is a substituent on C-5'.

When $R_4$ is a substituent on C-4', in one aspect the isoxazoline ring is of the (4'S) configuration. In another aspect, when $R_4$ is a substituent on C-4', the isoxazoline ring is of the (4'R) configuration.

When $R_4$ is a substituent on C-5', in one aspect the isoxazoline ring is of the (5'S) configuration. In another aspect, when $R_4$ is a substituent on C-5', the isoxazoline ring is of the (5'R) configuration. Preferably, the isoxazoline ring is of the (5'S) configuration.

In one aspect, $R_6$ and $R_7$ are independently selected from hydrogen and methyl.

In one embodiment is provided a compound of the formula (IC), or a pharmaceutically-acceptable salt or in-vivo hydrolysable ester thereof:

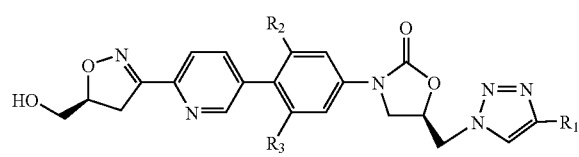

(IC)

wherein

R$_2$ and R$_3$ are independently selected from hydrogen and fluorine;

R$_1$ is selected from hydrogen, halogen, cyano, (1–4C)alkyl, halo(1–4C)alkyl, dihalo(1–4C)alkyl and (2–4C)alkynyl.

In a further aspect of the invention is provided a compound of the formula (IC) or a pharmaceutically-acceptable salt or in-vivo hydrolysable ester thereof, wherein R$_2$ and R$_3$ are independently selected from hydrogen and fluorine;

R$_1$ is selected from halogen, cyano, halo(1–4C)alkyl, dihalo(1–4C)alkyl and (2–4C)alkynyl.

In a further aspect of the invention is provided a compound of the formula (IC) or a pharmaceutically-acceptable salt or in-vivo hydrolysable ester thereof, wherein R$_2$ and R$_3$ are independently selected from hydrogen and fluorine;

R$_1$ is selected from hydrogen, chloro, bromo, fluoro, methyl, fluoromethyl, chloromethyl, bromomethyl, difluoromethyl, dichloromethyl, ethynyl and propynyl.

In a further aspect of the invention is provided a compound of the formula (IC) or a pharmaceutically-acceptable salt or in-vivo hydrolysable ester thereof, wherein R$_2$ and R$_3$ are independently selected from hydrogen and fluorine;

R$_1$ is selected from hydrogen, chloro, bromo, methyl and fluoromethyl.

In a further aspect of the invention is provided a compound of the formula (IC) or a pharmaceutically-acceptable salt or in-vivo hydrolysable ester thereof, wherein R$_2$ and R$_3$ are independently selected from hydrogen and fluorine;

R$_1$ is selected from chloro, bromo and fluoromethyl.

In a further aspect of the invention is provided a compound of the formula (IC) or a pharmaceutically-acceptable salt or in-vivo hydrolysable ester thereof, wherein R$_2$ and R$_3$ are independently selected from hydrogen and fluorine;

R$_1$ is selected from hydrogen and methyl.

In a further aspect of the invention is provided a compound of the formula (ID) or a pharmaceutically-acceptable salt or in-vivo hydrolysable ester thereof,

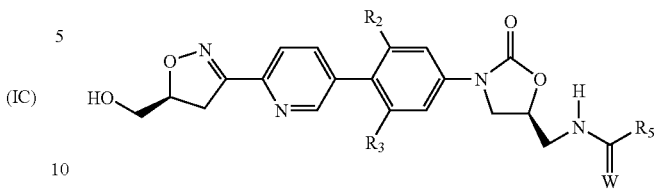

(ID)

wherein

W is O;

R$_2$ and R$_3$ are independently selected from hydrogen and fluorine;

R$_5$ is selected from methyl, ethyl, dichloromethyl and cyclopropyl.

In a further aspect of the invention is provided a compound of the formula (ID) or a pharmaceutically-acceptable salt or in-vivo hydrolysable ester thereof, wherein W is O;

R$_2$ and R$_3$ are independently selected from hydrogen and fluorine;

R$_5$ is selected from ethyl, dichloromethyl and cyclopropyl.

In a further aspect of the invention is provided a compound of the formula (ID) or a pharmaceutically-acceptable salt or in-vivo hydrolysable ester thereof, wherein W is S;

R$_2$ and R$_3$ are independently selected from hydrogen and fluorine;

R$_5$ is selected from (1–4C)alkyl (optionally substituted by 1, 2 or 3 substituents independently selected from methyl, chloro, bromo, fluoro and methoxy), —N(R$_6$)(R$_7$) and —OR$_6$;

R$_6$ and R$_7$ are independently selected from hydrogen and methyl.

In a further aspect of the invention is provided a compound of the formula (IE) or a pharmaceutically-acceptable salt or in-vivo hydrolysable ester thereof,

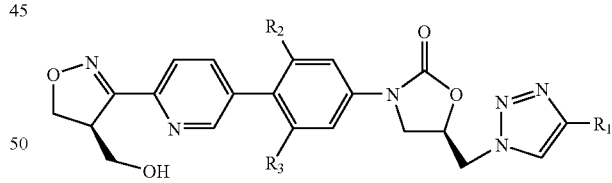

wherein

R$_2$ and R$_3$ are independently selected from hydrogen and fluorine;

R$_1$ is selected from hydrogen, halogen, cyano, (1–4C)alkyl, halo(1–4C)alkyl, dihalo(1–4C)alkyl and (2–4C)alkynyl.

In a further aspect of the invention is provided a compound of the formula (IE) or a pharmaceutically-acceptable salt or in-vivo hydrolysable ester thereof, wherein R$_2$ and R$_3$ are independently selected from hydrogen and fluorine;

R$_1$ is selected from halogen, cyano, halo(1–4C)alkyl, dihalo(1–4C)alkyl and (2–4C)alkynyl.

In a further aspect of the invention is provided a compound of the formula (IE) or a pharmaceutically-acceptable salt or in-vivo hydrolysable ester thereof, wherein R$_2$ and R$_3$ are independently selected from hydrogen and fluorine;

R$_1$ is selected from hydrogen, chloro, bromo, fluoro, methyl, fluoromethyl, chloromethyl, bromomethyl, difluoromethyl, dichloromethyl, ethynyl and propynyl.

In a further aspect of the invention is provided a compound of the formula (IF) or a pharmaceutically-acceptable salt or in-vivo hydrolysable ester thereof,

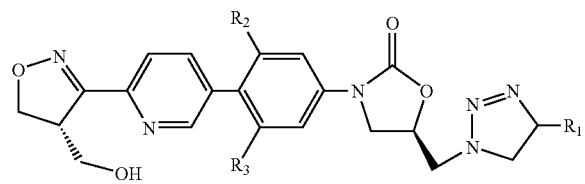

wherein

R$_2$ and R$_3$ are independently selected from hydrogen and fluorine;

R$_1$ is selected from hydrogen, (1–4C)alkyl, halo(1–4C)alkyl and hydrogen, halogen, (1–4C)alkyl, halo(1–4C)alkyl, dihalo(1–4C)alkyl and (2–4C)alkynyl.

In a further aspect of the invention is provided a compound of the formula (IF) or a pharmaceutically-acceptable salt or in-vivo hydrolysable ester thereof, wherein R$_2$ and R$_3$ are independently selected from hydrogen and fluorine;

R$_1$ is selected from halogen, cyano, halo(1–4C)alkyl, dihalo(1–4C)alkyl and (2–4C)alkynyl.

In a further aspect of the invention is provided a compound of the formula (IF) or a pharmaceutically-acceptable salt or in-vivo hydrolysable ester thereof, wherein R$_2$ and R$_3$ are independently selected from hydrogen and fluorine;

R$_1$ is selected from hydrogen, chloro, bromo, fluoro, methyl, fluoromethyl, chloromethyl, bromomethyl, difluoromethyl, dichloromethyl, ethynyl and propynyl.

In a further aspect of the invention is provided a compound of the formula (IG) or a pharmaceutically-acceptable salt or in-vivo hydrolysable ester thereof, wherein

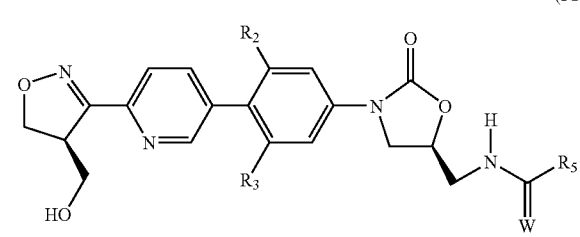

wherein

W is O;

R$_2$ and R$_3$ are independently selected from hydrogen and fluorine;

R$_5$ is selected from methyl, ethyl, dichloromethyl and cyclopropyl.

In a further aspect of the invention is provided a compound of the formula (IG) or a pharmaceutically-acceptable salt or in-vivo hydrolysable ester thereof, wherein W is S;

R$_2$ and R$_3$ are independently selected from hydrogen and fluorine;

R$_5$ is selected from (1–4C)alkyl (optionally substituted by 1, 2 or 3 substituents independently selected from methyl, chloro, bromo, fluoro and methoxy), —N(R$_6$)R$_7$ and —OR$_6$;

R$_6$ and R$_7$ are independently selected from hydrogen and methyl.

In a further aspect of the invention is provided a compound of the formula (IH) or a pharmaceutically-acceptable salt or in-vivo hydrolysable ester thereof, wherein

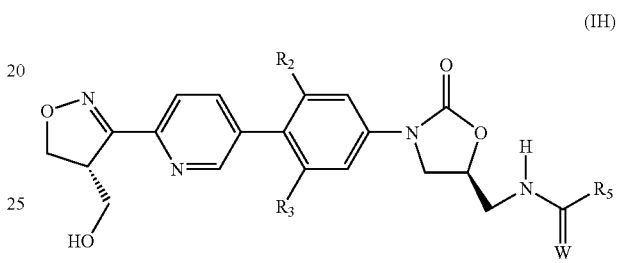

wherein

W is O;

R$_2$ and R$_3$ are independently selected from hydrogen and fluorine;

R$_5$ is selected from methyl, ethyl, dichloromethyl and cyclopropyl.

In a further aspect of the invention is provided a compound of the formula (IH) or a pharmaceutically-acceptable salt or in-vivo hydrolysable ester thereof, wherein W is S;

R$_2$ and R$_3$ are independently selected from hydrogen and fluorine;

R$_5$ is selected from (1–4C)alkyl (optionally substituted by 1, 2 or 3 substituents independently selected from methyl, chloro, bromo, fluoro and methoxy), —N(R$_6$)(R$_7$) and —OR$_6$;

R$_6$ and R$_7$ are independently selected from hydrogen and methyl.

Particularly preferred compounds of the present invention include the compounds described in the following examples, each of which provides an independent aspect of the invention. Therefore the present invention also provides a compound described in any one of the following examples, or a pharmaceutically-acceptable salt, solvate or an in-vivo hydrolysable ester thereof (and in particular compounds and salts thereof); and their use as a medicament (as herein described).

Process Section:

In a further aspect the present invention provides a process for preparing a compound of invention or a pharmaceutically-acceptable salt or an in-vivo hydrolysable ester thereof. It will be appreciated that during certain of the following processes certain substituents may require protection to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Greene & Peter Wuts (publisher: John Wiley & Sons). Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon. Resins may also be used as a protecting group.

The protecting groups may be removed at any convenient stage in the synthesis using conventional techniques well known in the chemical art.

A compound of the invention, or a pharmaceutically-acceptable salt or an in vivo hydrolysable ester thereof, may be prepared by any process known to be applicable to the preparation of chemically-related compounds. Such processes, when used to prepare a compound of the invention, or a pharmaceutically-acceptable salt or an in vivo hydrolysable ester thereof, are provided as a further feature of the invention and are illustrated by the following representative examples. Necessary starting materials may be obtained by standard procedures of organic chemistry (see, for example, Advanced Organic Chemistry (Wiley-Interscience), Jerry March). The preparation of such starting materials is described within the accompanying non-limiting Examples. Alternatively, necessary starting materials are obtainable by analogous procedures to those illustrated which are within the ordinary skill of an organic chemist. Information on the preparation of necessary starting materials or related compounds (which may be adapted to form necessary starting materials) may also be found in the certain Patent Application Publications, the contents of the relevant process sections of which are hereby incorporated herein by reference; for example WO 94-13649; WO 98-54161; WO 99-64416; WO 99-64417; WO 00-21960; WO 01-40222.

The skilled organic chemist will be able to use and adapt the information contained and referenced within the above references, and accompanying Examples therein and also the Examples herein, to obtain necessary starting materials, and products.

Thus, the present invention also provides that the compounds of the invention and pharmaceutically-acceptable salts and in-vivo hydrolysable esters thereof, can be prepared by a process (a) to (i) as follows (wherein the variables are as defined above unless otherwise stated):

a) by modifying a substituent in, or introducing a substituent into another compound of the invention by using standard chemistry (see for example, Comprehensive Organic Functional Group Transformations (Pergamon), Katritzky, Meth-Cohn & Rees); for example: a hydroxy group may be converted into an acylamino or thioacylamino group, for instance an acetamide group (optionally substituted or protected on the amido-nitrogen atom); into an acyloxy group, for instance an acetoxy group; a heterocyclyl group linked through nitrogen (optionally substituted on a carbon other than a carbon atom adjacent to the linking nitrogen ring atom), for instance an optionally 4-substituted 1,2,3-triazol-1-yl group; such conversions of the hydroxy group taking place directly (for instance by acylation or Mitsunobu reaction) or through the intermediacy of one or more derivatives (for instance a mesylate or an azide); an acyloxy group may be converted into a hydroxy group or into the groups that may be obtained from a hydroxy group (either directly or through the intermediacy of a hydroxy group);

an acylamino group or thioacylamino group may be converted into another acylamino group or thioacylamino group; into a heterocyclylamino group (optionally substituted or protected on the amino-nitrogen atom); a heterocyclyl group linked through nitrogen (optionally substituted on a carbon other than a carbon adjacent to the linking nitrogen atom), for instance an optionally 4-substituted 1,2,3-triazol-1-yl group; such conversions of the acylamino group taking place either directly or through the intermediacy of one or more derivatives such as an amino group;

a heterocyclyl group linked through nitrogen (optionally substituted on a carbon other than a carbon atom adjacent to the linking nitrogen ring atom) may be converted into another heterocyclyl group linked through nitrogen (optionally substituted on a carbon other than a carbon atom adjacent to the linking nitrogen ring atom) by introduction of a new ring substituent or by refunctionalisation of an existing ring substituent, for instance by modifying the 4-substituent of a 4-substituted 1,2,3-triazol-1-yl group.

b) by reaction of one part of a compound of formula (II) (wherein X is a leaving group useful in palladium [0]coupling, for example chloride, bromide, iodide, trifluoromethylsulfonyloxy, trimethylstannyl, trialkoxysilyl, or a boronic acid residue) with one part of a compound IIa, again with a leaving group X, such that the pyridyl-phenyl bond replaces the phenyl-X and pyridyl-X bonds; such methods are now well known, see for instance S. P. Stanforth, Catalytic Cross-Coupling Reactions in Biaryl Synthesis, *Tetrahedron*, 54, 1998, 263–303; J. K. Stille, *Angew Chem. Int. Ed. Eng.*, 1986, 25, 509–524; N. Miyaura and A Suzuki, *Chem. Rev.*, 1995, 95, 2457–2483; D. Baranano, G. Mann, and J. F. Hartwig, *Current Org. Chem.*, 1997, 1, 287–305; S. P. Stanforth, *Tetrahedron*, 54 1998, 263–303; P. R. Parry, C. Wang, A. S. Batsanov, M. R. Bryce; and B. Tarbit, *J. Org. Chem.*, 2002, 67, 7541–7543;

(II)

(IIa)

the leaving group X may be the same or different in the two molecules (II) and (IIa); for example:

c) by reaction of a pyridyl-phenyl carbamate derivative (III) with an appropriately substituted oxirane to form an oxazolidinone ring;

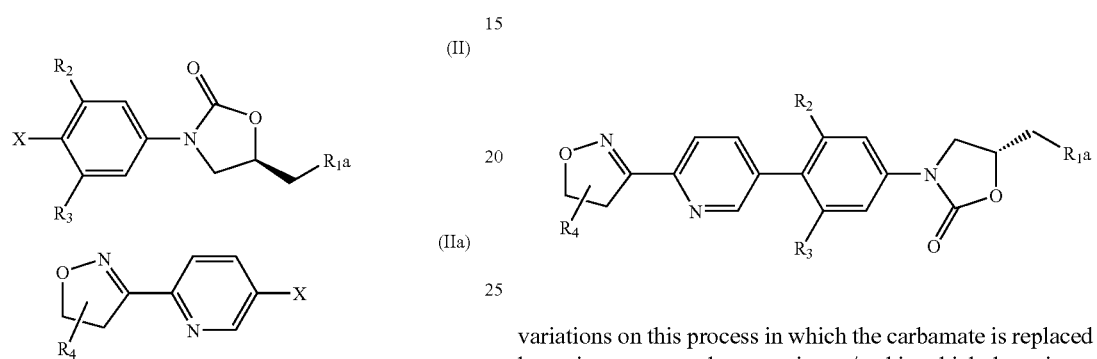

variations on this process in which the carbamate is replaced by an isocyanate or by an amine or/and in which the oxirane is replaced by an equivalent reagent X—CH$_2$CH(O-optionally protected)CH$_2$R$_1$a where X is a displaceable group are also well known in the art, for example,

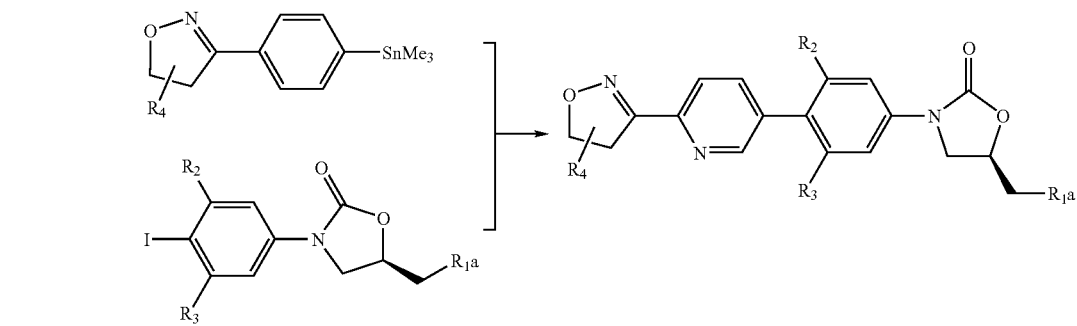

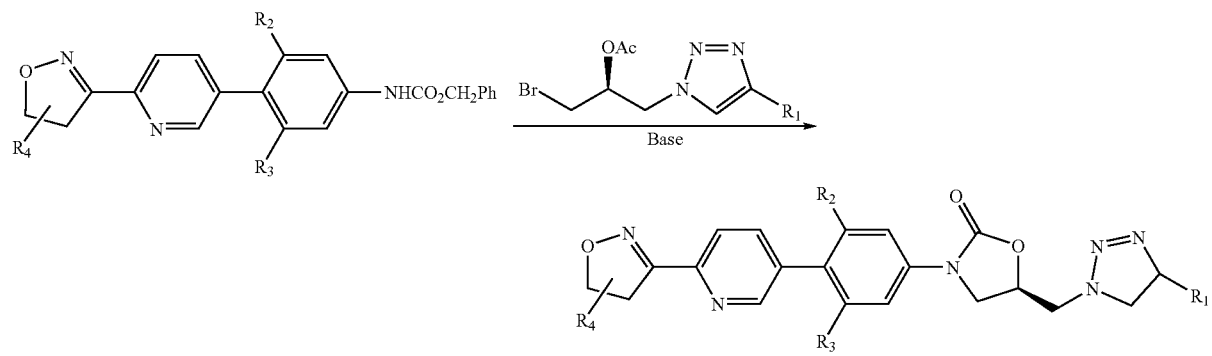

(d) by reaction of a compound of formula (IV):

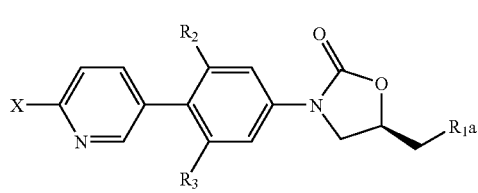
(IV)

where X is a replaceable substituent—such as chloride, bromide, iodide, trifluoromethylsulfonyloxy, trimethylstannyl, trialkoxysilyl, or a boronic acid residue with a compound of the formula (V):

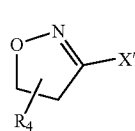
(V)

wherein X' is a replaceable substituent (such as chloride, bromide, iodide, trifluoromethylsulfonyloxy, trimethylstannyl, trialkoxysilyl, or a boronic acid residue); wherein the substituents X and X' are chosen to be complementary pairs of substituents known in the art to be suitable as complementary substrates for coupling reactions catalysed by transition metals such as palladium(0);

e) by reaction of a 3-pyridylphenylbiaryl aldehyde derivative (VI) to form an isoxazoline ring at the undeveloped heteroaryl position;

variations on this process in which the reactive intermediate (a nitrile oxide VII') is obtained other than by oxidation of an oxime (VII) are well known in the art;

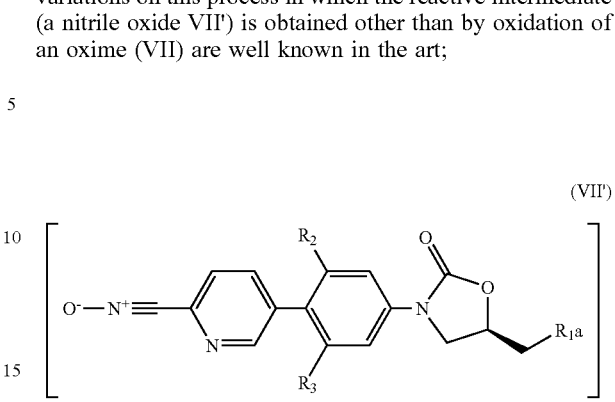
(VII')

f) when $R_1a$ is an N-linked 1,2,3-triazole, by formation of the triazole ring from a suitably functionalised intermediate in which the isoxazole-pyridyl-phenyl ring system is already formed, for example as illustrated by the scheme:

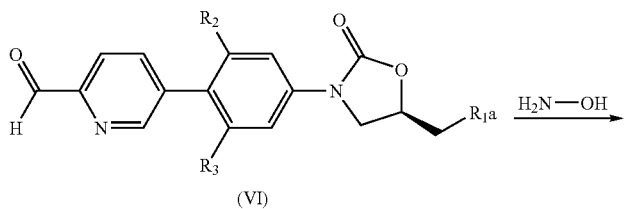
(VI)

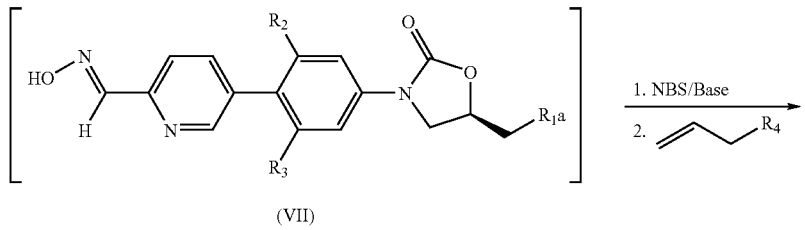
(VII)

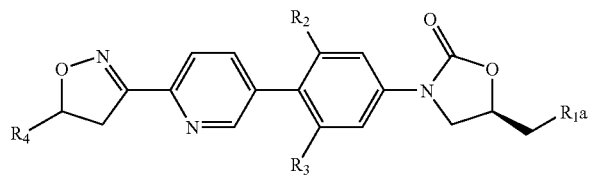

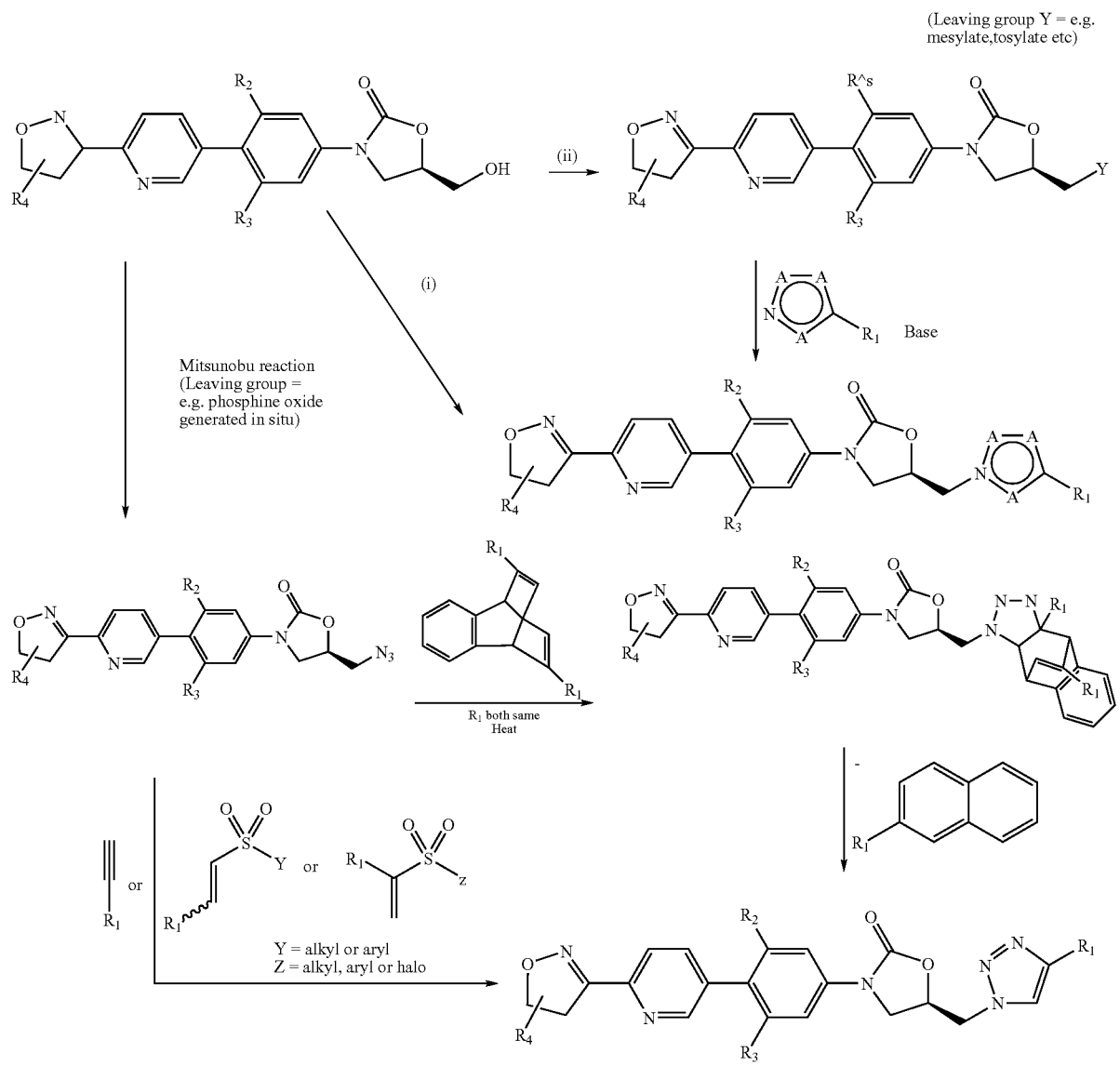
g) for $R_1a$ as a 1,2,3-triazole, compounds of the formula (I) may be made by cycloaddition via the azide to acetylenes, for example by reacting azidomethyl oxazolidinones with terminal alkynes using Cu(I) catalysis in e.g. aqueous alcoholic solution at ambient temperatures to give 4-substituted 1,2,3-triazoles (V. V. Rostovtsev, L. G. Green, V. V. Fokin, and K. B. Sharpless, Angew. Chem. Int. Ed., 2002, 41, 2596–2599):
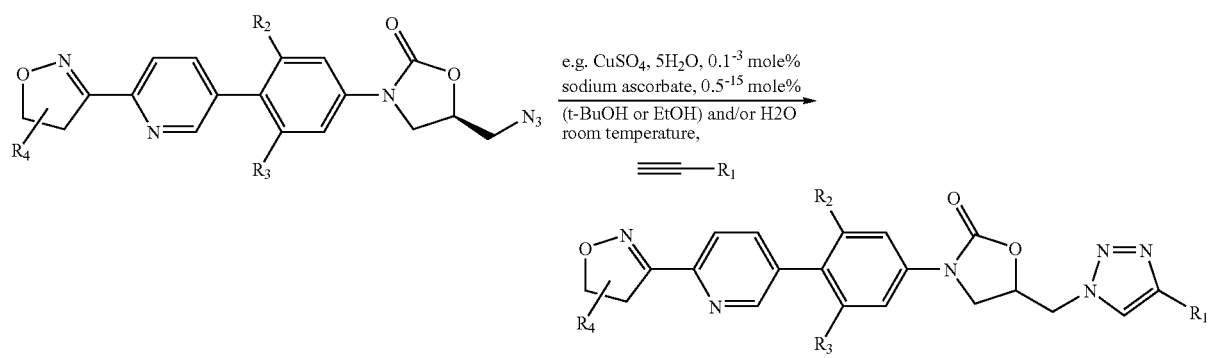

h) for $R_1a$ as 4-substituted 1,2,3-triazole, compounds of formula (I) may be made by reacting aminomethyloxazolidinones with 1,1-dihaloketone sulfonylhydrazones (Sakai, Kunihazu; Hida, Nobuko; Kondo, Kiyosi; *Bull. Chem. Soc. Jpn.*, 59, 1986, 179–183; Sakai, Kunikazu; Tsunemoto, Daiei; Kobori, Takeo; Kondo, Kiyoshi; Hido, Noboko EP 103840 A2 19840328);

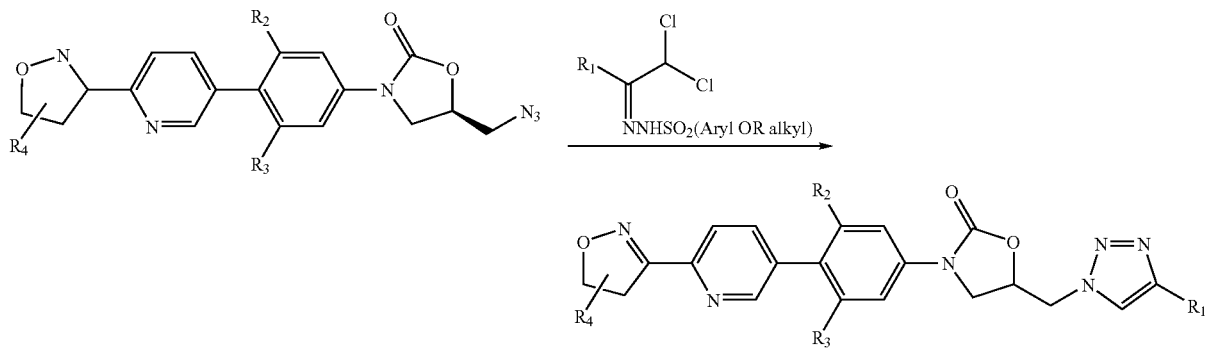

i) for $R_1a$ as 4-halogenated 1,2,3-triazoles, compounds of formula (I) may also be made by reacting azidomethyl oxazolidinones with halovinylsulfonyl chlorides at a temperature between 0° C. and 100° C., either without solvent or in an inert diluent such as chlorobenzene, chloroform or dioxan;

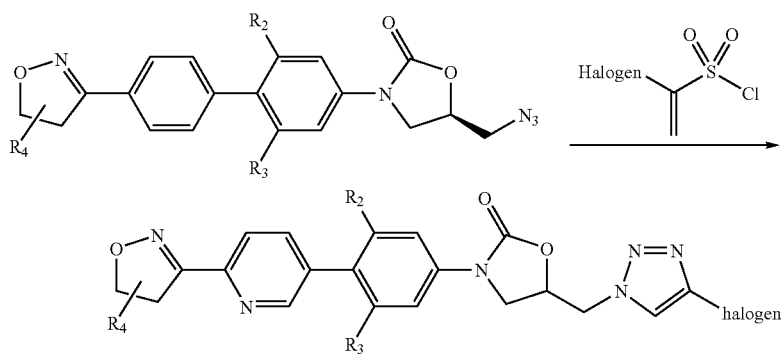

for the case when the halogen in the vinylsulfonylchloride reagent shown above is bromine see C. S. Rondestvedt, Jr. and P. K. Chang, *J. Amer. Chem. Soc.*, 77, 1955, 6532–6540; preparation of 1-bromo-1-ethenesulfonyl chloride by C. S. Rondestvedt, Jr., *J. Amer. Chem. Soc.*, 76, 1954, 1926–1929);

the cycloaddition reaction with 1-chloro-1-ethenesulfonyl chloride with an azide derivative in a process to form a compound of the formula (I) wherein $R_1a$ is 4-chloro-1,2,3-triazole is carried out at 0° C. and 100° C., preferably at room temperature, either in an inert solvent, preferably chlorobenzene, chloroform, or dioxan, or more preferably without a solvent.

j) for $R_1a$ as $NHCOCH_3$, compounds of formula (I) may be prepared by conventional methods described in the prior art (see for example Upjohn Patent Aplication WO 97/37980); or for example as illustrated below:

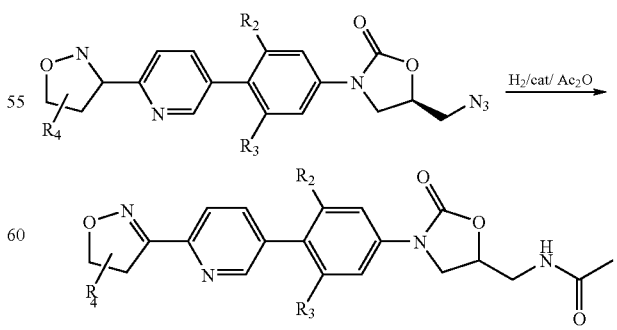

k) for $R_4$ on C'4, a suitably disubstituted olefin maybe used where Y is a regioselective directing group in the cycloaddition which is subsequently removed in a final step (for example Si(R)$_3$); for example where R$_4$ is an alkoxy methyl residue, a Z- or E-form olefin may be used, as illustrated below in Z form:

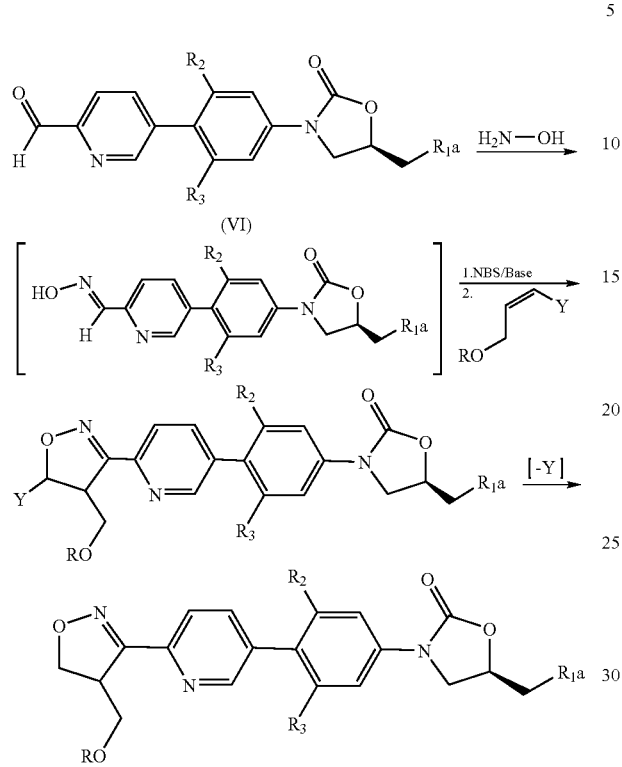

l) an alternative route to a preferred single hydroxyalkyl R$_4$ epimer at C4' or C5' is via enantioselective esterase hydrolysis of a racemic mixture of esters at that pro-chiral centre, wherein the unwanted isomer may be recycled, for example:

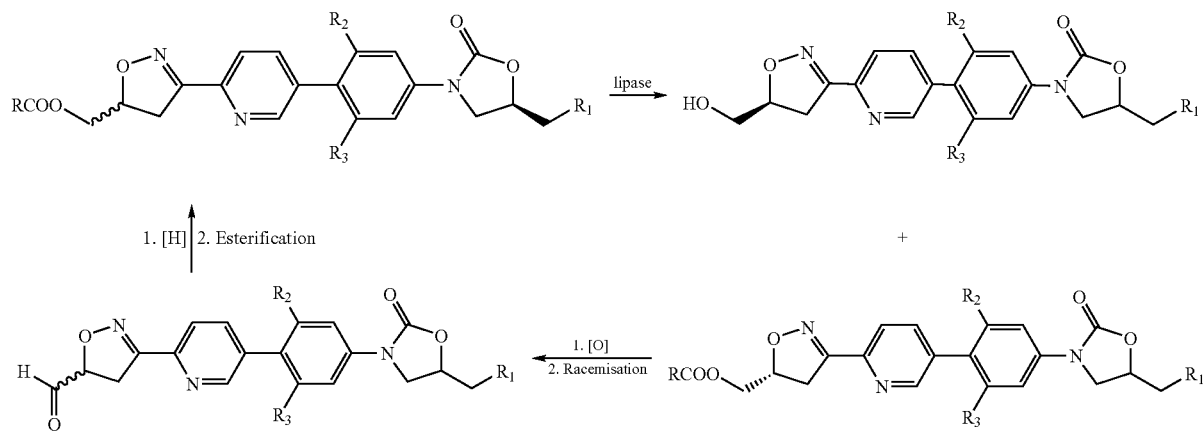

and thereafter if necessary:
i) removing any protecting groups;
ii) forming a pro-drug (for example an in-vivo hydrolysable ester); and/or
iii) forming a pharmaceutically-acceptable salt.

The formation of compounds of formulae (II) and (IIa) as used in b) above:

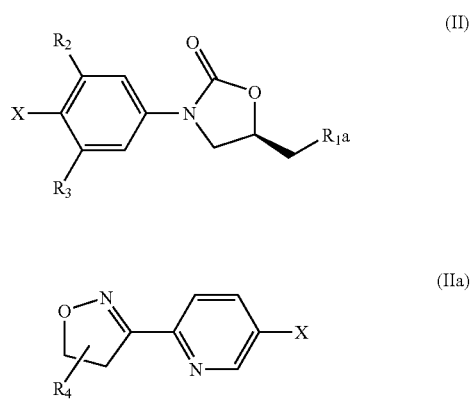

wherein each X is independently a leaving group useful in palladium [0] coupling, for example chloride, bromide, iodide, trifluoromethylsulfonyloxy, trimethylstannyl, trialkoxysilyl, or a boronic acid residue may be carried out by any method known in the art for assembling such types of compounds.

For example, where R$_1$a is a triazole ring, the 3 ring system of a compound of formula (II) may be assembled in a number of different ways as illustrated below for the unsubstituted triazole. Similar processes may be used for substituted triazoles and other values of R$_1$a. It will be appreciated that X in formula (II) as shown in the scheme below may be the same throughout the assembly of the 3 ring system, or may be altered at an appropriate point prior to coupling with the compound of formula (IIa); for example a compound of formula (II) wherein X is I or Br may be converted to a compound where X is a boronic acid or ester, or a trimethylstannyl derivative and then coupled with a compound of formula (IIa) with a suitable substituent X, for example Br or I. Alternatively, a compound of the formula (IIa) wherein X is a boronic acid or ester, or a trimethylstannyl derivative, may be reacted with a compound of formula (II) wherein X is a suitable halo derivative such as I or Br.

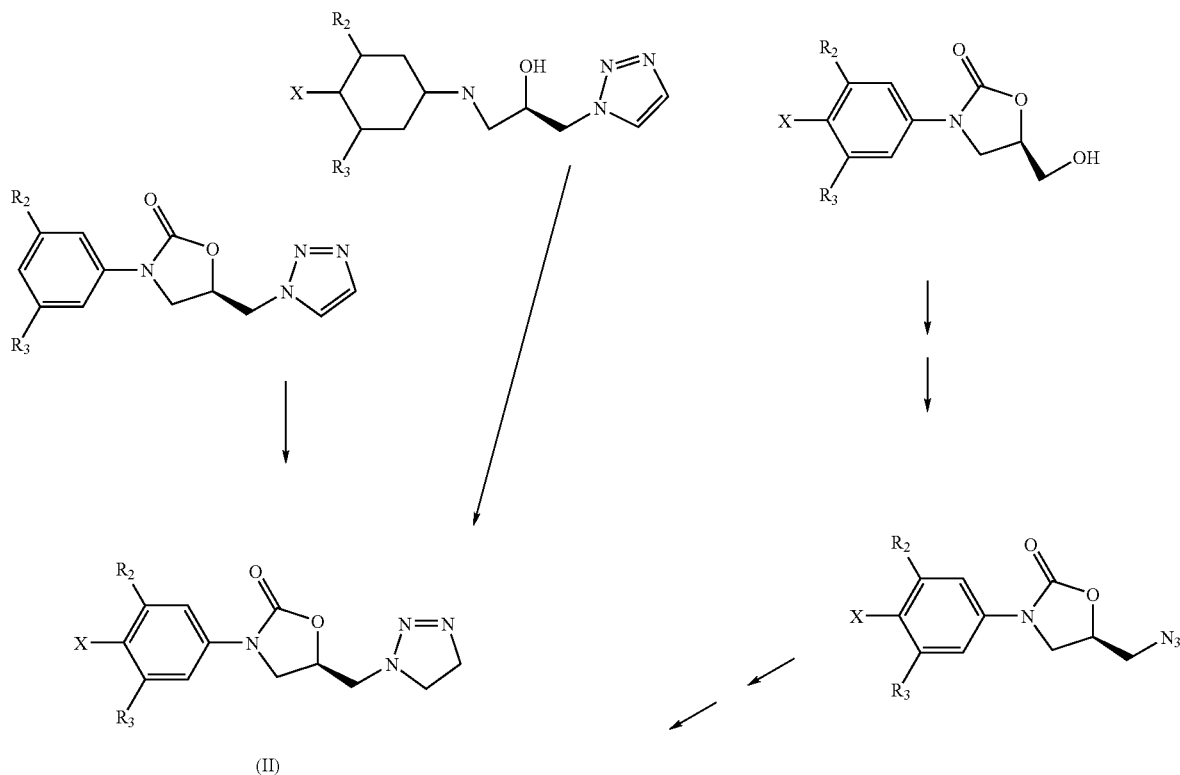

(II)

Compounds of formula (IIa) may be derived from an oxime substituted pyridine derivative as shown below, wherein X is Br or I. The oxime derivative itself may be derived from simple halo-pyridine derivatives via aldehydo-halopyridines. The chiral centre on the isoxazole ring may be introduced by any means known in the art, for example by resolution of an ester group, for instance using an enzyme such as a lipase to achieve selectivity. This process is illustrated below for a butyl ester, however it will be appreciated that other alkyl or alkenyl esters may be used, and that resolution and hydrolysis may be achieved in a single step by enzyme catalysed selective ester hydrolysis. It will be appreciated that X in formula (IIa) as shown in the scheme below may be the same throughout the assembly of the 2 ring system, or may be altered at an appropriate point prior to coupling with the compound of formula (II):

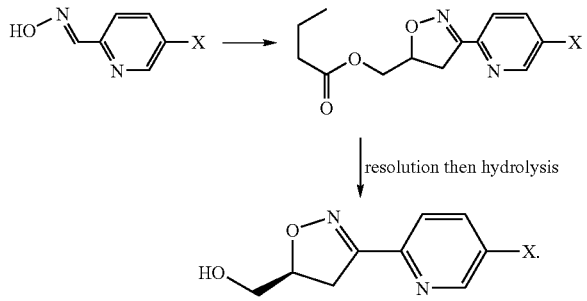

Compounds of the formula (II) wherein X is a boronic acid or ester are novel and form an independent aspect of the invention. Particular compounds of this aspect of the invention are compounds of the formula (I) wherein $R_2$ and $R_3$ are independently selected from H and F, $R_1a$ is

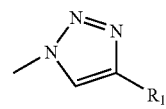

and $R_1$ is selected from hydrogen, halogen and (1–4C)alkyl; more particularly $R_1$ is selected from hydrogen and (1–4C) alkyl.

Compounds of the formula (IIa) wherein X is a boronic acid or ester are novel and form an independent aspect of the invention. Particular compounds of this aspect of the invention are compounds of the formula (IIa) wherein $R_4$ is a hydroxymethyl substituent on C-4' or C-5' of the isoxazoline ring, more particularly $R_4$ is a substituent on C-5', even more particularly wherein the compound of formula (IIa) is a single stereoisomer.

It will be understood that by "X is a boronic acid or ester" means X is the group —B(OR$^A$)(OR$^B$), wherein R$^A$ and R$^B$ are independently selected from hydrogen and a (1–4C)alkyl group (such as methyl, ethyl and isopropyl), or R$^A$ and R$^B$ together form a 2 or 3 carbon bridge between the two oxygen atoms attached to the boron atom to form a 5- or 6-membered ring respectively (wherein the 2 or 3 carbon bridge is optionally substituted by 1 to 4 methyl groups, for example to form a 1,1,2,2-tetramethylethylene bridge), or R$^A$ and R$^B$ together form a 1,2-phenyl group (thereby giving a catechol ester).

The removal of any protecting groups, the formation of a pharmaceutically-acceptable salt and/or the formation of an in vivo hydrolysable ester or other pro-drug are within the skill of an ordinary organic chemist using standard techniques. Furthermore, details on the these steps, for example the preparation of in-vivo hydrolysable ester prodrugs has been provided, for example, in the section above on such esters.

When an optically active form of a compound of the invention is required, it may be obtained by carrying out one of the above procedures using an optically active starting material (formed, for example, by asymmetric induction during a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the invention is required, it may be obtained by carrying out one of the above procedures using a pure regioisomer as a starting material, or by resolution of a mixture of the regioisomers or intermediates using a standard procedure.

According to a further feature of the invention there is provided a compound of the invention, or a pharmaceutically-acceptable salt, or in-vivo hydrolysable ester thereof for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt, or in-vivo hydrolysable ester thereof.

The invention also provides a compound of the invention, or a pharmaceutically-acceptable salt, or in-vivo hydrolysable ester thereof, for use as a medicament; and the use of a compound of the invention of the present invention, or a pharmaceutically-acceptable salt, or in-vivo hydrolysable ester thereof, in the manufacture of a medicament for use in the production of an antibacterial effect in a warm blooded animal, such as man.

In order to use a compound of the invention, an in-vivo hydrolysable ester or a pharmaceutically-acceptable salt thereof, including a pharmaceutically-acceptable salt of an in-vivo hydrolysable ester, (hereinafter in this section relating to pharmaceutical composition "a compound of this invention") for the therapeutic (including prophylactic) treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the invention, an in-vivo hydrolysable ester or a pharmaceutically-acceptable salt thereof, including a pharmaceutically-acceptable salt of an in-vivo hydrolysable ester, and a pharmaceutically-acceptable diluent or carrier.

The compositions of the invention may be in a form suitable for oral use (for example as tablets, lozenges, hard or soft capsules, aqueous or oily suspensions, (lipid) emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above.

Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

A pharmaceutical composition to be dosed intravenously may contain advantageously (for example to enhance stability) a suitable bactericide, antioxidant or reducing agent, or a suitable sequestering agent.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 1 mg to 1 g of active agent compounded with an appropriate and convenient amount of excipients which may vary from about 5 to about 98 percent by weight of the total composition. Dosage unit forms will generally contain about 100 mg to about 1 g of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

A suitable pharmaceutical composition of this invention is one suitable for oral administration in unit dosage form, for example a tablet or capsule which contains between 1 mg and 1 g of a compound of this invention, preferably between 100 mg and 1 g of a compound. Especially preferred is a tablet or capsule which contains between 50 mg and 800 mg of a compound of this invention, particularly in the range 100 mg to 500 mg.

In another aspect a pharmaceutical composition of the invention is one suitable for intravenous, subcutaneous or intramuscular injection, for example an injection which contains between 0.1% w/v and 50% w/v (between 1 mg/ml and 500 mg/ml) of a compound of this invention.

Each patient may receive, for example, a daily intravenous, subcutaneous or intramuscular dose of 0.5 mgkg$^{-1}$ to 20 mgkg$^{-1}$ of a compound of this invention, the composition being administered 1 to 4 times per day. In another embodiment a daily dose of 5 mgkg$^{-1}$ to 20 mgkg$^{-1}$ of a compound of this invention is administered. The intravenous, subcutaneous and intramuscular dose may be given by means of a bolus injection. Alternatively the intravenous dose may be given by continuous infusion over a period of time. Alternatively each patient may receive a daily oral dose which may be approximately equivalent to the daily parenteral dose, the composition being administered 1 to 4 times per day.

In addition to the compounds of the present invention, the pharmaceutical composition of this invention may also contain (ie through co-formulation) or be co-administered (simultaneously, sequentially or separately) with one or more known drugs selected from other clinically useful antibacterial agents (for example, β-lactams, macrolides, quinolones or aminoglycosides) and/or other anti-infective agents (for example, an antifungal triazole or amphotericin). These may include carbapenems, for example meropenem or imipenem, to broaden the therapeutic effectiveness. Compounds of this invention may also be co-formulated or co-administered with bactericidal/permeability-increasing protein (BPI) products or efflux pump inhibitors to improve activity against gram negative bacteria and bacteria resistant to antimicrobial agents. Compounds of this invention may also be co-formulated or co-administered with a vitamin, for example Vitamin B, such as Vitamin B2, Vitamin B6, Vitamin B12 and folic acid. Compounds of the invention may also be formulated or co-administered with cyclooxygenase (COX) inhibitors, particularly COX-2 inhibitors.

In one aspect of the invention, a compound of the invention is co-formulated with an antibacterial agent which is active against gram-positive bacteria.

In another aspect of the invention, a compound of the invention is co-formulated with an antibacterial agent which is active against gram-negative bacteria.

In another aspect of the invention, a compound of the invention is co-administered with an antibacterial agent which is active against gram-positive bacteria.

In another aspect of the invention, a compound of the invention is co-administered with an antibacterial agent which is active against gram-negative bacteria.

In the above other, pharmaceutical composition, process, method, use and medicament manufacture features, the alternative and preferred embodiments of the compounds of the invention described herein also apply.

Antibacterial Activity:

The pharmaceutically-acceptable compounds of the present invention are useful antibacterial agents having a good spectrum of activity in vitro against standard Gram-positive organisms, which are used to screen for activity against pathogenic bacteria. Notably, the pharmaceutically-acceptable compounds of the present invention show activity against enterococci, pneumococci and methicillin resistant strains of *S. aureus* and coagulase negative staphylococci, together with *haemophilus* and *moraxella* strains. The antibacterial spectrum and potency of a particular compound may be determined in a standard test system.

The (antibacterial) properties of the compounds of the invention may also be demonstrated and assessed in-vivo in conventional tests, for example by oral and/or intravenous dosing of a compound to a warm-blooded mammal using standard techniques.

The following results were obtained on a standard in-vitro test system. The activity is described in terms of the minimum inhibitory concentration (MIC) determined by the agar-dilution technique with an inoculum size of $10^4$ CFU/spot. Typically, compounds are active in the range 0.01 to 256 μg/ml.

Staphylococci were tested on agar, using an inoculum of $10^4$ CFU/spot and an incubation temperature of 37° C. for 24 hours—standard test conditions for the expression of methicillin resistance.

Streptococci and enterococci were tested on agar supplemented with 5% defibrinated horse blood, an inoculum of $10^4$ CPU/spot and an incubation temperature of 37° C. in an atmosphere of 5% carbon dioxide for 48 hours—blood is required for the growth of some of the test organisms. Fastidious Gram negative organisms were tested in Mueller-Hinton broth, supplemented with hemin and NAD, grown aerobically for 24 hours at 37° C., and with an innoculum of $5 \times 10^4$ CFU/well.

For example, the following results were obtained for the compound of Example 1:

| Organism | | MIC (μg/ml) |
|---|---|---|
| *Staphylococcus aureus*: | MSQS | 0.25 |
| | MRQR | 0.5 |
| *Streptococcus pneumoniae* | | 0.02 |
| *Haemophilus influenzae* | | 4 |
| *Moraxella catarrhalis* | | 0.5 |

MSQS = methicillin sensitive and quinolone sensitive
MRQR = methicillin resistant and quinolone resistant The activity of the compounds of the invention against MAO-A was tested using a standard in-vitro assay based on human liver enzyme expressed in yeast as described in Biochem. Biophys. Res. Commun. 1991, 181, 1084–1088. When Ki values were measured in such an assay as above, Example 1 showed a Ki value of 20 μM.

Certain intermediates and/or Reference Examples described hereinafter are within the scope of the invention and may also possess useful activity, and are provided as a further feature of the invention.

The invention is now illustrated but not limited by the following Examples in which unless otherwise stated:
(i) evaporations were carried out by rotary evaporation in-vacuo and work-up procedures were carried out after removal of residual solids by filtration;
(ii) operations were carried out at ambient temperature, that is typically in the range 18–26° C. and without exclusion of air unless otherwise stated, or unless the skilled person would otherwise work under an inert atmosphere;
(iii) column chromatography (by the flash procedure) was used to purify compounds and was performed on Merck Kieselgel silica (Art. 9385) unless otherwise stated;
(iv) yields are given for illustration only and are not necessarily the maximum attainable;
(v) the structure of the end-products of the invention were generally confirmed by NMR and mass spectral techniques [proton magnetic resonance spectra were generally determined in DMSO-$d_6$ unless otherwise stated using a Bruker DRX-300 spectrometer operating at a field strength of 300 MHz, or a Bruker DRX-500 spectrometer operating at a field strength of 500 MHz; chemical shifts are reported in parts per million downfield from tetramethysilane as an internal standard (δscale) and peak multiplicities are shown thus: s, singlet; d, doublet; AB or dd, doublet of doublets; dt, doublet of triplets; dm, doublet of multiplets; t, triplet, m, multiplet; br, broad; fast-atom bombardment NAB) mass spectral data were generally obtained using a Platform spectrometer (supplied by Micromass) run in electrospray and, where appropriate, either positive ion data or negative ion data were collected]; optical rotations were determined at 589 nm at 20° C. for 7.6 mM solutions in methanol using a Perkin Elmer Polarimeter 341;
(vi) each intermediate was purified to the standard required for the subsequent stage and was characterised in sufficient detail to confirm that the assigned structure was correct; purity was assessed by HPLC, TLC, or NMR and identity was determined by infra-red spectroscopy (IR), mass spectroscopy or NMR spectroscopy as appropriate;
(vii) in which the following abbreviations may be used:
DMF is N,N-dimethylformamide; DMA is N,N-dimethylacetamide; TLC is thin layer chromatography; HPLC is high pressure liquid chromatography; MPLC is medium pressure liquid chromatography; DMSO is dimethylsulfoxide; CDCl$_3$ is deuterated chloroform; MS is mass spectroscopy; ESP is electrospray; EI is electron impact; CI is chemical ionisation; APCI is atmospheric pressure chemical ionisation; EtOAc is ethyl acetate; Et$_2$O is diethyl ether; MeOH is methanol; phosphoryl is (HO)$_2$—P(O)—O—; phosphiryl is (HO)$_2$—P—O—; Bleach is "Clorox" 6.15% sodium hypochlorite;
(viii) temperatures are quoted as ° C.

EXAMPLES

Example 1

(5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one

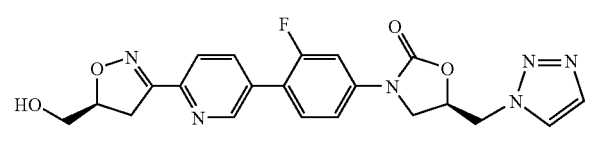

[(5S)-3-(5-Bromopyridin-2-yl)-4,5-dihydroisoxazol-5-yl]methanol (Intermediate 11, 0.277 g, 1.08 mmol), (5R)-3-[3-fluoro-4-(4,4,5,5-tetramethyl-1,3,2-dioxaborolan-2-yl)phenyl]-5-(1H -1,2,3-triazol-1-ylmethyl)-1,3-oxazolidin-2-one (Intermediate 7, 0.35 g, 0.9 mmol), potassium carbonate (0.622 g, 4.5 mmol), and tetrakis(triphenylphosphino)palladium(0) (0.1 g, 0.09 mmol) were combined and suspended in DMF (7 ml) and water (1 ml). The mixture was heated at 75° C. for 2 hours, then was poured into cold water (30 ml). The solids formed were collected, rinsed with water and washed with dichloromethane (2×10 ml), the solids were then dissolved in warm trifluoroethanol (2 ml), and further purified by column chromatography, eluting with 8% methanol in dichloromethane to give the title compound as a white solid (0.193 g).

MS (ESP): 439.22 (M+1) for $C_{21}H_{19}FN_6O_4$

NMR(300 Mz)(DMSO-d$_6$) δ: 3.36–3.58 (m, 4H); 3.95 (dd, 1H); 4.29 (t, 1H); 4.78 (m, 1H); 4.86 (d, 2H); 5.02 (t, 1H); 5.18 (m, 1H); 7.41 (dd, 1H); 7.58 (dd, 1H); 7.69 (t, 1H); 7.77 (s, 1H); 7.98 (d, 1H); 8.05 (dd, 1H); 8.18 (s, 1H); 8.78 (s, 1H).

Intermediate 1: Acetic acid (5R)-3-(3-fluoro-phenyl)-2-oxo-oxazolidin-5-ylmethyl ester

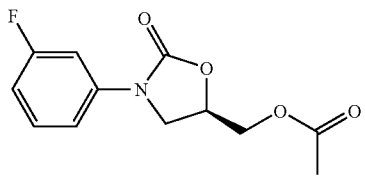

(5R)-3-(3-Fluorophenyl)-5-hydroxymethyloxazolidin-2-one (40 g, 0.189 mol, see Upjohn WO 94-13649) was suspended by stirring in dry dichloromethane (400 ml) under nitrogen. Triethylamine (21 g, 0.208 mol) and 4-dimethylaminopyridine (0.6 g, 4.9 mmol) were added, followed by dropwise addition of acetic anhydride (20.3 g, 0.199 mol) over 30 minutes, and stirring continued at ambient temperature for 18 hours. Saturated aqueous sodium bicarbonate (250 ml) was added, the organic phase separated, washed with 2% sodium dihydrogen phosphate, dried (magnesium sulfate), filtered and evaporated to give the desired product (49.6 g) as an oil.

MS (ESP): 254 (MH$^+$) for $C_{12}H_{12}FNO_4$

NMR(300 MHz) (CDCl$_3$) δ: 2.02 (s, 3H); 3.84 (dd, 1H); 4.16 (t, 1H); 4.25 (dd, 1H); 4.32 (dd, 1H); 4.95 (m, 1H); 6.95 (td, 1H); 7.32 (d, 1H); 7.43 (t, 1H); 7.51 (d, 1H).

Intermediate 2: Acetic acid (5R)-3-(3-fluoro-4-iodo-phenyl)-2-oxo-oxazolidin-5-ylmethyl ester

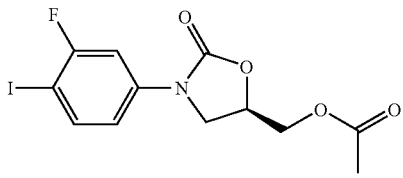

Acetic acid (5R)-3-(3-fluoro-phenyl)-2-oxo-oxazolidin-5-ylmethyl ester (Intermediate 1, 15.2 g, 60 mmol) was dissolved in a mixture of chloroform (100 ml) and acetonitrile (100 ml) under nitrogen, and silver trifluoroacetate (16.96 g, 77 mmol) were added. Iodine (18.07 g, 71 mmol) was added in portions over 30 minutes to the vigorously stirred solution, and stirring continued at ambient temperature for 18 hours. As reaction was not complete, a further portion of silver trifluoroacetate (2.64 g, 12 mmol) was added and stirring continued for 18 hours. After filtration, the mixture was added to sodium thiosulfate solution (3%, 200 ml) and dichloromethane (200 ml), and the organic phase separated, washed with sodium thiosulfate (200 ml), saturated aqueous sodium bicarbonate (200 ml), brine (200 ml), dried (magnesium sulfate), filtered and evaporated. The crude product was suspended in isohexane (100 ml), and sufficient diethyl ether added to dissolve out the brown impurity while stirring for 1 hour. Filtration gave the desired product (24.3 g) as a cream solid.

MS (ESP): 380 (MH$^+$) for $C_{12}H_{11}FINO_4$

NMR(300 MHz) (DMSO-d$_6$) δ: 2.03 (s, 3H); 3.82 (dd, 1H); 4.15 (t, 1H); 4.24 (dd, 1H); 4.30 (dd, 1H); 4.94 (m, 1H); 7.19 (dd, 1H); 7.55 (dd, 1H); 7.84 (t, 1H).

Intermediate 3: (5R)-3-(3-Fluoro-4-iodophenyl)-5-hydroxymethyloxazolidin-2-one

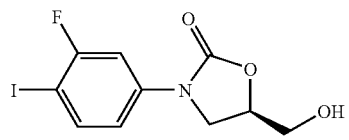

Acetic acid (5R)-3-(3-fluoro-4-iodophenyl)-2-oxo-oxazolidin-5-ylmethyl ester (Intermediate 2, 30 g, 79 mmol) was treated with potassium carbonate (16.4 g, 0.119 mmol) in a mixture of methanol (800 ml) and dichloromethane (240 ml) at ambient temperature for 25 minutes, then immediately neutralised by the addition of acetic acid (10 ml) and water (500 ml). The precipitate was filtered, washed with water, and dissolved in dichloromethane (1.2 L), the solution washed with saturated sodium bicarbonate, and dried (magnesium sulfate). Filtration and evaporation gave the desired product (23 g).

MS (ESP): 338 (MH$^+$) for $C_{10}H_9FINO_3$

NMR (300 MHz)(DMSO-d$_6$) δ: 3.53 (m, 1H); 3.67 (m, 1H); 3.82 (dd, 1H); 4.07 (t, 1H); 4.70 (m, 1H); 5.20 (t, 1H); 7.21 (dd, 1H); 7.57 (dd, 1H); 7.81 (t, 1H).

Intermediate 4: [(5R)-3-(3-Fluoro-4-iodophenyl)-2-oxo-1,3-oxazolidin-5-yl]methyl methanesulfonate

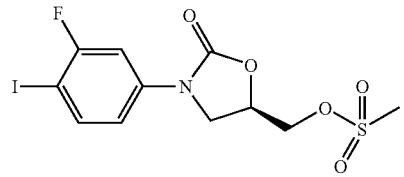

(5R)-3-(3-Fluoro-4-iodophenyl)-5-(hydroxymethyl)-1,3-oxazolidin-2-one (Intermediate 3, 25.0 g, 74.2 mmol) was stirred in dichloromethane (250 ml) at 0° C. Triethylamine (10.5 g, 104 mmol) was added followed by methanesulfonyl chloride (11.2 g, 89.0 mmol) and the reaction was stirred overnight, slowly warming to room temperature. The yellow solution was diluted with sodium bicarbonate and the compound was extracted using dichloromethane (3×250 ml). The organic layer was dried (magnesium sulfate), filtered and concentrated to give the desired product as a light yellow solid (30.3 g).

MS (ESP): 416 (MH$^+$) for $C_{11}H_{11}FINO_5S$ $^1$H-NMR (300 MHz) (DMSO-d$_6$): 3.24 (s, 3H); 3.82 (dd, 1H); 4.17 (t, 1H); 4.43–4.52 (m, 2H); 4.99–5.03 (m, 1H); 7.21 (dd, 1H); 7.55 (dd, 1H); 7.83 (t, 1H).

Intermediate 5: (5R)-5-(Azidomethyl)-3-(3-fluoro-4-iodophenyl)-1,3-oxazolidin-2-one

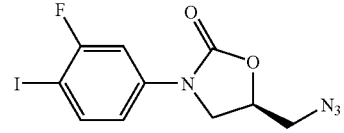

[(5R)-3-(3-Fluoro-4-iodophenyl)-2-oxo-1,3-oxazolidin-5-yl]methyl methanesulfonate (Intermediate 4, 6.14 g, 14.7 mmol) was dissolved in N,N-dimethylformamide (50 ml). Sodium azide (1.92 g, 29.6 mmol) was added and the reaction was stirred at 75° C. overnight. The yellow mixture was poured into half-saturated sodium bicarbonate and extracted using ethyl acetate. The organic layer was washed three times with water, dried (magnesium sulfate), filtered, and concentrated to give the title compound as a yellow solid (4.72 g).

MS (ESP): 363 (MH+) for $C_{10}H_8FIN_4O_2$
$^1$H-NMR(300 MHz) (DMSO-$d_6$): 3.72–3.82 (m, 3H); 4.14 (t, 1H); 4.89–4.94 (m, 1H); 7.22 (dd, 1H); 7.57 (dd, 1H); 7.83 (t, 1H).

Intermediate 6: (5R)-3-(3-Fluoro-4-iodophenyl)-5-(1H-1,2,3-triazol-1-ylmethyl)-1,3-oxazolidin-2-one

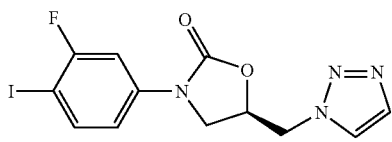

(5R)-5-(Azidomethyl)-3-(3-fluoro-4-iodophenyl)-1,3-oxazolidin-2-one (Intermediate 5, 30.3 g, 72.9 mmol) was stirred in 1,4-dioxane. Bicyclo[2.2.1]hepta-2,5-diene (40.3 g, 437 mmol) was added and the reaction was heated at 100° C. overnight. The resulting brown mixture was filtered and the desired product was obtained as a light brown solid (14.8 g).

MS (ESP): 389 (MH+) for $C_{12}H_{10}FIN_4O_2$
$^1$H-NMR(300 Mz) (DMSO-$d_6$: 3.90 (dd, 1H); 4.23 (t, 1H); 4.84 (d, 2H); 5.11–5.18 (m, 1H), 7.14 (dd, 1H); 7.49 (dd, 1H); 7.76 (s, 1H); 7.82 (t, 1H); 8.17 (s, 1H).

Intermediate 7: (5R)-3-[3-Fluoro-4-(4,4,5,5-tetramethyl-1,3,2-dioxaborolan-2-yl)phenyl]-5-(1H-1,2,3-triazol-1-ylmethyl)-1,3-oxazolidin-2-one

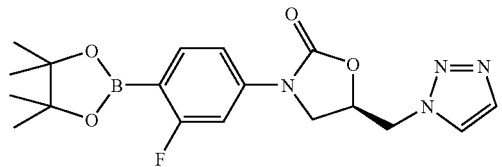

(5R)-3-(3-Fluoro-4-iodophenyl)-5-(1H-1,2,3-triazol-1-ylmethyl)-1,3-oxazolidin-2-one (Intermediate 6, 2 g, 5.15 mmol), bis(pinacolato)diboron, 2.62 g (10.3 mmol), potassium acetate, 2.5 g (25.5 mmol), and 1,1'-[bis(diphenylphosphino)ferrocene]dichloropalladium(II) dichoromethane complex, 0.38 g (0.52 mmol) were suspended in DMSO, 15 ml. The mixture was heated at 80° C. for 40 minutes to give a clear black solution. Ethyl acetate (150 ml) was then added and the mixture was filtered through celite, washed with saturated NaCl (2×100 ml), dried over sodium sulfate and evaporated. The dark residue was purified by chromatography (silica gel, 40 to 100% ethyl acetate in hexane, followed by 1–5% acetonitrile in ethyl acetate) to give the product as a crystalline tan solid, 1.97 g (98%). (note—highly colored impurities elute ahead of product band, extended elution required to obtain product).

NMR(300 MHz) (DMSO-$d_6$) δ: 1.28 (s, 12H), 3.91 (dd, 1H); 4.23 (t, 1H); 4.83 (d, 2H); 5.14 (m, 1H); 7.27 (dd, 1H); 7.37 (dd, 1H); 7.62 (t, 1H); 7.75 (s, 1H); 8.16 (s, 1H).

Alternatively:

(5R)-3-(3-Fluoro-4-iodophenyl)-5-(1H-1,2,3-triazol-1-ylmethyl)-1,3-oxazolidin-2-one (Intermediate 6, 5 g, 12.9 mmol), pinacolborane, 2.9 ml (20 mmol), triethylamine, 5.4 ml (39 mmol), and trans-dichlorobis(triphenylphosphine) palladium (II), 0.92 g (1.3 mmol) were dissolved in dioxane, 70 ml. The mixture was heated at 100° C. for 90 minutes to give a black solution, which was concentrated, dissolved in ethyl acetate, washed with brine, dried over sodium sulfate and evaporated. The residue was purified by chromatography (silica gel, 0 to 5% methanol in dichloromethane with 1% triethylamine) to give the product as a light brown solid, 3.1 g.

Intermediate 8: 5-Bromo-N-hydroxypyridine-2-carboximidoyl chloride

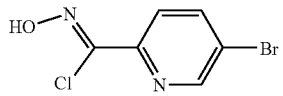

5-Bromopyridine-2-carbaldehyde oxime (49.5 g, 246.3 mmol) was dissolved in DMF (150 ml) followed by addition of N-chlorosuccinimide (39.5 g, 295.5 mmol). HCl gas was then bubbled in the solution for 20 seconds to initiate the reaction, which was then allowed to stir for 1 hr. The reaction was poured into distilled water (1 L) and the precipitate was collected by vacuum filtration. The filter cake was washed with distilled water (2×500 ml) and then dried overnight in a vacuum oven at 60° C. (–30 inches Hg) to yield the product as a white powder (55 g).

$^1$H-NMR(300 MHz)(CDCl$_3$): 7.73 (d, 1H); 8.09 (d, 1H); 8.73 (s, 1H); 12.74 (s, 1H).

NOTE: Lachrymator.

Intermediate 8a: 5-Bromopyridine-2-carbaldehyde oxime

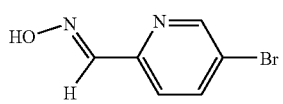

5-Bromo-pyridine-2-carbaldehyde (X. Wang et al, Tetrahedron Letters 41 (2000), 4335–4338) (60 g, 322 mmol) was added to methanol (700 ml) and then water was added (700 ml) followed by addition of hydroxylamine hydrochloride (28 g, 403 mmol). Sodium carbonate (20.5 g, 193.2 mmol) in water (200 ml) was added and the reaction was stirred for 30 minutes. Water (500 ml) was then added and the precipitate was filtered and washed with water (2×300 ml) to give the desired product (60 g).

NMR (DMSO-$d_6$)δ: 7.75 (d, 1H); 8.09 (t, 2H), 8.72 (s, 1H); 11.84 (s, 1H).

Intermediate 9: [3-(5-Bromopyridin-2-yl)-4,5-dihydroisoxazol-5-yl]methyl butyrate

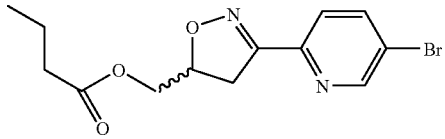

5-Bromo-N-hydroxypyridine-2-carboximidoyl chloride (Intermediate 8, 46 g, 195.7 mmol) was added to EtOAc (200 ml) followed by addition of alkyl butyrate (145 ml, 1020.4 mmol) and the solution was cooled to 0° C. Triethylamine (30 ml, 215.8 mmol) in EtOAc (100 ml) was then added dropwise over 1 hour. The reaction was then allowed to stir for 1 hour at 0° C. and then EtOAc (1 L) was added. The precipitate was removed by vacuum filtration and the filtrate was concentrated in vacuo to yield the product (65 g).

$^1$H-NMR(DMSO-$d_6$) δ: 0.81 (t, 3H); 1.43 (m, 2H); 2.24 (t, 2H); 3.21 (dd, 1H); 3.54 (dd, 1H); 4.13 (dd, 1H); 4.23 (dd, 1H); 5.01 (m,1H); 7.85 (dd, 1H); 8.12 (dd, 1H); 8.81 (d, 1H).

Intermediate 10: (5S)-3-(5-Bromopyridin-2-yl)-4,5-dihydroisoxazol-5-yl]methyl butyrate

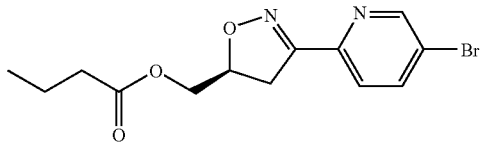

(+) Isomer assigned as (5S) based on comparison with Chem. Lett. 1993 p. 1847.

Racemic [3-(5-bromopyridin-2-yl)-4,5-dihydroisoxazol-5-yl]methyl butyrate (Intermediate 9, 80 g, 0.244 mol) was dissolved in acetone (4 L), and 0.1 M potassium phosphate buffer (pH~7) (4 L) was added with vigorous stirring to give a clear yellow solution. PS-lipase (1.45 g, Sigma cat no L-9156) was added and the mixture was gently stirred at ambient temp. for 42 hrs. The solution was divided into 3 equal volumes of ~2.6 L and each was extracted with dichloromethane (2×1 L), the pooled organic phases were dried over sodium sulfate and evaporated. The unreacted [(5S)-3-(5-bromopyridin-2-yl)-4,5-dihydroisoxazol-5-yl]methyl butyrate was isolated via flash column chromatography (9:1 hexane:ethyl acetate) as a clear yellow oil, 36.4 g (45.5%).

Intermediate 11: [(5S)-3-(5-Bromopyridin-2-yl)-4,5-dihydroisoxazol-5-yl]methanol

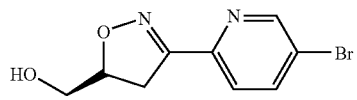

[(5S)-3-(5-Bromopyridin-2-yl)-4,5-dihydroisoxazol-5-yl]methyl butyrate (Intermediate 10, 16.88 g, 0.051 mol) was dissolved in methanol (110 ml). 50% Aqueous sodium hydroxide (3.6 ml, 0.068 mol) was added. The solution was stirred at RT for 15 minutes, 1M HCl (75 ml) was added, followed by concentration in vacuo to ~100 ml total volume. Water (~50 ml) was added, and the white precipitate was collected and rinsed with water. The filtrate was extracted twice with ethyl acetate, the organic layers were pooled, dried over sodium sulfate and evaporated. The solid residue was collected and rinsed with 10:1 hexane:ethyl acetate, then combined with the initial precipitate before drying in vacuo to give the title compound as a white crystalline solid, 12.3 g (93%). Chiral HPLC analysis indicated <0.5% of the (−) isomer was present. $[\alpha]_D$=+139 (c=0.01 g/ml in methanol).

Example 2

(5R)-3-(3-Fluoro-4-{6-[(5R)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one

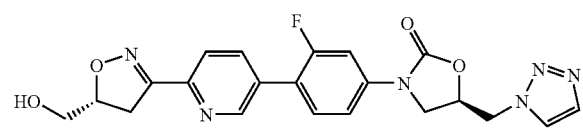

[(5R)-3-(5-Bromopyridin-2-yl)-4,5-dihydroisoxazol-5-yl]methanol (intermediate 12, 0.139 g, 0.54 mmol), (5R)-3-[3-fluoro-4-(4,4,5,5-tetramethyl-1,3,2-dioxaborolan-2-yl)phenyl]-5-(1H-1,2,3-triazol-1-ylmethyl)-1,3-oxazolidin-2-one (Intermediate 7, 0.2 g, 0.514 mmol), potassium carbonate (0.355 g, 2.57 mmol), and tetrakis(triphenylphosphino)palladium(0) (0.059 g, 0.05 mmol) were combined and suspended in DMF (7 ml) and water (1 ml). The mixture was heated at 75° C. for 2 hours, then was poured into cold water (30 ml). The solids formed were collected, rinsed with water and washed with dichloromethane (2×10 ml), the solids were further purified by column chromatography, eluted with 5% DMF in dichloromethane to give the title compound as a white solid (0.125 g).

MS (ESP): 439.22 (M+1) for $C_{21}H_{19}FN_6O_4$ $^1$H-NMR(300 MHz)(DMSO-d$_6$) δ: 3.36–3.58 (m, 4H); 3.95 (dd, 1H); 4.29 (t, 1H); 4.78 (m, 1H); 4.86 (d, 2H); 5.02 (t, 1H); 5.18 (m, 1H); 7.41 (dd, 1H); 7.58 (dd, 1H); 7.69 (t, 1H); 7.77 (s, 1H); 7.98 (d, 1H); 8.05 (dd, 1H); 8.18 (s, 1H); 8.78 (s, 1H).

Intermediate 12: [(5R)-3-(5-bromopyridin-2-yl)-4,5-dihydroisoxazol-5-yl]methanol

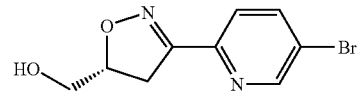

(R,S)-[3-(5-Bromopyridin-2-yl)-4,5-dihydroisoxazol-5-yl]methanol (prepared by hydrolysis of Intermediate 9, 3.1 g) was dissolved in hot methanol (25 ml), it was then separated by chiral column (Chiral Pak AS) eluting with 30%, isopropanol in hexanes. The title compound [(−) isomer, 1.5 g)] which eluted first from the column was collected along with the (+) isomer (second peak, 1.18 g). Chiral HPLC analysis indicated <2% of the (+) isomer was present. $[\alpha]_D$=−125° (c=0.0076 g/ml in methanol).

Example 3

N-{[(5S)-3-(3-Fluoro-4-{6-[(5S)-5-(hydroxymethyl)-4,5-dihydroisoxazol-3-yl]pyridin-3-yl}phenyl)-2-oxo-1,3-oxazolidin-5-yl]methyl}acetamide

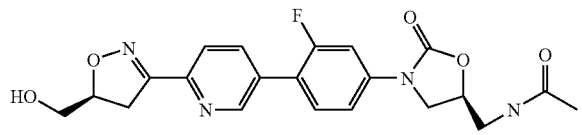

[(5S)-3-(5-Bromopyridin-2-yl)-4,5-dihydroisoxazol-5-yl]methanol (Intermediate 11, 0.5 g, 1.95 mmol), potassium carbonate (0.622 g, 4.5 mmol), N-({(5S)-3-[3-fluoro-4-(4,4,5,5-tetramethyl-1,3,2-dioxaborolan-2-yl)phenyl]-2-oxo-1,3-oxazolidin-5-yl}methyl)acetamide (Intermediate 13, 0.736 g, 1.95 mmol) and tetrakis(triphenylphosphino)palladium(0) (0.225 g, 0.195 mmol) were combined and suspended in DMF (7 ml) and water (1 ml). The mixture was heated at 75° C. for 2 hours, then was poured into cold water (30 ml). The solids formed were collected, rinsed with water and washed with dichloromethane, dried under vaccuum and collected to give the title compound (0.407 g).

MS (ESP): 429.31 (M+1) for $C_{21}H_{21}FN_4O_5$

NMR(300 Mz)(DMSO-d$_6$) δ: 1.82 (s, 3H); 3.3 (m, 2H); 3.41 (m, 2H); 3.55 (m, 2H); 3.80 (dd, 1H); 4.21 (t, 1H); 4.78 (m, 2H); 5.02 (t, 1H); 7.43 (dd, 1H); 7.61 (dd, 1H); 7.69 (t, 1H); 7.98 (d, 1H); 8.05 (dd, 1H); 8.21 (t, 1H); 8.78 (s, 1H).

The starting materials for Example 3 were made as follows:

Intermediate 13: N-({(5S)-3-[3-Fluoro-4-(4,4,5,5-tetramethyl-1,3,2-dioxaborolan-2-yl)phenyl]-2-oxo-1,3-oxazolidin-5-yl}methyl)acetamide

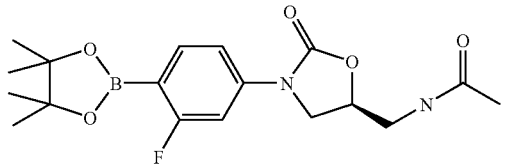

N-{[(5S)-3-(3-Fluoro-4-iodophenyl)-2-oxo-1,3-oxazolidin-5-yl]methyl}acetamide (Intermediate 14, 1.0 g, 2.65 mmol), bis(pinacolato)diboron (1.68 g, 6.6 mmol), potassium acetate (0.9 g, 9.27 mmol), and 1,1'-[bis(diphenylphosphino)ferrocene]dichloropalladium(II) dichoromethane complex (0.194 g, 0.265 mmol) were suspended in DMSO (10 ml). The mixture was heated at 80° C. for 90 minutes to give a clear black solution. After cooling down to room temperature, ethyl acetate (150 ml) was added and the mixture was filtered through celite, washed with saturated NaCl (2×100 ml), dried over sodium sulfate and concentrated to dryness. The dark residue was dissolved in dichloromethane (5 ml), followed by slow addition of hexanes (20 ml), the resulting precipitate was filtered and washed with 5% dichloromethane in hexanes and collected as the desired product (0.99 g) which was used directly as an intermediate without further purification.

Intermediate 14: N-{[(5S)-3-(3-Fluoro-4-iodophenyl)-2-oxo-1,3-oxazolidin-5-yl]methyl}acetamide

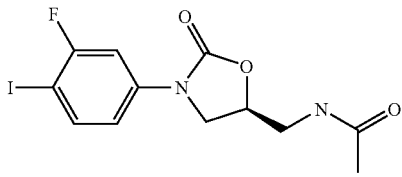

(5R)-5-(Azidomethyl)-3-(3-fluoro-4-iodophenyl)-1,3-oxazolidin-2-one (Intermediate 5, 5.00 g, 0.014 mol) was suspended in thioacetic acid (10 ml) and the solution was stirred under nitrogen at room temperature for ca. 16 h. The resulting suspension was concentrated under vacuum. The crude product was crystallized from methanol/acetone, then further purified by chromatography on silica gel using dichloromethane to give 3.71 g of the title product as a white solid.

MS (ESP): 379 (MH$^+$) for $C_{12}H_{12}FIN_2O_3$ $^1$H-NMR(500 MHz) (DMSO-d$_6$): 1.86 (s, 3H); 3.45 (t, 2H); 3.76 (dd, 1H); 4.14 (t, 1H); 4.78 (m, 1H); 7.22 (dd, 1H); 7.58 (dd, 1H); 7.87 (t, 1H); 8.28 (t, 1H).

Example 4

N-{[(5S)-3-(3-Fluoro-4-{6-[(5R)-5-(hydroxymethyl)-4,5-dihydroisoxazol-3-yl]pyridin-3-yl}phenyl)-2-oxo-1,3-oxazolidin-5-yl]methyl}acetamide

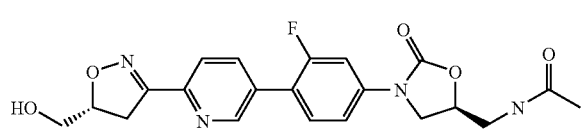

[(5R)-3-(5-Bromopyridin-2-yl)-4,5-dihydroisoxazol-5-yl]methanol (Intermediate 12, 0.5 g, 1.95 mmol), (0.35 g, 0.9 mmol), potassium carbonate (0.622 g, 4.5 mmol), N-({(5S)-3-[3-fluoro-4-(4,4,5,5-tetramethyl-1,3,2-dioxaborolan-2-yl)phenyl]-2-oxo-1,3-oxazolidin-5-yl}methyl)acetamide (Intermediate 13, 0.736 g, 1.95 mmol) and tetrakis(triphenylphosphino)palladium(0) (0.225 g, 0.195 mmol) were combined and suspended in DMF (7 ml) and water (1 ml). The mixture was heated at 75° C. for 2 hours, then was poured into cold water (30 ml). The solids formed were collected, rinsed with water and washed with dichloromethane, dried under vaccum and collected as the title compound (0.42 g)

MS (ESP): 429.31 (M+1) for $C_{21}H_{21}FN_4O_5$ $^1$H-NMR(300 Mz)(DMSO-d$_6$) δ: 1.82 (s, 3H); 3.3 (m, 2H); 3.41 (m, 2H); 3.55 (m, 2H); 3.80 (dd, 1H); 4.21 (t, 1H); 4.78 (m, 2H); 5.02 (t, 1H); 7.43 (dd, 1H); 7.61 (dd, 1H); 7.69 (t, 1H); 7.98 (d, 1H); 8.05 (dd, 1H); 8.21 (t, 1H); 8.78 (s, 1H).

Example 5

(5R)-3-(3-Fluoro-4-{6-[(5S)-5-(hydroxymethyl)-4,5-dihydroisoxazol-3-yl]pyridin-3-yl}phenyl)-5-{[4-(fluoromethyl)-1H-1,2,3-triazol-1-yl]methyl}-1,3-oxazolidin-2-one

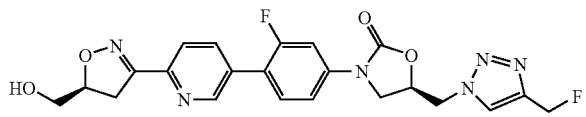

[(5S)-3-(5-Bromopyridin-2-yl)-4,5-dihydroisoxazol-5-yl]methanol (Intermediate 11, 1.075 g, 4.18 mmol), (5R)-5-{[4-(fluoromethyl)-1H-1,2,3-triazol-1-yl]methyl}-3-[3-f -(4,4,5,5-tetramethyl-1,3,2-dioxaborolan-2-yl)phenyl]-1,3-oxazolidin-2-one (Intermediate 15, 1.6 g, 3.80 mmol), potassium carbonate (2.6 g, 19 mmol), and tetrakis(triphenylphosphino)palladium(0) (0.44 g, 0.38 mmol) were suspended in DMF (25 ml) and water (2.5 ml). The mixture was heated at 80° C. for 2 hours, then was poured into cold water (100 ml). The solids formed were collected, rinsed with water and washed with dichloromethane (2×10 ml), then dissolved in warm trifluoroethanol (6 ml), and purified by column chromatography, eluting with 8% methanol in dichloromethane to give the title compound as a white solid (1.36 g).

MS (ESP): 471.15 (M+1) for $C_{22}H_{20}F_2N_6O_4$

NMR(300 Mz) (DMSO-d$_6$) δ: 3.40 (m, 2H); 3.53 (m, 2H); 3.95 (dd, 1H); 4.29 (t, 1(m, 1H); 4.86 (d, 2H); 5.02 (t, 1H); 5.18 (m, 1H); 5.50 (d, 2H); 7.41 (dd, 1H 7.69 (t, 1H); 8.0 (overlapping m, 2H); 8.41 (s, br, 1H); 8.85 (s, 1H).

The starting material for Example 5 was made as follows:

Intermediate 15: (5R)-5-{[4-(Fluoromethyl)-1H-1,2,3-triazol-1-yl]methyl}-3-[3-flouro-4-(4,4,5,5-tetramethyl-1,3,2-dioxaborolan-2-yl)phenyl]-1,3-oxazolidin-2-one

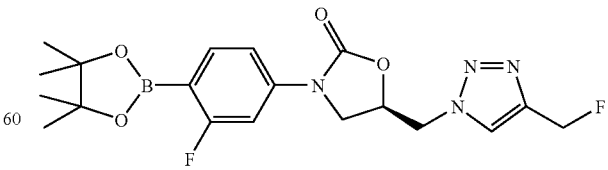

(5R)-3-(3-Fluoro-4-iodophenyl)-5-{[4-(fluoromethyl)-1H-1,2,3-triazol-1-yl]methyl}1,3-oxazolidin-2-one (Intermediate 16, 4.0 g, 9.5 mmol), bis(pinacolato)diboron (6.0 g, 23.75 mmol), potassium acetate (3.24 g, 33.25 mmol), and 1,1'-[bis(diphenylphosphino)ferrocene]dichloropalladium (II) dichoromethane complex (0.695 g, 0.95 mmol) were suspended in DMSO (25 ml). The mixture was heated at 80° C. for 90 minutes to give a clear black solution. After cooling down to room temperature, ethyl acetate (250 ml) was then added and the mixture was filtered through celite, washed with saturated NaCl (2×100 ml), dried over sodium sulfate and concentrated to dryness. The dark residue was dissolved in dichloromethane (30 ml), followed by slow addition of hexanes (100 ml), the resulting precipitate was filtered and washed with 5% dichloromethane in hexanes to give the desired product (2.73 g) which was used directly as an intermediate without further purification.

Intermediate 16: (5R)-3-(3-Fluoro-4-iodophenyl)-5-[(4-fluoromethyl-1H-1,2,3-triazol -1-yl)methyl]oxazolidin-2-one

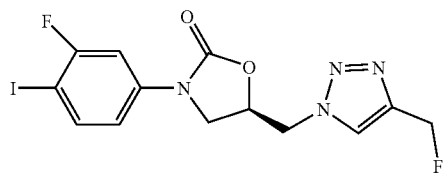

(5R)-3-(3-Fluoro-4-iodophenyl)-5-[(4-bromomethyl-1H-1,2,3-triazol-1-yl)methyl]oxazolidin-2-one (Intermediate 17, 6.94 g, 14.4 mmol) was dissolved/suspended in acetonitrile (250 mL) and water (1.5 mL). Potassium fluoride (4.19 g, 72.1 mmol) was added, followed by addition of 1-butyl-3-methylimidazolium tetrafluoroborate (18.4 mL) and the solution was heated to 90° C. over night. It was diluted with ethyl acetate, washed with water and dried over magnesium sulfate. Chromatography on silica gel with ethyl acetate gave 2.7 g (45%) of the title compound as an off-white solid.

MS (ESP): 421.34 (MH$^+$) for $C_{13}H_{11}F_2IN_4O_2$ $^1$H-NMR (DMSO-d$_6$) δ: 3.88 (dd, 1H); 4.23 (dd, 1H); 4.84 (m, 2H); 5.14 (m, 1H); 5.45 (d, 2H, J$_{H,F}$ 52 Hz); 7.14 (m, 1H); 7.49 (m, 1H); 7.81 (m, 1H); 8.34 (d, 1H).

Intermediate 17: (5R)-3-(3-Fluoro-4-iodophenyl)-5-[(4-bromomethyl-1H-1,2,3-triazol-1-yl)methyl]oxazolidin-2-one

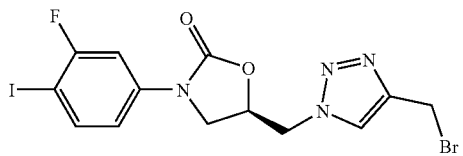

5R)-3-(3-Fluoro-4-iodophenyl)-5-[(4-hydroxymethyl-1H-1,2,3-triazol-1-yl)methyl]oxazolidin-2-one (Intermediate 18, 14.7 g, 35.1 mmol) was suspended in dichloromethane (1 L). Carbon tetra bromide (12.16 g, 36.7 mmol) was added, it was cooled to 0° C. and triphenylphosphine (12.34 g, 61.2 mmol) was added. The mixture was stirred for 30 minutes at 0° C. and then at room temperature over night. For workup the reaction mixture was applied onto a silica gel column and eluted with hexanes/ethyl acetate (1:1) and then with ethyl acetate/methanol (95:5). Fractions containing product were pooled and recrystallized from ethyl acetate to give 14 g of the title compound as a colorless solid.

MS (ESP): 482.69 (MH$^+$ for Br$^{81}$) for $C_{13}H_{11}BrFIN_4O_2$ $^1$H-NMR (DMSO-d$_6$) δ: 3.87 (dd, 1H); 4.23 (dd, 1H); 4.74 (s, 2H); 4.81 (m, 2H); 5.12 (m, 1H); 7.14 (m, 1H); 7.49 (m, 1H); 7.81 (m, 1H); 8.22 (d, 1H).

Intermediate 18: (5R)-3-(3-Fluoro-4-iodophenyl)-5-[(4-hydroxymethyl-1H-1,2,3-triazol-1-yl)methyl]oxazolidin-2-one

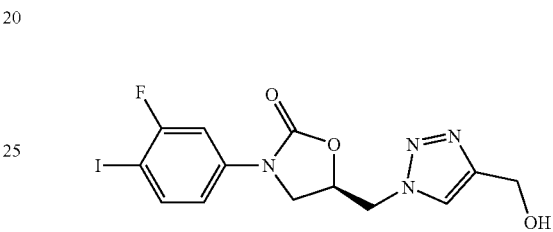

(5R)-5-(Azidomethyl)-3-(3-fluoro-4-iodophenyl)-1,3-oxazolidin-2-one (Intermediate 5, 10 g, 28 mmol) was dissolved in acetonitrile (80 mL). Propargyl alcohol (3.2 mL, 56 mmol) was added and then CuI (526 mg, 2.8 mmol) and it was stirred overnight. The solidified reaction mixture was extracted with ethyl acetate/acetonitrile, washed with water and dried over magnesium sulfate. Evaporation of solvent under vacuum gave 12.3 g crude product (quantitative).

MS (ESP): 419.13 (MH$^+$) for $C_{13}H_{12}FIN_4O_3$ $^1$HMR (DMSO-d$_6$) δ: 3.88 (dd, 1H); 4.23 (dd, 1H); 4.51 (d, 2H); 4.80 (m, 2H); 5.14 (m, 1H); 5.22 (dd, 1H); 7.16 (m, 1H); 7.51 (m, 1H); 7.83 (m, 1H); 8.01 (d, 1H).

Example 6

Ethyl [(5S)-3-(5-{2-fluoro-4-[(5R)-2-oxo-5-(1H-1,2,3-triazol-1-ylmethyl)-1,3oxazolidin-3-yl]phenyl}pyridin-2-yl)-4,5-dihydroisoxazol-5-yl]methyl hexanedioate

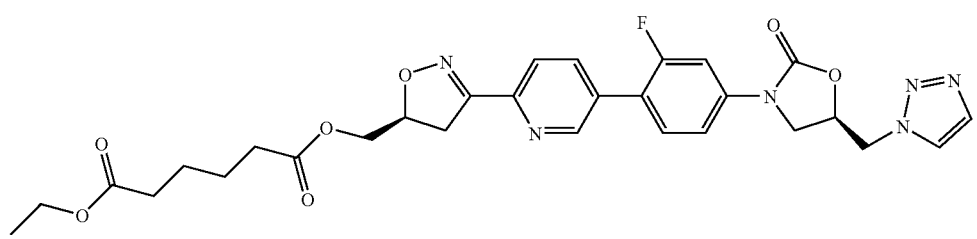

(5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1, 0.25 g, 0.57 mmol), adipic acid monoethyl ester (0.25 g, 1.44 mmol), 4-dimethylaminopyridine (0.02 g, 0.16 mmol), and 1-[3-(dimethylamino)propyl]-3-ethylcarbodiimide hydrochloride were combined in DMF (4 ml). The suspension was allowed to stir for one hour at room temperature resulting in a clear solution. The mixture was then diluted with ethyl acetate, washed with water, and dried over magnesium sulfate. The residue obtained upon filtration and evaporation was purified by chromatography (silica gel, 0.5 to 10% methanol in dichloromethane). Evaporation of the product containing fractions and trituration of the resulting solid with diethyl ether yielded the title compound as a white powder (0.275 g), melting point: 88° C.

MS (ESP): 595 (MH$^+$) for $C_{29}H_{31}FN_6O_7$ $^1$H-NMR (300 MHz)(DMSO-d$_6$) δ: 1.13 (t, 3H); 1.48 (m, 4H); 2.20 (bt, 2H); 2.31 (bt, 2H); 3.28 (m, 2H); 3.58 (dd, 1H); 3.96 (dd, 1H); 4.01 (q, 2H); 4.15 (dd, 1H); 4.25 (dd, 1H); 4.32 (d, 1H); 4.86 (d, 2H); 5.00 (m, 1H); 5.18 (m, 1H); 7.42 (dd, 1H); 7.58 (dd, 1H); 7.69 (t, 1H); 7.77 (s, 1H); 8.00 (d, 1H); 8.06 (d, 1H); 8.18 (s, 1H); 8.82 (s, 1H).

Example 6 is a non-limiting example of a suitable pro-drug for compounds of the invention, and is a suitable pro-drug of Example 1.

Example 7

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl nicotinate

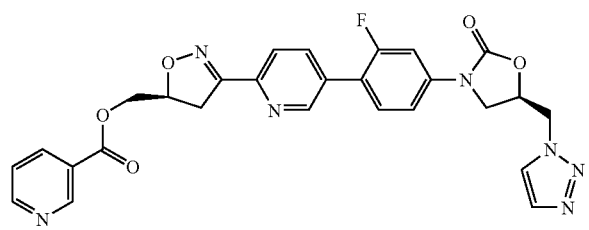

(5R)-3-(3-Fluoro {6-[(5S)-5-(hydroxymethyl)-4,5,-dihydroisoxazol-3-yl]pyridin-3-yl}phenyl)-4-(1H-1,2,3-triazol-1-ylmethyl)-1,3-oxazolidin-2-one (Example 1, 200 mg, 0.46 mM), nicotinoylchloride hydrochloride (175 mg, 0.98 mM), 4-(dimethylamino)pyridine (DMAP, 20 mg, 0.17 mM) were placed in a flask. Anhydrous dimethylformamide (2 mL) and anhydrous pyridine (2 mL) were added and the suspension was stirred for 16 hours during which it became a clear solution. 500 mg silicagel was added and the solvents were evaporated. The residue was chromatographed on silicagel eluting with a gradient of methanol in dichloromethane (1–20%) to give title compound (120 mg, 48%).

MS (APCI): 544 (M+1) for $C_{27}H_{22}N_7O_5F$

NMR (DMSO-d$_6$) δ: 3.51 (dd, 1H); 3.68 (dd, 1H); 3.95 (dd, 1H); 4.34 (t, 1H); 4.49 (dd, 1H); 4.55 (dd, 1H); 4.87 (d, 2H); 5.20 (m, 2H); 7.43 (dd, 1H); 7.65 (m, 2H); 7.71 (t, 1H); 7.78 (s, 1H); 8.02 (d, 1H); 8.08 (d, 1H); 8.20 (s, 1H); 8.32 (dd, 1H); 8.81 (m, 2H); 9.06 (s, 1H)

Example 7 is a non-limiting example of a suitable pro-drug for compounds of the invention, and is a suitable pro-drug of Example 1.

Example 8

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl β-alaninate

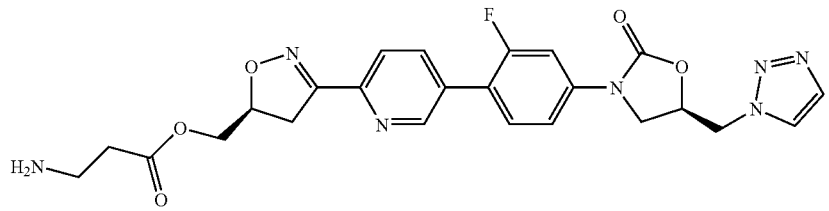

(5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1, 0.25 g, 0.57 mmol), N-(tert-butoxycarbonyl)-β-alanine (0.27 g, 1.43 mmol), 4-dimethylaminopyridine (0.02 g, 0.16 mmol), and 1-[3-(dimethylamino)propyl]-3-ethylcarbodiimide hydrochloride 0.25 g, 1.30 mmol) were combined in DMF (4 ml). The suspension was allowed to stir for one hour at room temperature resulting in a clear solution. The mixture was then diluted with ethyl acetate, washed with water, and dried over magnesium sulfate. The residue obtained upon filtration and evaporation was purified via chromatography (silica gel, 1% to methanol in dichloromethane). Evaporation of the product containing fractions and trituration of the resulting solid with hexane:dichloromethane (5:1) yielded the tert-butoxycarbonyl derivative of the title compound as a waxy off-white solid (0.34 g). This protected derivative was dissolved in methylene chloride (5 ml) and trifluoroacetic acid (10 ml) was added. The resulting light yellow solution was stirred at room temp. for 1 hour, then concentrated in vacuo. The residue was suspended in dioxane (20 ml), and treated with 4M HCl in dioxane (2 ml). The resulting thick suspension was stirred for 10 minutes, diluted with ether, and filtered to yield the hydrochloride salt of the title compound as a hygroscopic yellow solid (0.30 g), mp68–75° C.

MS(ESP): 510 (MH$^+$) for $C_{24}H_{24}FN_7O_5$ $^1$H-NMR(300 MHz, DMSO-d$_6$) δ: 2.59 (m, 2H); 2.69 (m, 2H); 2.98 (m, 3H); 3.30–3.40 (m, 1H); 3.62 (m, 1H); 3.95 (dd, 1H); 4.19 (dd, 1H); 4.30 (m, 1H); 4.86 (d, 2H); 5.04 (m,1H); 5.18 (m, 1H); 7.42 (d, 1H); 7.58 (d, 1H); 7.69 (t, 1H); 7.76 (s, 1H); 8.01 (d, 1H); 8.18 (s, 1H); 8.83 (s, 1H).

Example 8 is a non-limiting example of a suitable pro-drug for compounds of the invention, and is a suitable pro-drug of Example 1.

Example 9

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl 4-(dimethylamino)butanoate

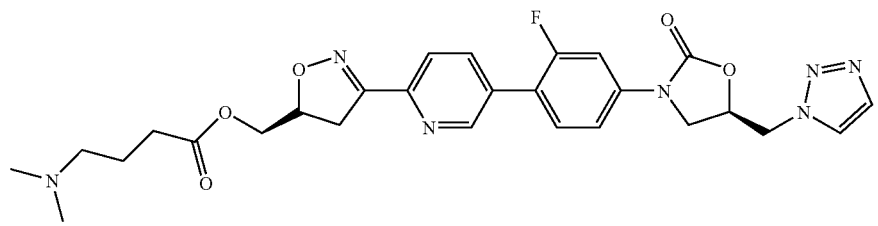

(5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1, 0.25 g, 0.57 mmol), 4-(dimethylamino)butanoic acid hydrochloride salt (0.24 g, 1.43 mmol), 4-dimethylaminopyridine (0.02 g, 0.16 mmol), and 1-[3-(dimethylamino)propyl]-3-ethylcarbodiimide hydrochloride (0.25 g, 1.30 mmol) were combined in DMF (4 ml), The suspension was allowed to stir for one hour at room temperature resulting in a clear solution. The mixture was then concentrated in vacuo, suspended in ethyl acetate:acetonitrile (1:1) and filtered. The solids were dissolved in a minimum amount of methanol and submitted directly to purification via chromatography (silica gel, 1 to 20% methanol in dichloromethane). Evaporation of the product containing fractions and trituration of the resulting solid with diethyl ether yielded the title compound as a white solid (0.195 g), melting point: 148° C.

MS (ESP): 552 (MH+) for $C_{27}H_{30}FN_7O_5$ $^1$H-NMR(300 MHz, DMSO-$d_6$) δ: 1.80 (m, 2H); 2.40 (t, 2H); 2.54 (s, 6H); 2.80 (m, 2H); 3.59 (dd, 1H); 3.96 (dd, 1H); 4.17 (dd, 1H); 4.30 (m, 2H); 4.86 (d, 2H); 5.02 (m, 1H); 5.18 (m, 1H); 7.42 (dd, 1H); 7.58 (dd, 1H); 7.69 (t, 1H); 7.77 (s, 1H); 8.00 (d, 1H); 8.07 (dd, 1H); 8.18 (s, 1H); 8.82 (s, 1H).

Example 9 is a non-limiting example of a suitable pro-drug for compounds of the invention, and is a suitable pro-drug of Example 1.

Example 10

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl 5-[(methoxycarbonyl)amino]pentanoate

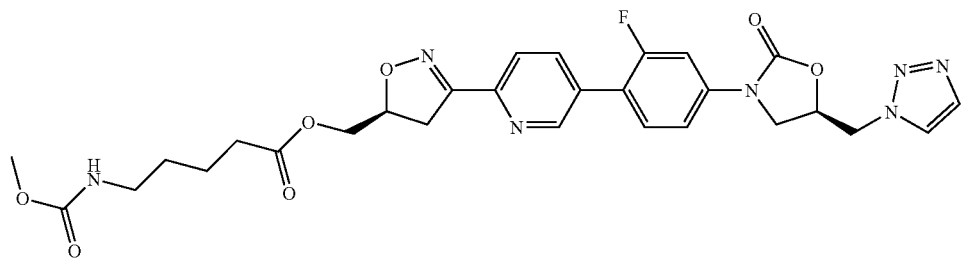

5-Aminopentanoic acid hydrochloride (2 g, 13 mmol), and potassium carbonate (13 g, 94 mmol) were dissolved in water (30 ml) and dioxane (10 ml) then cooled to 0° C. Methyl chloroformate (5 ml, 65 mmol) was added over 30 seconds, then the mixture was stirred for 2.5 hours at 0° C. Concentrated HCl was added until the mixture became acidic then the mixture was diluted with water and extracted with ether. The organic layer was dried over magnesium sulfate, evaporated and dried in vacuo to give 5-[(methoxycarbonyl)amino]pentanoic acid as a white powder (1.5 g).

The methyl carbamate prepared as above (0.25 g, 1.43 mmol), (5R)-3-(3-fluoro-4-{6-[(5S) -5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1, 0.25 g, 0.57 mmol), 4-dimethylaminopyridine (0.02 g, 0.16 mmol), and 1-[3-(dimethylamino)propyl]-3-ethylcarbodiimide hydrochloride (0.25 g, 1.30 mmol) were combined in DMF (4 ml). The suspension was allowed to stir for one hour at room temperature resulting in a clear solution. The mixture was then diluted with ethyl acetate, washed with water, and dried over magnesium sulfate. The residue obtained upon filtration and evaporation was purified via chromatography (silica gel, 0.5 to 10% methanol in dichloromethane). Evaporation of the product containing fractions and trituration of the resulting solid with diethyl ether yielded the title compound as a white powder (0.33 g), melting point: 90° C.

MS (ESP): 596 (MH$^+$) for $C_{28}H_{30}FN_7O_7$ $^1$H-NMR(300 MHz, DMSO-d$_6$) δ: 1.35 (m, 2H); 1.47 (m, 2H); 2.30 (t, 2H); 2.90 (m, 2H); 3.48 (s, 3H); 3.58 (dd, 1H); 3.95 (dd, 1H); 4.14 (dd, 1H); 4.29 (m, 2H); 4.86 (d, 2H); 5.01 (m, 1H); 5.19 (m, 1H); 7.07 (bt, 1H); 7.42 (dd, 1H); 7.58 (dd, 1H); 7.69 (t, 1H); 7.77 (s, 1H); 8.00 (d, 1H); 8.06 (dd, 1H); 8.18 (s, 1H); 8.82 (s, 1H).

Example 10 is a non-limiting example of a suitable pro-drug for compounds of the invention, and is a suitable pro-drug of Example 1.

Example 11

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl N,N-diethyl-β-alaninate

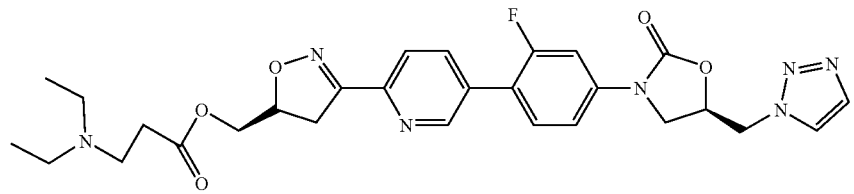

(5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1, 0.25 g, 0.57 mmol), N,N-diethyl-β-alanine hydrochloride (0.24 g, 1.43 mmol), 4-dimethylaminopyridine (0.02 g, 0.16 mmol), and 1-[3-(dimethylamino)propyl]-3-ethylcarbodiimide hydrochloride (0.25 g, 1.30 mmol) were combined in DMF (4 ml). The suspension was allowed to stir for one hour at room temperature. The mixture was then diluted with acetonitrile:ether (1:1) and filtered. The solids were dissolved in a minimum amount of methanol and purified by chromatography (silica gel, 5 to 20% methanol in dichloromethane). Evaporation of the product containing fractions and trituration of the resulting solid with diethyl ether yielded the title compound as a white solid (70 mg), melting point: 167° C.

MS (ESP): 566 (MH$^+$) for $C_{28}H_{32}FN_7O_5$ $^1$H-NMR(300 MHz, DMSO-d$_6$) δ: 1.13 (bt, 6H); 2.82 (bm, 2H); 3.08 (bm, 2H); 3.60 (dd, 1H); 3.96 (dd, 1H); 4.15–4.35 (m, 4H); 4.86 (d, 2H); 5.02 (m, 1H); 5.19 (m, 1H); 7.42 (dd, 1H); 7.58 (dd, 1H); 7.68 (t, 1H); 7.76 (s, 1H); 8.00 (d, 1H); 8.07 (d, 1H); 8.18 (s, 1H); 8.83 (s, 1H).

Example 11 is a non-limiting example of a suitable pro-drug for compounds of the invention, and is a suitable pro-drug of Example 1.

Example 12

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl methoxyacetate

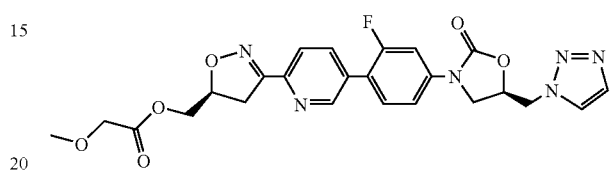

(5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1, 0.25 g, 0.57 mmol), methoxyacetic acid (0.15 ml, 1.96 mmol), 4-dimethylaminopyridine (0.02 g, 0.16 mmol), and 1-[3-(dimethylamino)propyl]-3-ethylcarbodiimide hydrochloride (0.25 g, 1.30 mmol) were combined in DMF (4 ml). The suspension was allowed to stir for one hour at room temperature resulting in a clear solution. The mixture was then diluted with ethyl acetate, washed with water, and dried over magnesium sulfate. The residue obtained upon filtration and evaporation was purified via chromatography (silica gel, 0.5 to 5% methanol in dichloromethane). Evaporation of the product containing fractions and trituration of the resulting solid with diethyl ether yielded the title compound as a white solid (0.25 g), melting point: 170° C.

MS (ESP): 511 (MH$^+$) for $C_{24}H_{23}FN_6O_6$ $^1$H-NMR(300 MHz, DMSO-d$_6$) δ: 3.29 (s, 3H); 3.60 (dd, 1H); 3.96 (dd, 1H); 4.06 (s, 2H); 4.19–4.35 (m, 4H); 4.86 (d, 2H); 5.02 (m, 1H); 5.18 (m, 1H); 7.42 (dd, 1H); 7.58 (dd, 1H); 7.69 (t, 1H); 7.77 (s, 1H); 7.99 (d, 1H); 8.07 (bd, 1H); 8.18 (s, 1H); 8.82 (s, 1H).

Example 12 is a non-limiting example of a suitable pro-drug for compounds of the invention, and is a suitable pro-drug of Example 1.

Example 13

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl 3-methoxypropanoate

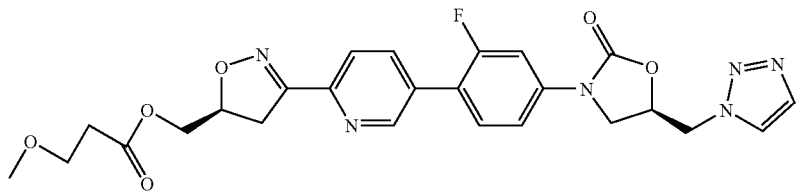

(5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1, 0.25 g, 0.57 mmol), 3-methoxypropionic acid (0.15 ml, 1.6 mmol), 4-dimethylaminopyridine (0.02 g, 0.16 mmol), and 1-[3-(dimethylamino)propyl]-3-ethylcarbodiimide hydrochloride (0.25 g, 1.30 mmol) were combined in DMF (4 ml). The suspension was allowed to stir for one hour at room temperature resulting in a clear solution. The mixture was then diluted with ethyl acetate, washed with water, and dried over magnesium sulfate. The residue obtained upon filtration and evaporation was purified via chromatography (silica gel, 0.5 to 5% methanol in dichloromethane). Evaporation of the product containing fractions and trituration of the resulting solid with diethyl ether yielded the title compound as a white solid (0.255 g), melting point: 149° C.

MS (ESP): 525 (MH$^+$) for $C_{25}H_{25}FN_6O_6$ $^1$H-NMR(300 MHz, DMSO-$d_6$) δ: 2.53 (t, 2H); 3.14 (s, 3H); 3.49 (t, 2H); 3.58 (dd, (dd, 1H); 4.15–4.33 (m, 4H); 4.86 (d, 2H); 5.00 (m, 1H); 5.18 (m, 1H); 7.42 (dd, 1H); 7.58 (dd, 1H); 7.69 (t, 1H); 7.77 (s, 1H); 7.99 (d, 1H); 8.07 (bd, 1H); 8.18 (s, 1H); 8.82 (s, 1H).

Example 13 is a non-limiting example of a suitable pro-drug for compounds of the invention, and is a suitable pro-drug of Example 1.

Example 14

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl methyl carbonate

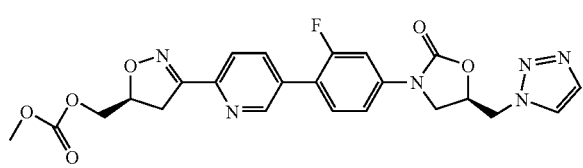

(5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1, 0.2 g, 0.46 mmol) was dissolved in DMF (4 ml) and pyridine (1 ml), then cooled to 0° C. Methyl chloroformate (0.2 ml, 2.57 mmol) was added and the mixture was stirred for 45 minutes at 0° C. A further portion of methyl chloroformate was added (0.2 ml), and the mixture was stirred for a further 2 hours 15 minutes before addition of a third portion of methyl chloroformate (0.2 ml). The mixture was stirred for a further hour at 0° C. after the third chloroformate addition, then diluted with water, extracted twice with ethyl acetate and dried over sodium sulfate. The residue obtained upon filtration and evaporation was purified via chromatography (silica gel, 0 to 10% acetonitrile in ethyl acetate). Evaporation of the fractions containing product and trituration of the resulting solid with diethyl ether yielded the title compound as a white solid (0.125 g), melting point: 205° C.

MS (ESP): 497 (MH$^+$) for $C_{23}H_{21}FN_6O_6$ $^1$H-NMR(300 MHz, DMSO-$d_6$) δ: 3.59 (dd, 1H); 3.70 (s, 3H); 3.96 (dd, 1H); 4.22 (dd, 1H); 4.28–4.33 (m, 2H); 4.86 (d, 2H); 5.02 (m, 1H); 5.19 (m, 1H); 7.42 (dd, 1H); 7.59 (dd, 1H); 7.69 (t, 1H); 7.77 (s, 1H); 8.00 (d, 1H); 8.06 (d, 1H); 8.18 (s, 1H); 8.83 (s, 1H).

Example 14 is a non-limiting example of a suitable pro-drug for compounds of the invention, and is a suitable pro-drug of Example 1.

Example 15

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl 2-methoxyethyl carbonate

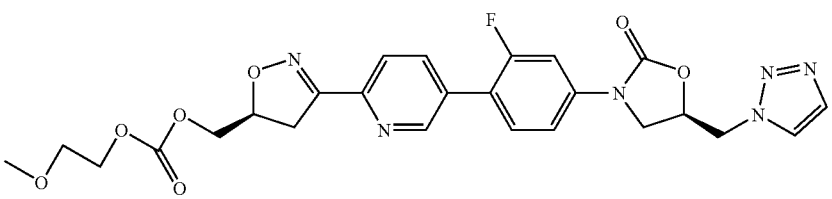

(5R)-3-(3-Fluoro-4-{6-[(5S)-5-hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1, 0.2 g, 0.46 mmol) was dissolved in DMF (4 ml) and pyridine (0.5 ml), then cooled to 0° C. 2-Methoxyethyl chloroformate (0.2 ml, 1.73 mmol) was added, the mixture was stirred at 0° C. for 45 minutes followed by addition of a second portion of 2-methoxyethyl chloroformate. The mixture was stirred for one additional hour at 0° C., then diluted with water, extracted twice with ethyl acetate and dried over sodium sulfate. The residue obtained upon filtration and evaporation was purified via chromatography (silica gel, 0 to 10% acetonitrile in ethyl acetate). Evaporation of the product containing fractions and trituration of the resulting solid with diethyl ether yielded the title compound as a white solid (0.20 g), melting point: 112° C.

MS (ESP): 541 (MH$^+$) for $C_{25}H_{25}FN_6O_7$ $^1$H-NMR(300 MHz, DMSO-$d_6$) δ: 3.51 (m, 2H); 3.60 (dd, 1H); 3.96 (dd, 1H); 4.19–4.24 (m, 3H); 4.28–4.33 (m, 2H); 4.86 (d, 2H); 5.02 (m, 1H); 5.19 (m, 1H); 7.42 (dd, 1H); 7.59 (dd, 1H); 7.69 (t, 1H); 7.77 (s, 1H); 8.00 (d, 1H); 8.07 (d, 1H); 8.18 (s, 1H); 8.83 (s, 1H).

Example 15 is a non-limiting example of a suitable pro-drug for compounds of the invention, and is a suitable pro-drug of Example 1.

which the mixture became a clear solution. The reaction was quenched with 1 mL of methanol and purged with diazomethane generated from 1-methyl-3-nitro-1-nitrosoguanidine (MNNG) in a diazomethane generator (Aldrich, cat. No. Z41,173–6) until all product was converted into its methylester as judged by LCMS and the solution turned yellow. The solvent was removed and the product purified by chromatography on silica using a gradient from 0–10% methanol in dichloromethane that yielded 31 mg (40%) of the title compound as a white solid.

MS (APCI): 567 (M+1) for $C_{27}H_{27}N_6O_7F$

NMR (300 MHZ) (DMSO-$d_6$) δ: 1.97 (m, 2H); 2.44 (m, 1H); 3.42 (dd, 1H); 3.70 (m, 4H); 4.05 (dd, 1H); 4.30 (m, 3H); 4.88 (m, 2H); 5.07 (m, 1H); 5.19 (m, 1H); 7.34 (d, 1H); 7.56 (m, 2H); 7.79 (s, 1H); 7.88 (s, 1H); 7.98 (d, 1H); 8.12 (d, 1H); 8.83 (s, 1H)

$^{19}$F-NMR (300 MHZ) (DMSO-$d_6$) δ: −112.79

Example 16 is a non-limiting example of a suitable pro-drug for compounds of the invention, and is a suitable pro-drug of Example 1.

Example 16

[(5S)-3-(5-{2-Fluoro-4-[(5R)-2-oxo-5-(1H-1,2,3-triazol-1-ylmethyl)-1,3-oxazolidin-3-yl]phenyl}-2-pyridinyl)-4,5-dihydro-5-isoxazolyl]methyl methyl pentanedioate Example 17

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl 4-methoxybutanoate

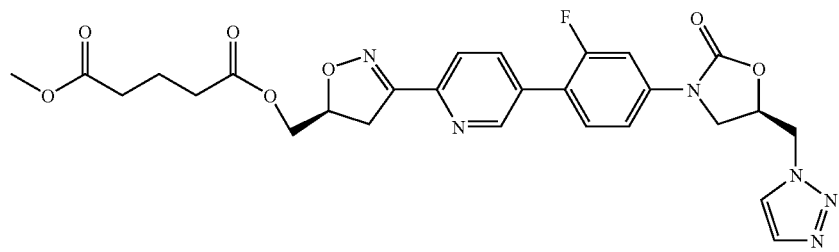

(5R)-3-(3-Fluoro-4-{6-[(5S)-5-(hydroxymethyl)-4,5-dihydro-3-isoxazolyl]-3-pyridinyl}phenyl)-5-(1H-1,2,3-triazol-1-ylmethyl)-1,3-oxazolidin-2-one (Example 1, 60 mg, 0.13 mmol) was suspended in 2 mL of anhydrous dimethylformamide. Anhydrous pyridine (1 mL, 12 mmol), 4-dimethylaminopyridine (DMAP) (10 mg, 0.08 mmol) and glutaric anhydride (75 mg, 0.55 mmol) were added and the solution was stirred for 16 hours at room temperature during

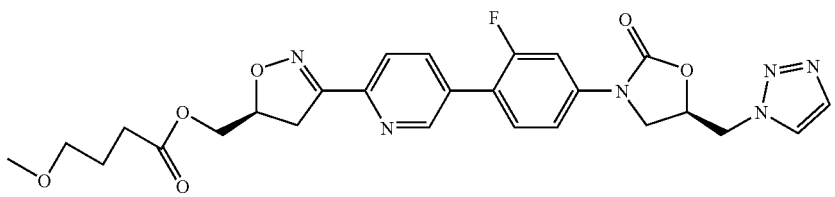

(5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1, 0.125 g, 0.29 mmol), 3-methoxypropionic acid (0.13 g, 1.1 mmol), 4-dimethylaminopyridine (0.003 g, 0.025 mmol), and 1-[3-(dimethylamino)propyl]-3-ethylcarbodiimide hydrochloride (0.125 g, 0.65 mmol) were combined in DMF (2 ml). The suspension was allowed to stir for 1.5 hours at room temperature resulting in a clear solution. The mixture was then diluted with ethyl acetate, washed with water, and dried over magnesium sulfate. The residue obtained upon filtration and evaporation was sonnicated with a solution of dichloromethane:ether (1:5) to give a solid which was dried collected and dried in vacuo. The title compound was obtained as a white solid (0.15 g), melting point: 154° C.

MS (ESP): 539 (MH$^+$) for $C_{26}H_{27}FN_6O_6$ $^1$H-NMR(300 MHz DMSO-d$_6$) δ: 1.66–1.75 (m, 2H); 2.33 (t, 2H); 3.15 (s, 3H); 3.26 (t, 2H); 3.58 (dd, 1H); 3.95 (dd, 1H); 4.12–4.18 (m, 2H); 4.24–4.33 (m, 2H); 4.86 (d, 2H); 5.00 (m, 1H); 5.18 (m, 1H); 7.42 (dd, 1H); 7.59 (dd, 1H); 7.69 (t, 1H); 7.76 (s, 1H); 7.99 (d, 1H); 8.06 (bd, 1H); 8.18 (s, 1H); 8.82 (s, 1H).

NMR (300 MHZ) (CDCL$_3$) δ: 2.09 (s, 3H); 3.40 (dd, 1H); 3.63 (dd, 1H); 4.02 (dd, 1H); 4.21 (m, 3H); 4.82 (d, 2H); 5.07 (m, 2H); 7.21 (d, 1H); 7.43 (m, 2H); 7.77 (d, 2H); 7.89 (d, 1H); 8.09 (d, 1H); 8.74 (s, 1H)

$^{19}$F-NMR (300 MHZ) (CDCl$_3$) δ: –114.26

Example 18 is a non-limiting example of a uitable pro-drug for compounds of the invention, and is a suitable pro-drug of Example 1.

Example 19

[(5S)-3-(5-{2-Fluoro-4-[(5R)-2-oxo-5-(1H-1,2,3-triazol-1-ylmethyl)-1,3-oxazolidin-3-yl]phenyl}-2-pyridinyl)-4,5-dihydro-5-isoxazolyl]methyl methyl 1,2-cyclohexanedicarboxylate

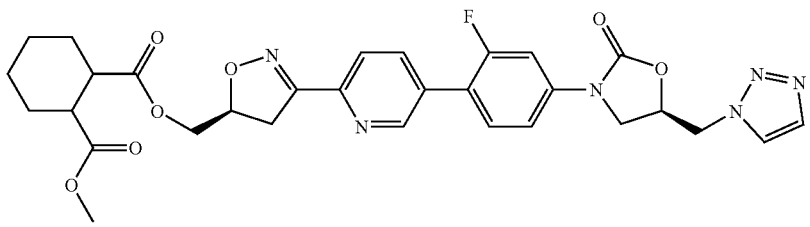

Example 17 is a non-limiting example of a suitable pro-drug for compounds of the invention, and is a suitable pro-drug of Example 1.

Example 18

[(5S)-3-(5-{2-Fluoro-4-[(5R)-2-oxo-5-(1H-1,2,3-triazol-1-ylmethyl)-1,3-oxazolidin-3-yl]phenyl}-2-pyridinyl)-4,5-dihydro-5-isoxazolyl]methyl acetate

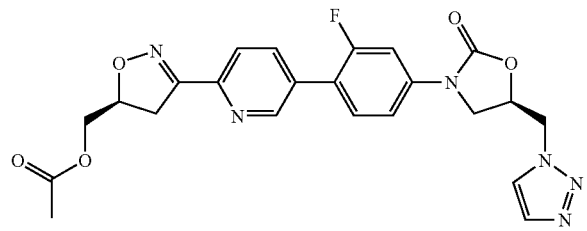

(5R)-3-(3-Fluoro-4-{6-[(5S)-5-(hydroxymethyl)-4,5-dihydro-3-isoxazolyl]-3-pyridinyl}phenyl)-5-(1H-1,2,3-triazol-1-ylmethyl)-1,3-oxazolidin-2-one (Example 1, 200 mg, 0.46 mmol) was suspended in 2 mL of anhydrous dimethylformamide. Anhydrous pyridine (2 mL, 24 mmol), 4-dimethylaminopyridine (DMAP) (20 mg, 0.17 mmol) and di-O-acetyl-L-tartaric anhydride (210 mg, 0.97 mmol) were added and the solution was stirred for 16 hours at room temperature during which the mixture turned black. The reaction was quenched with 1 mL of methanol, the solvents evaporated in vacuo and the product isolated by flash chromatography on silica using a gradient from 0 to 5% methanol in dichloromethane to yield 50 mg (25%) of the title compound as an off white solid.

MS (APCI): 481 (M+1) for $C_{23}H_{21}N_6O_5F$ (5R)-3-(3-Fluoro-4-{6-[(5S)-5-(hydroxymethyl)-4,5-dihydro-3-isoxazolyl]-3-pyridinyl}phenyl)-5-(1H-1,2,3-triazol-1-ylmethyl)-1,3-oxazolidin-2-one (Example 1, 60 mg, 0.13 mmol) was suspended in 2 mL of anhydrous dimethylformamide. Anhydrous pyridine (1 mL, 12 mmol), 4-dimethylaminopyridine (MAP) (10 mg, 0.08 mmol) and cis-hexahydrophthalic anhydride (85 mg, 0.55 mmol) were added and the solution was stirred for 16 hours at room temperature during which the mixture became a clear solution. The reaction was quenched with 1 mL of methanol and purged with diazomethane generated from 1-Methyl-3-nitro-1-nitrosoguanidine (MNNG) in a diazomethanegenerator (Aldrich, cat. No. Z41,173-6) until all product was converted into its methyl ester as judged by LCMS and the solution turned yellow by excess diazomethane. The solvent was removed and the product purified by chromatography on silica using a gradient from 0–20% methanol in dichloromethane that yielded 40 mg (48%) of the title compound as an off white solid.

MS (APCI): 607 (M+1) for $C_{30}H_{31}N_6O_7F$

NMR (300 MHZ) (CDCl$_3$) δ: 1.38 (m, 4H); 1.70 (m, 2H); 1.94 (m, 2H); 2.81 (m, 2H); 3.31 (dd, 1H); 3.55 (m, 1H); 3.65 (d, 3H); 4.00 (dd, 1H); 4.21 (m, 3H); 4.82 (d, 2H); 5.01 (m, 1H); 5.10 (m, 1H); 7.21 (dd, 1H); 7.40 (m, 2H); 7.77 (d, 2H); 7.89 (d, 1H); 8.09 (d, 1H); 8.74 (s, 1H).

$^{19}$F-NMR (300 MHZ) (CDCl$_3$) δ: –114.46

Example 19 is a non-limiting example of a suitable pro-drug for compounds of the invention, and is a suitable pro-drug of Example 1.

Example 20

[(5S)-3-(5-{2-Fluoro-4[-(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl phosphate, bisammonium salt (5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1, 8 g, 18.3 mmol) [crude material from water precipitation of Suzuki reaction] was suspended in toluene (250 ml) and concentrated to near dryness, then dissolved in DMF (120 ml) with heating and stirring and cooled to 0° C. To this clear solution was added di-t-butyl-diethylphosphoramidite (12 ml, 40.2

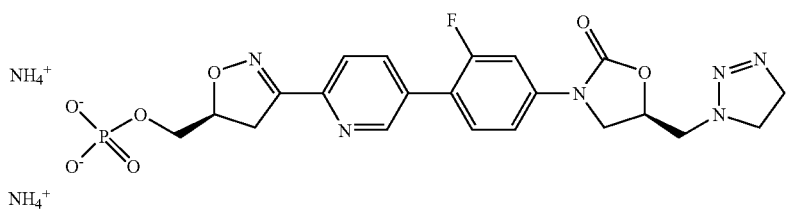

Di-tert-butyl [(5S)-3-(5-{2-fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl phosphate (Intermediate 19, 6.07 g, 9.63 mmol) was added to MeOH:CH$_2$Cl$_2$ 1:1 (100 ml). 4 N HCl in dioxane (15 ml) was then added and the reaction was allowed to stir at room temperature for 2 hours. The solution was then poured into Et$_2$O (800 ml) and the precipitate was collected by vacuum filtration. The precipitate was then washed with Et$_2$O (3×100 ml) and then dried in vacuo for 1 hour. The resulting solid was then dissolved in a mixture of distilled water (60 ml) and concentrated ammonium hydroxide (5 ml). The aqueous solution was then frozen in a round bottom flask using dry ice/acetone and placed on a freeze dryer for 2 days. The solid was then suspended in a mixture of MeOH (60 ml) and Et$_2$O (200 ml) and then filtered. The solid was washed with additional Et$_2$O (2×100 ml) and then placed in a round bottom flask in vacuo overnight to yield the product (5.262 g).

MS (ESP): 519.28 (MH$^+$) for C$_{21}$H$_{20}$FN$_6$O$_7$P $^1$H-NMR 500 MHz (D$_2$O) δ: 3.28 (m, 1H); 3.44 (dd, 1H); 3.92 (m, 3H); 4.18 (m, 1H); 4.70 (under water peak, 2H); 4.81 (dd, 1H); 4.89 (m, 1H); 5.03 (bs, 1H); 5.11 (bs, 1H); 6.98 (d, 1H); 7.12 (d, 1H); 7.24 (t, 1H); 7.61 (bs, 1H); 7.69 (bs, 1H); 7.75 (s, 1H); 8.04 (s, 1H); 8.39 (s, 1H).

Example 20 is a non-limiting example of a suitable pro-drug for compounds of the invention, and is a suitable pro-drug of Example 1.

Intermediate 19: Di-tert-butyl [(5S)-3-(5-{2-fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl phosphate mmol), followed by the addition of a 0.34M solution of tetrazole in acetonitrile (107 ml, 36 mmol) portionwise over approximately 10 minutes. The solution was stirred for one hour at 0° C., after which additional portions of di-t-butyl-diethylphosphoramidite (2.7 ml, 9.04 mmol) and 0.34M solution of tetrazole in acetonitrile (27 ml, 9.18 mmol) were added. After an additional 30 minutes of stirring at 0° C. the solution was cooled to approximately −70° C. over a dry ice-isopropanol bath. A solution of 3-chloroperbenzoic acid (70%, 9.04 g, 37 mmol) in dichloromethane (125 ml) was prepared and dried over sodium sulfate, then added to the reaction mixture over approximately 10 minutes. The clear solution was stirred over the cold bath for 10 minutes, and then 0.5M sodium thiosulfate was added (400 ml). The mixture was removed from the cold bath and stirred vigorously for 5 minutes. Ethyl acetate was added, the layers were separated and the aqueous layer was extracted with ethyl acetate. The pooled organic layers were washed with saturated sodium bicarbonate, then saturated sodium chloride, dried over sodium sulfate and evaporated. The residue was purified via column chromatography (0.5 to 5% methanol in dichloromethane). The product is soluble in dichloromethane, poorly soluble in ethyl acetate. The title compound was obtained as a cream colored foam, 6.6 g (58%). This material could be crystallized from ethyl acetate: hexane if necessary. This sample was pure enough to carry on to deprotection.

$^1$H-NMR 300 MHz (DMSO-d$_6$) δ: 1.36 (s, 9H); 1.39 (s, 9H); 3.33 (dd, 1H); 3.58 (dd, 1H); 4.01 (m, 3H); 4.29 (t, 1H); 4.86 (d, 2H); 4.99 (bm, 1H); 5.18 (m, 1H); 7.42 (dd, 1H); 7.59 (dd, 1H); 7.69 (t, 1H); 7.76 (d, 1H); 7.99 (d, 1H); 8.06 (d, 1H); 8.18 (d, 1H); 8.82 (bs, 1H).

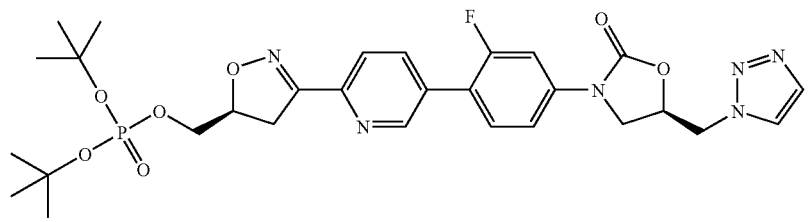

Example 21

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl hydrogen sulfate

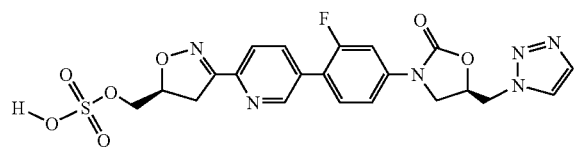

(5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1, 200 mg, 0.46 mmol) and sulfur trioxide pyridine complex (300 mg, 1.89 mmol) were added to pyridine (2 ml) and DMSO (2 ml). The reaction was allowed to stir at room temperature for 2 hours and the pyridine was removed in vacuo. The residue was purified by reverse phase HPLC, 0–50% ACN/H$_2$O 0.1% TPA over 15 minutes to yield the compound as a yellow flowing powder 117 mg).

MS (ESP): 519.21 (MH$^+$) for C$_{21}$H$_{19}$FN$_6$O$_7$S $^1$H-NMR 500 MHz (DMSO-d$_6$) δ: 3.68 (dd, 1H); 3.53 (dd, 1H); 3.87 (m, 2H); 3.98 (m, 1H); 4.33 (t, 1H); 4.88 (d, 2H); 4.98 (m, 1H); 5.21 (m, 1H); 5.69 (s, 3H); 7.44 (dd, 1H); 7.62 (dd, 1H); 7.73 (t, 1H); 7.79 (s, 1H); 8.03 (d, 1H); 8.10 (d, 1H); 8.21 (s, 1H); 8.85 (s, 1H).

Example 21 is a non-limiting example of a suitable pro-drug for compounds of the invention, and is a suitable pro-drug of Example 1.

Example 22

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl piperidine-4-carboxylate (5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1, 250 mg, 0.57 mmol), Boc-piperidine-4-carboxylic acid (196 mg, 0.86 mmol), 1-ethyl-3-(3-dimethylaminopropyl)carbodiimide hydrochloride (219 mg, 1.14 mmol), and 4-dimethylaminopyridine (17.4 mg, 0.14 mmol) were added to DMF (3 ml). The reaction was allowed to stir at room temperature for 3 hours. The reaction mixture was added to distilled water (50 ml) and the precipitate was collected by filtration. The precipitate was then purified by column chromatography 0–5% MeOH/CH$_2$Cl$_2$ to yield a white powder (271 mg). The resulting product (250 mg) was added to CH$_2$Cl$_2$ (20 ml) and then 4 N HCl in dioxane (3 ml) was added and the reaction was allowed to stir for 3 hours. Et$_2$O (20 ml) was then added and the precipitate was collected by filtration under nitrogen gas to yield the product as a yellow solid (250 mg).

MS (ESP): 550.30 (MH$^+$) for C$_{27}$H$_{28}$FN$_7$O$_5$ $^1$H-NMR 300 MHz (DMSO-d$_6$) δ: 1.67 (m, 2H); 1.88 (m, 2H); 2.66 (m, 1H); 2.81 (m, 2H); 3.10 (m, 2H); 3.29 (dd, 1H); 3.55 (dd, 1H); 3.91 (dd, 1H); 4.14 (dd, 1H); 4.24 (m, 2H); 4.80 (d, 1H); 4.97 (m, 1H); 5.13 (m, 1H); 7.36 (dd, 1H); 7.54 (dd, 1H); 7.64 (dd, 1H); 7.71 (s, 1H); 7.95 (d, 1H); 8.02 (d, 1H); 8.14 (s, 1H); 8.77 (s, 2H); 9.01 (s, 1H).

Example 22 is a non-limiting example of a suitable pro-drug for compounds of the invention, and is a suitable pro-drug of Example 1.

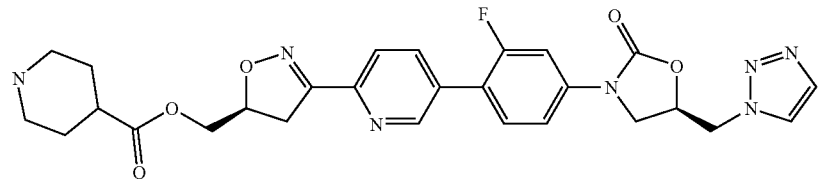

Example 23

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl 4-(dimethylamino)pentanoate

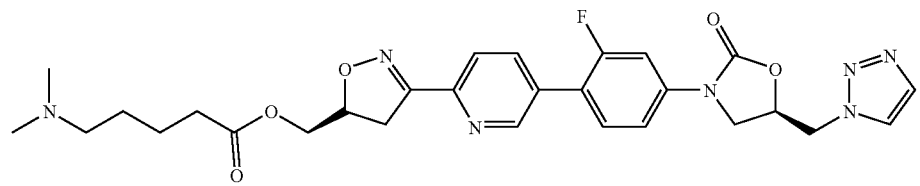

(5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1,150 mg, 0.342 mmol), 4-(dimethylamino)pentanoic acid (63.6 mg, 0.514 mmol), 1-ethyl-3-(3-dimethylaminopropyl)carbodiimide hydrochloride (131.5 mg, 0.69 mmol), and 4-dimethylaminopyridine (10.5 mg, 0.09 mmol) were added to DMF (3 ml). The reaction was allowed to stir overnight at room temperature followed by addition to EtOAc (40 ml). The precipitate was collected by filtration and then purified by column chromatography 0–5% MeOH/CH$_2$Cl$_2$ to yield a white powder (100 mg).

MS (ESP): 566.32 (MH$^+$) for C$_{28}$H$_{32}$FN$_7$O$_5$ $^1$H-NMR 300 MHz (DMSO-d$_6$) δ: 1.34 (m, 3H); 2.17 (t, 2H); 2.29 (s, 4H); 2.73 (m, 2H); 3.11 (m, 4H); 3.39 (dd, 1H); 3.75 (dd, 1H); 3.96 (dd, 1H); 4.09 (m, 1H); 4.65 (d, 2H); 4.81 (m, 1H); 4.98 (m, 1H); 7.21 (d, 1H); 7.38 (d, 1H); 7.49 (t, 1H); 7.56 (s, 1H) 7.82 (dd, 2H); 7.98 (s, 1H); 8.60 (s, 1H); 9.75 (s, 1H).

Example 23 is a non-limiting example of a suitable pro-drug for compounds of the invention, and is a suitable pro-drug of Example 1.

Example 24

4-{[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methoxy}-4-oxobutanoic acid

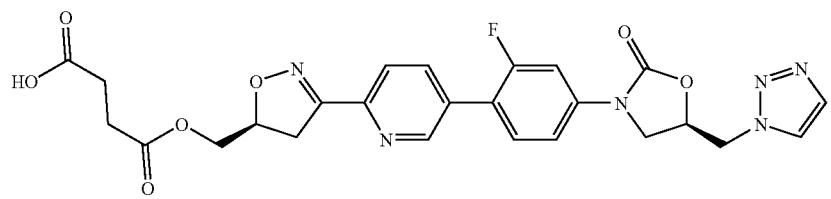

(5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 150 mg, 0.342 mmol), dihydrofuran-2,5-dione (83 mg, 0.83 mmol), and 4-dimethylaminopyridine (10.5 mg, 0.09 mmol) were added to DMF (2.5 ml) and pyridine (0.5 ml). The reaction was allowed to stir overnight at room temperature followed by addition to Et$_2$O (100 ml). The precipitate was collected by filtration and washed with additional Et$_2$O (2×20 ml). The precipitate was then suspended in CH$_2$Cl$_2$ (20 ml) and the precipitate was collected by filtration and then washed with additional CH$_2$Cl$_2$ (2×20 ml) to yield the product as a white solid (131 mg).

MS (ESP): 539.37 (MH$^+$) for C$_{25}$H$_{23}$FN$_6$O$_7$ $^1$H-NMR 300 MHz (DMSO-d$_6$) δ: 2.54 (m, 2H); 3.35 (m, 3H); 3.62 (dd, 1H); 3.99 (dd, 1H); 4.28 (m, 3H); 4.86 (d, 2H); 5.06 (m, 1H); 5.26 (m, 1H); 7.47 (d, 1H); 7.81 (d, 1H); 7.87 (t, 1H); 7.91 (s, 1H); 8.07 (t, 2H); 8.24 (s, 1H); 8.84 (s, 1H); 12.26 (s, 1H).

Example 24 is a non-limiting example of a suitable pro-drug for compounds of the invention, and is a suitable pro-drug of Example 1.

Example 25

[(5S)-3-(5-{2-fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl nicotinate 1-oxide

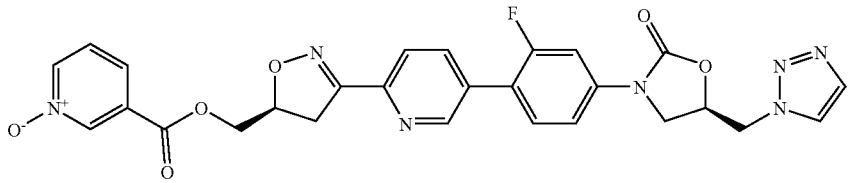

(5R)-3-(3-fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 130 mg, 0.30 mMol), nicotinic acid 1-oxide (100 mg, 0.72 mMol), 1,3-diisopropylcarbodiimide (290 mg, 2.3 mMol), and 4-dimethylaminopyridine (5 mg, 0.04 mMol) were suspended in 2 ml of DMF at room temperature. The mixture was stirred one day, diluted with methanol (2 ml), stirred 5 minutes and then further diluted with diethyl ether (20 ml) to give a suspension. The solids were collected and rinsed with diethyl ether, then suspended in acetonitrile:methanol (1:1, 150 ml), the mixture was warmed and stirred a few minutes, then allowed to cool. The suspension was filtered and the filtrate was concentrated to a volume of 10 ml to give a suspension. The solids were collected, rinsed with acetonitrile, then diethyl ether and dried under vacuum to yield the title compound as an off-white solid (90 mg), melting point: 255° C.

MS (electrospray): 560 (MH$^+$) for C$_{27}$H$_{22}$FN$_7$O$_6$ $^1$H-NMR (500 MHz, DMSO-d$_6$) δ: 3.48 (dd, 1H); 3.67 (dd, 1H); 3.96 (dd, 1H); 4.30 (t, 1H); 4.45 (dd, 1H); 4.53 (dd, 1H); 4.86 (d, 2H); 5.19 (m, 2H); 7.42 (dd, 1H); 7.52 (t, 1H); 7.59 (dd, 1H); 7.69 (d, 1H); 7.73 (d, 1H); 7.77 (s, 1H); 8.01 (d, 1H); 8.07 (d, 1H); 8.18 (s, 1H); 8.42 (d, 1H); 8.45 (s, 1H); 8.88 (s, 1H).

Example 25 is a non-limiting example of a suitable pro-drug for compounds of the invention, and is a suitable pro-drug of Example 1.

Example 26

[3-(5-{2-fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl N,N-dimethylglycinate

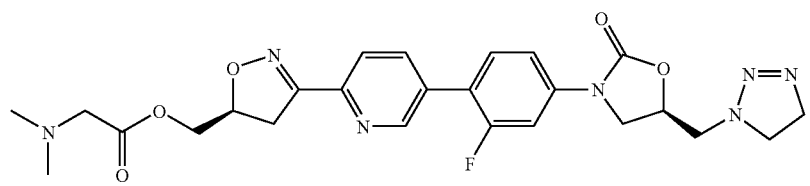

(5R)-3-(3-fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 250 mg, 0.57 mMol), N,N-dimethylglycine (150 mg, 1.46 mMol), 1-[3-(dimethylamino)propyl]-3-ethylcarbodiimide hydrochloride (300 mg, 1.56 mMol), and 4-dimethylaminopyridine (5 mg, 0.04 mMol) were suspended in 5 ml of DMF at room temperature. The mixture was stirred overnight and then concentrated. The residue was purified by chromatography (silica gel; elution with 1 to 10% methanol in dichloromethane) to give the free base of the title compound as a white solid (250 mg). Mp 185–198° C.

A portion of the sample was dissolved in ethyl acetate: acetonitrile (1:1, 12 ml) with warming, treated with 4M HCl in dioxane solution (1 ml) and diluted with ether to 100 ml. The solid was collected, rinsed with ether and dried in vacuo to yield the hydrochloride salt of the title compound as a hygroscopic light yellow solid (250 mg). Mp 175–180° C.

MS (electrospray): 524 (M+1) for $C_{25}H_{26}FN_7O_5$ $^1$H-NMR (300 MHz, DMSO-$d_6$) [HCl salt] δ: 2.82 (s, 6H); 3.38 (dd, 1H); 3.63 (dd, 1H); 3.96 (dd, 1H); 4.24–4.36 (m, 4H); 4.44 (dd, 1H); 4.86 (d, 2H); 5.07 (m, 1H); 5.19 (m, 1H); 7.42 (dd, 1H); 7.58 (dd, 1H); 7.69 (t, 1H); 7.76 (s, 1H); 8.01 (d, 1H); 8.07 (d, 1H); 8.18 (s, 1H); 8.83 (s, 1H); 10.15 (bs, 1H)

Example 26 is a non-limiting example of a suitable pro-drug for compounds of the invention, and is a suitable pro-drug of Example 1.

Example 27

[(5S)-3-(5-{2-fluoro-4-[(5R)-2-oxo-5-(1H-1,23-triazol-1-ylmethyl)-1,3-oxazolidin-3-yl]phenyl}pyridin-2-yl)-4,5-dihydroisoxazol-5-yl]methyl 5-[(ethoxycarbonyl)amino]pentanoate

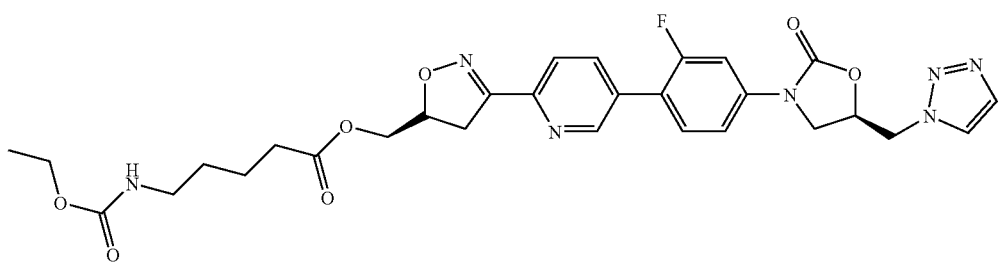

5-aminopentanoic acid hydrochloride (1 g, 6.5 mmol), and potassium carbonate (6.5 g, 47 mmol) were dissolved in water (15 ml) and dioxane (5 ml) then cooled to 0° C. Ethyl chloroformate (3 ml, 31.5 mmol) was added over 30 seconds, then the mixture was stirred for 4 hours at 0° C. Conc. HCl was added until acidic then the mixture was diluted with water and extracted with ether. The organic layer was dried over magnesium sulfate, evaporated and dried in vacuo to give 5-[(methoxycarbonyl)amino]pentanoic acid as a white powder (1.07 g).

The ethyl carbamate prepared as above (0.175 g, 0.93 mmol), (5R)-3-(3-fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 0.25 g, 0.57 mmol), 4-dimethylaminopyridine (0.01 g, 0.08 mmol), and 1-[3-(dimethylamino)propyl]-3-ethylcarbodiimide hydrochloride (0.19 g, 0.99 mmol) were combined in DMF (2 ml). The suspension was allowed to stir for 3.5 hours at room temperature resulting in a clear solution. The mixture was then diluted with ethyl acetate, washed with water, and dried over magnesium sulfate. The residue obtained upon filtration and evaporation was purified via chromatography (silica gel, 0.5 to 10% methanol in dichloromethane). Evaporation of the product containing fractions and trituration of the resulting solid with diethyl ether yielded the title compound as a white powder (0.25 g), melting point: 183° C.

MS (electrospray): 610 (MH$^+$) for $C_{29}H_{32}FN_7O_7$

¹H-NMR (300 MHz, DMSO-d₆) δ: 1.12 (t, 3H); 1.35 (m, 2H); 1.47 (m, 2H); 2.30 (t, 2H); 2.90 (m, 2H); 3.30 (dd, 1H); 3.58 (dd, 1H); 3.91–3.98 (m, 3H); 4.15 (dd, 1H); 4.25 (dd, 1H); 4.30 (t, 1H); 4.86 (d, 2H); 5.00 (m, 1H); 5.19 (m, 1H); 7.02 (bt, 1H); 7.42 (dd, 1H); 7.59 (dd, 1H); 7.69 (t, 1H); 7.76 (s, 1H); 8.00 (d, 1H); 8.06 (d, 1H); 8.18 (s, 1H); 8.82 (s, 1H).

Example 27 is a non-limiting example of a suitable pro-drug for compounds of the invention, and is a suitable pro-drug of Example 1.

Example 28

2-{[(5S)-3-(5-{2-fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methoxy}-N,N,N-trimethyl-2-oxoethanaminium chloride

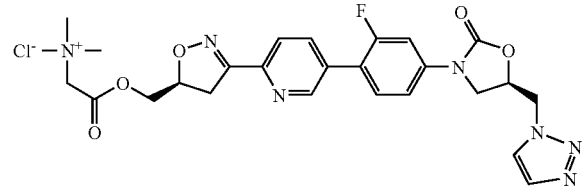

[3-(5-{2-fluoro-4-[(5R)-2-oxo-5-(1H-1,2,3-triazol-1-yl-methyl)-1,3-1,3-oxazolidin-3-yl]phenyl}pyridin-2-yl)-4,5-dihydroisoxazol-5-yl]methyl N,N-dimethylglycinate (Example 26: 100 mg, 0.19 mMol), was dissolved in 1 ml of DMF with heating, then cooled to room temperature. Methyl iodide (0.15 ml, 2.4 mmol) was added and the mixture was stirred 45 minutes then diluted with ether (15 ml). The oily suspension was sonicated, triturated and decanted to give a residue, which was triturated with ethyl acetate (5 ml). The resulting solid was dissolved in 2:1 acetonitrile:water (6 ml) and passed through a 2 g cartridge of C-18 reverse phase silica gel which was subsequently rinsed with 1:1 acetonitrile:water (15 ml). Dowex 1X2-100 (chloride form ion exchange resin, 5 g) was added to the combined filtrates, the suspension was stirred a few minutes and then filtered. The resin bed was rinsed with acetonitrile and the combined filtrates were evaporated. The residue was combined with 10:1 ethyl acetate:acetonitrile (11 ml), sonnicated and triturated to give a solid which was collected and rinsed with ethyl acetate. The material was dried in vacuo to yield the title compound as a white solid (100 mg). Mp 188° C.

¹H-NMR (400 MHz, DMSO-d₆) δ: 3.22 (s, 9H); 3.39 (dd, 1H); 3.63 (dd, 1H); 3.96 (dd, 1H); 4.27–4.36 (m, 2H); 4.44 (dd, 1H); 4.48 (s, 2H); 4.86 (d, 2H); 5.08 (m, 1H); 5.19 (m, 1H); 7.42 (dd, 1H); 7.59 (dd, 1H); 7.69 (t, 1H); 7.76 (s, 1H); 8.00 (d, 1H); 8.08 (d, 1H); 8.18 (s, 1H); 8.83 (s, 1H).

Example 28 is a non-limiting example of a suitable pro-drug for compounds of the invention, and is a suitable pro-drug of Example 1.

Example 29

(5S)-3-(5-{2-fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl 3-methoxypropyl carbonate

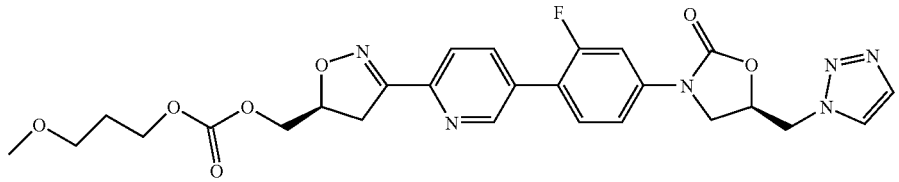

3-methoxy-1-propanol (155 mg, 1.72 mMol) was dissolved in dichloromethane (3 ml) and cooled to 0° C. Phosgene (20% in toluene: 1.5 ml, 2.8 mMol) was added and the solution was allowed to slowly come to room temperature overnight. The solution was concentrated in vacuo to give the chloroformate intermediate as a clear oil, which was dissolved in dichloromethane (2 ml). The chloroformate solution was added to an ice cold solution of (5R)-3-(3-fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 200 mg, 0.46 mMol), DMF (5 ml) and pyridine (0.4 ml, 4.96 mMol). The mixture was allowed to come to room temperature over 10 minutes, then stirred for 2 hours more. Ethyl acetate was added, followed by washing with saturated NaCl. The organic layer was dried over sodium sulfate, evaporated and purified by chromatography (silica gel; elution with 1 to 10% methanol in dichloromethane). The product containing fractions were pooled, evaporated, dissolved in a minimum amount of dichloromethane and precipitated with ether. The solid was collected on a filter and rinsed with ether. The title compound was thus obtained as a white solid, 133 mg. Mp 142° C.

MS (electrospray): 555 (M+1) for $C_{26}H_{27}FN_6O_7$

¹H-NMR (400 MHz, DMSO-d₆) δ: 1.80 (p, 2H); 3.19 (s, 3H); 3.33 (m, 2H); 3.59 (dd, 1H); 3.96 (dd, 1H); 4.12 (t, 2H); 4.22 (dd, 1H); 4.30 (m, 3H); 4.86 (d, 2H); 5.02 (m, 1H); 5.19 (m, 1H); 7.42 (dd, 1H); 7.59 (dd, 1H); 7.69 (t, 1H); 7.76 (s, 1H); 8.00 (d, 1H); 8.06 (d, 1H); 8.18 (s, 1H); 8.82 (s, 1H).

Example 29 is a non-limiting example of a suitable pro-drug for compounds of the invention, and is a suitable pro-drug of Example 1.

Example 30

[(5S)-3-(5-{2-fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methylpyrazine-2-carboxylate

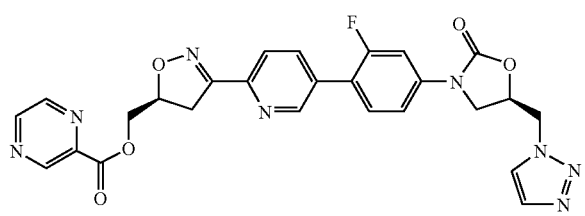

Pyrazine-2-carboxylic acid (118 mg, 0.95 mMol), (5R)-3-(3-fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 200 mg, 0.46 mMol), 4-(dimethylamino)pyridine (5 mg, 0.041 mmol) and DMF (2 ml) were combined and warmed to give a clear solution. The solution was allowed to cool to room temperature, and then diisopropylcarbodiimide (0.15 ml, 0.96 mmol) was added. The mixture was stirred for 18 hours, ethyl acetate was added, followed by washing with saturated NaCl. The organic layer was dried over sodium sulfate, evaporated, triturated with 1:5 ether:hexane, dissolved in 1:1 acetonitrile:methanol, adsorbed on silica gel and purified by chromatography (silica gel; elution with 1 to 10% methanol in dichloromethane). The product containing fractions were pooled and evaporated to give the title compound as a white solid, 159 mg.

Mp 205–226° C.

MS (electrospray): 545 (M+1) for $C_{26}H_{21}FN_8O_5$ $^1$H-NMR (400 MHz. DMSO-$d_6$) δ: 3.48 (dd, 1H); 3.67 (dd, 1H); 3.96 (dd, 1H); 4.30 (t, 1H); 4.49 (dd, 1H); 4.59 (dd, 1H); 4.86 (d, 2H); 5.18 (m, 2H); 7.42 (dd, 1H); 7.59 (dd, 1H); 7.70 (t, 1H); 7.77 (s, 1H); 8.00 (d, 1H); 8.07 (dm, 1H); 8.18 (s, 1H); 8.82 (dm, 2H); 8.88 (d, 1H); 9.14 (d, 1H).

Example 30 is a non-limiting example of a suitable pro-drug for compounds of the invention, and is a suitable pro-drug of Example 1.

Example 31

[(5S)-3-(5-{2-fluoro-4-[(5R)-2-oxo-5-(1H-1,2,3-triazol-1-ylmethyl)-1,3-oxazolidin

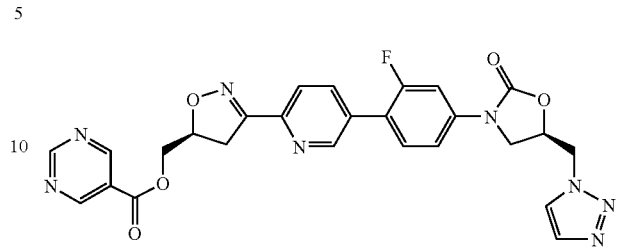

Pyrimidine-5-carboxylic acid (113 mg, 0.91 mMol), (5R)-3-(3-fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 200 mg, 0.46 mMol), 4-(dimethylamino)pyridine (5 mg, 0.041 mmol) and DMF (2 ml) were combined and warmed to give a clear solution. The solution was allowed to cool to room temperature, and then diisopropylcarbodiimide (0.15 ml, 0.96 mmol) was added. The mixture was stirred for 18 hours to give a suspension, which was diluted with ether (50 ml) and hexane (25 ml). The solids were collected, rinsed with ether, dissolved in 1:1 acetonitrile:methanol, adsorbed on silica gel and purified by chromatography (silica gel; elution with 1 to 10% methanol in dichloromethane). The product containing fractions were pooled and evaporated to give the title compound as a white solid, 160 mg.

Mp 253–264° C.

MS (electrospray): 545 (M+1) for $C_{26}H_{21}FN_8O_5$ $^1$H-NMR (400 MHz DMSO-d) δ: 3.52 (dd, 1H); 3.68 (dd, 1H); 3.96 (dd, 1H); 4.30 (t, 1H); 4.47 (dd, 1H); 4.58 (dd, 1H); 4.86 (d, 2H); 5.18 (m, 2H); 7.42 (dd, 1H); 7.59 (dd, 1H); 7.70 (t, 1H); 7.77 (s, 1H); 8.01 (d, 1H); 8.08 (dm, 1H); 8.18 (s, 1H); 8.83 (s, 1H); 9.17 (s, 2H); 9.39 (s, 1H).

Example 31 is a non-limiting example of a suitable pro-drug for compounds of the invention, and is a suitable pro-drug of Example 1.

Example 32

2-[({[(5S)-3-(5-{2-fluoro-4-[(5R)-2-oxo-5-(1H-1,2,3-triazol-1-ylmethyl)-1,3-oxazolidin-3-yl]phenyl}pyridin-2-yl)-4,5-dihydrolsoxazol-5-yl]methoxy}carbonyl)oxy]-N,N,N-trimethylethanaminium chloride

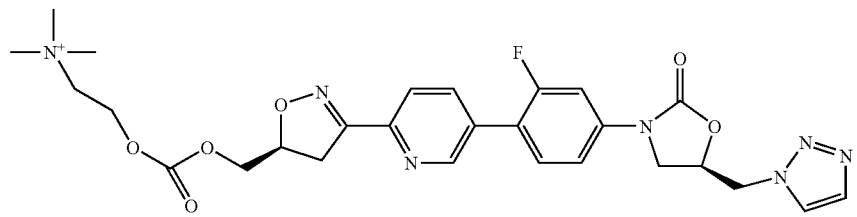

Choline chloride (2 g, 14.3 mmol) was suspended in THF (100 ml) and phosgene (1.93 M in toluene, 28 ml, 54.04 mmol) was added. The suspension was stirred vigorously for 40 hours followed by filtration, washing with hexane and drying in vacuo to yield crude choline chloroformate as a white solid (2.66 g).

(5R)-3-(3-fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 0.20 g, 0.46 mmol), was dissolved in DMF (5 ml) and pyridine (0.4 ml) with warming, then cooled to 0° C. Crude choline chloroformate (460 mg, 2.28 mmol) was added and the suspension was stirred and allowed to slowly warm to room temperature over 2 hours, then warmed to 50° C. for 4 hours. A second portion of crude choline chloroformate (460 mg, 2.28 mmol) was added and warming was continued for 12 hours. The mixture was diluted with methanol to give a clear solution, stirred a few minutes then concentrated in vacuo. The material was purified by reverse phase preparative HPLC (C8 stationary phase: 0.1% TFA, 5–50% acetonitrile/water gradient). The product containing fractions were evaporated to dryness, dissolved in methanol and passed over a bed of ~5 g Dowex 1X2-100 (Chloride form ion exchange resin), the resin was rinsed with methanol and the combined filtrates were evaporated to give a foamy yellow solid, which was dissolved in a minimum amount of methanol and precipitated with ether addition. The resulting thick oil was sonnicated and triturated with 1:1 acetonitrile:water to yield a solid, which was collected and rinsed with ether. This material was dried in vacuo to give the title compound as an off-white solid (110 mg), melting point: 180–190° C.

MS (electrospray): 569 (MH$^+$) for $C_{27}H_{31}FN_7O_6$ $^1$H-NMR (400 MHz. DMSO-d$_6$) δ: 3.09 (s, 9H); 3.34 (dd, 1H); 3.61 (dd, 1H); 3.69 (bm, 2H); 3.96 (dd, 1H); 4.24–4.32 (m, 2H); 4.37 (dd, 1H); 4.54 (bm, 2H); 4.86 (d, 2H); 5.04 (m, 1H); 5.19 (m, 1H); 7.42 (dd, 1H); 7.59 (dd, 1H); 7.69 (t, 1H); 7.76 (s, 1H); 8.00 (d, 1H); 8.07 (d, 1H); 8.18 (s, 1H); 8.83 (s, 1H).

Example 32 is a non-limiting example of a suitable pro-drug for compounds of the invention, and is a suitable pro-drug of Example 1.

Example 33

[(5S)-3-(5-{2-fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl 5-[(methoxycarbonyl)(methyl)amino]pentanoate 1-methyl-2-piperidone (5 ml, 44.1 mmol) was combined with barium hydroxide (3.8 g, 26.95 mmol) and water (55 ml). The suspension was warmed to 110° C. for 6 hours then cooled over an ice bath. Gaseous carbon dioxide was bubbled through the solution for 20 minutes. The suspension was filtered through a celite pad and the filtrate was concentrated to dryness. The residue was triturated with acetonitrile, collected, rinsed with ether and dried in vacuo to yield 5-(methylamino)pentanoic acid as a white solid (2.95 g). 5-(Methylamino)pentanoic acid (2 g, 15.3 mmol), and potassium carbonate (13 g, 94 mmol) were suspended in water (30 ml) and dioxane (10 ml) then cooled to 0° C. Methyl chloroformate (5 ml, 65 mmol) was added over 30 seconds, then the mixture was stirred and allowed to warm slowly to room temperature for 16 hours. Conc. HCl (20 ml) was added then the mixture was diluted with water and extracted with ethyl acetate. The organic layer was dried over magnesium sulfate, evaporated and dried in vacuo to give 5-[(methoxycarbonyl)(methyl)amino]pentanoic acid as a thick clear oil (2.56 g).

The carbamate prepared as above (0.175 g, 0.93 mmol), (5R)-3-(3-fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 0.25 g, 0.57 mmol), 4-dimethylaminopyridine (0.01 g, 0.08 mmol), and 1-[3-(dimethylamino)propyl]-3-ethylcarbodiimide hydrochloride (0.19 g, 0.99 mmol) were combined in DMF (2 ml). The suspension was allowed to stir for 3.5 hours at room temperature resulting in a clear solution. The mixture was then diluted with ethyl acetate, washed with water, and dried over magnesium sulfate. The residue obtained upon filtration and evaporation was purified via chromatography (silica gel, 0.5 to 10% methanol in dichloromethane). Evaporation of the product containing fractions and trituration of the resulting solid with diethyl ether yielded the title compound as a white powder (0.18 g), melting point: 82° C.

MS (electrospray): 610 (MH$^+$) for $C_{29}H_{32}FN_7O_7$ $^1$H-NMR (300 MHz DMSO-d) δ: 1.42 (bm, 4H); 2.32 (bm, 2H); 2.75 (s, 3H); 3.11 (bm, 2H); 3.28 (m, 1H); 3.53 (s, 3H); 3.58 (dd, 1H); 3.96 (dd, 1H); 4.16 (dd, 1H); 4.26 (dd, 1H); 4.29 (t, 1H); 4.86 (d, 2H); 5.01 (m, 1H); 5.19 (m, 1H); 7.42 (dd, 1H); 7.59 (dd, 1H); 7.69 (t, 1H); 7.77 (s, 1H); 8.00 (d, 1H); 8.06 (d, 1H); 8.18 (s, 1H); 8.82 (s, 1H).

Example 33 is a non-limiting example of a suitable pro-drug for compounds of the invention, and is a suitable pro-drug of Example 1.

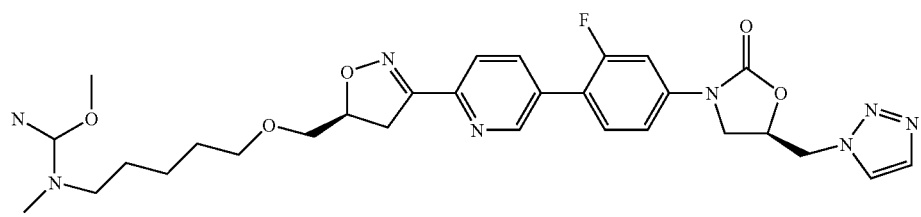

Example 34

[(5S)-3-(5-{2-fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl 5-[(tert-butoxycarbonyl)(methyl) amino]pentanoate

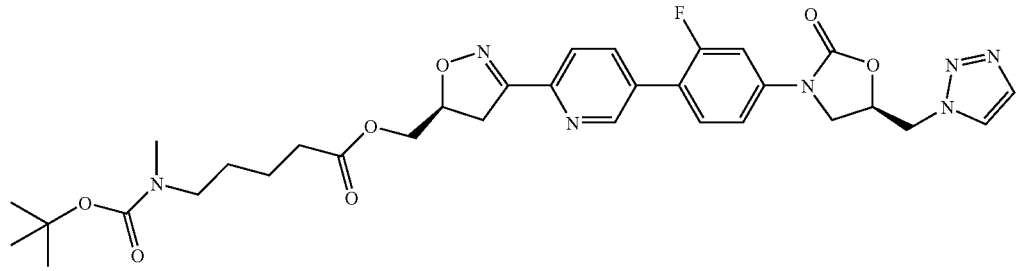

1-methyl-2-piperidone (5 ml, 44.1 mmol) was combined with barium hydroxide (3.8 g, 26.95 mmol) and water (55 ml). The suspension was warmed to 110° C. for 6 hours then cooled over an ice bath. Gaseous carbon dioxide was bubbled through the solution for 20 minutes. The suspension was filtered through a celite pad and the filtrate was concentrated to dryness. The residue was triturated with acetonitrile, collected, rinsed with ether and dried in vacuo to yield 5-(methylamino)pentanoic acid as a white solid (2.95 g). 5-(Methylamino)pentanoic acid (5 g, 38 mmol), and Sodium hydroxide (50% aqueous solution, 6.6 g, 82 mmol) were suspended in water (30 ml) and dioxane (20 ml). Di-tert-butyl dicarbonate (11 g, 50 mmol) was added, then the mixture was stirred at room temperature for 16 hours. The mixture was diluted with water, acidified to approximately pH 5 with concentrated HCl and extracted with dichloromethane. The organic layer was dried over magnesium sulfate, evaporated and dried in vacuo to give crude 5-[(tert-butoxycarbonyl)(methyl)amino]pentanoic acid as a thick clear oil (14 g).

The crude carbamate prepared as above (2 g, 8.6 mmol), (5R)-3-(3-fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 1 g, 2.28 mmol), 4-dimethylaminopyridine (0.05 g, 0.4 mmol), and 1-[3-(dimethylamino)propyl]-3-ethylcarbodiimide hydrochloride (1.28 g, 6.67 mmol) were combined in DMF (10 ml). The suspension was allowed to stir for 16 hours at room temperature, diluted with ethyl acetate, washed with water, and dried over magnesium sulfate. The residue obtained upon filtration and evaporation was purified via chromatography (silica gel, 0.5 to 5% methanol in dichloromethane). Evaporation of the product containing fractions and trituration of the resulting solid with diethyl ether yielded the title compound as an off-white solid (1.28 g), melting point: 121° C.

MS (electrospray): 652 (M1) for $C_{32}H_{38}FN_7O_7$ $^1$H-NMR (300 MHz, DMSO-d$_6$) δ: 1.35 (s, 9H); 1.41 (bs, 4H); 2.33 (bt, 2H); 2.69 (bs, 3H); 3.08 (bt, 2H); 3.29 (dd, 1H); 3.58 (dd, 1H); 3.96 (dd, 1H); 4.16 (dd, 1H); 4.26 (dd, 1H); 4.30 (t, 1H); 4.86 (d, 2H); 5.00 (m, 1H); 5.19 (m, 1H); 7.42 (dd, 1H); 7.59 (dd, 1H); 7.68 (t, 1H); 7.76 (s, 1H); 7.99 (d, 1H); 8.06 (d, 1H); 8.18 (s, 1H); 8.82 (s, 1H).

Example 34 is a non-limiting example of a suitable pro-drug for compounds of the invention, and is a suitable pro-drug of Example 1.

Example 35

[(5S)-3-(5-{2-fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl 4-[(methoxycarbonyl)(methyl)amino]butanoate

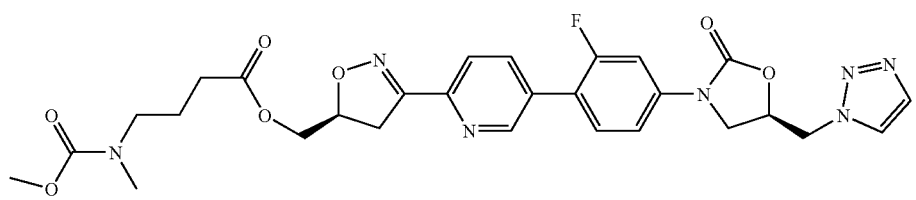

4-(Methylamino)butyric acid hydrochloride (5 g, 32.5 mmol), and potassium carbonate (18 g, 130 mmol) were suspended in water (50 ml) and dioxane (25 ml) then cooled to 0° C. Methyl chloroformate (13 ml, 168 mmol) was added over 1 minute, then the mixture was stirred and allowed to warm slowly to room temperature for 16 hours. Conc. HCl (20 ml) was added then the mixture was diluted with water and extracted with ethyl acetate. The organic layer was dried over magnesium sulfate, evaporated and dried in vacuo to give 4-[(methoxycarbonyl)(methyl)amino]butyric acid as a thick clear oil (9.7 g).

The carbamate prepared as above (0.32 g, 1.83 mmol), (5R)-3-(3-fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 0.2 g, 0.46 mmol), 4-dimethylaminopyridine (0.01 g, 0.08 mmol), and 1-[3-(dimethylamino)propyl]-3-ethylcarbodiimide hydrochloride (0.19 g, 0.99 mmol) were combined in DMF (2 ml). The suspension was allowed to stir for 2 hours at room temperature. The mixture was then diluted with ethyl acetate, washed with water, and dried over magnesium sulfate. The residue obtained upon filtration and evaporation was purified via chromatography (silica gel, 0.5 to 10% methanol in dichloromethane). Evaporation of the product containing fractions and trituration of the resulting solid with diethyl ether yielded the title compound as an off-white solid (0.23 g), melting point: 135° C.

MS (electrospray): 596 (MH+) for $C_{28}H_{30}FN_7O_7$ $^1$H-NMR (300 MHz DMSO-$d_6$) δ: 1.67 (p, 2H); 2.27 (t, 2H); 2.73 (s, 3H); 3.16 (t, 2H); 3.31 (dd, 1H); 3.53 (s, 3H); 3.59 (dd, 1M); 3.96 (dd, III); 4.15 (dd, 1H); 4.26 (dd, 1H) 4.30 (t, 1H); 4.86 (d, 2H); 5.01 (m, 1H); 5.18 (m, 1H); 7.42 (dd, 1H); 7.59 (dd, 1H); 7.69 (t, 1H); 7.76 (s, 1H); 7.99 (d, 1H); 8.06 (d, 1H); 8.18 (s, 1H); 8.82 (s, 1H).

Example 35 is a non-limiting example of a suitable pro-drug for compounds of the invention, and is a suitable pro-drug of Example 1.

Example 36

[(5S)-3-(5-{2-fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl 6-[(methoxycarbonyl)(methyl)amino]hexanoate

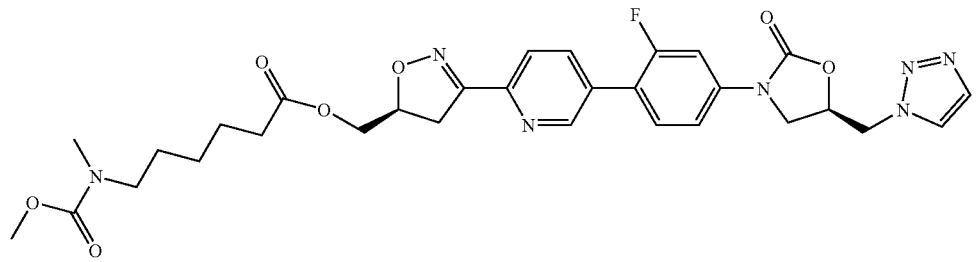

N-methyl-caprolactam (15 g, 118 mmol) was combined with barium hydroxide (10.1 g, 72 mmol) and water (150 ml). The suspension was warmed to 110° C. for 18 hours then cooled over an ice bath. Gaseous carbon dioxide was bubbled through the solution for 20 minutes. The suspension was filtered through a celite pad and the filtrate was concentrated to dryness. The residue was triturated with acetonitrile, collected, rinsed with ether and dried in vacuo to yield 6-(methylamino)hexanoic acid as a white solid (10.7 g). 6-(Methylamino)hexanoic acid (5 g, 34.5 mmol), and potassium carbonate (18 g, 130 mmol) were suspended in water (50 ml) and dioxane (25 ml) then cooled to 0° C. Methyl chloroformate (13 ml, 168 mmol) was added over 1 minute, then the mixture was stirred and allowed to warm slowly to room temperature for 16 hours. Conc. HCl (20 ml) was added then the mixture was diluted with water and extracted with ethyl acetate. The organic layer was dried over magnesium sulfate, evaporated and dried in vacuo to give 6-[(methoxycarbonyl)(methyl)amino]hexanoic acid as a thick clear oil (5.7 g).

The carbamate prepared as above (0.37 g, 1.82 mmol), (5R)-3-(3-fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 0.2 g, 0.46 mmol), 4-dimethylaminopyridine (0.01 g, 0.08 mmol), and 1-[3-(dimethylamino)propyl]-3-ethylcarbodiimide hydrochloride (0.19 g, 0.99 mmol) were combined in DMF (2 ml). The suspension was allowed to stir for 3.5 hours at room temperature resulting in a clear solution. The mixture was then diluted with ethyl acetate, washed with water, and dried over magnesium sulfate. The residue obtained upon filtration and evaporation was purified via chromatography (silica gel, 0.5 to 10% methanol in dichloromethane). Evaporation of the product containing fractions and trituration of the resulting solid with diethyl ether yielded the title compound as an off-white powder (0.225 g), melting point: 103° C.

MS (electrospray): 624 (MH+) for $C_{30}H_{34}FN_7O_7$ $^1$H-NMR (300 MHz, DMSO-d) δ: 1.16 (p, 2H); 1.36 (p, 2H); 1.48 (p, 2H); 2.29 (t, 2H); 2.74 (s, 3H); 3.10 (t, 2H); 3.29 (dd, 1H); 3.53 (s, 3H); 3.58 (dd, 1H); 3.96 (dd, 1H); 4.16 (dd, 1H); 4.26 (dd, 1H); 4.30 (t, 1H); 4.86 (d, 2H); 5.00 (m, 1H); 5.18 (m, 1H); 7.42 (dd, 1H); 7.59 (dd, 1H); 7.68 (t, 1H); 7.76 (s, 1H); 8.00 (d, 1H); 8.06 (d, 1H); 8.18 (s, 1H); 8.82 (s, 1H).

Example 36 is a non-limiting example of a suitable pro-drug for compounds of the invention, and is a suitable pro-drug of Example 1.

Example 37

[(5S)-3-(5-{2-fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl 5-(methylamino)pentanoate

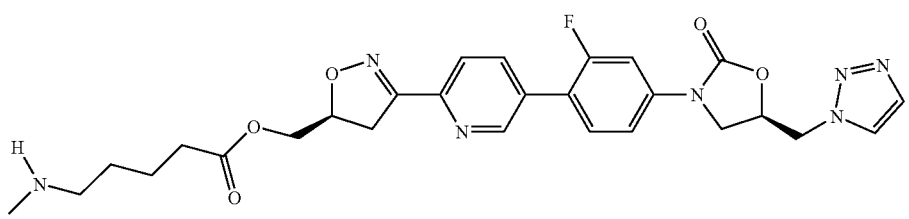

[(5S)-3-(5-{2-fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl 5-[(tert-butoxycarbonyl)(methyl)amino]pentanoate (Example 34: 0.5 g, 0.77 mmol) was combined with acetic acid (15 ml) and hydrochloric acid (4M solution in dioxane, 1 ml, 4 mmol). The suspension was warmed for 2 minutes at approximately 80° C. to dissolve most of the suspended material. The mixture was stirred at room temperature for an additional 15 minutes then concentrated under reduced pressure. The residual solids were dissolved in water (40 ml) then extracted twice with ethyl acetate (20 ml). Evaporation of the aqueous layer followed by drying under reduced pressure gave a solid that was dissolved in methanol (1 ml) and precipitated by the addition of diethyl ether (10 ml). The solution was decanted off and the precipitation was repeated. The resulting sticky oil was dried in vacuo at 50° C. to give the hydrochloride salt of the title compound as a hygroscopic solid (0.46 g), melting point: 184° C.

MS (electrospray): 552 (MH$^+$) for $C_{27}H_{30}FN_7O_5$ $^1$H-NMR (300 MHz DMSO-d$_6$) δ: 1.55 (bm, 4H); 2.36 (t, 2H); 2.49 (s, 3H); 2.82 (m, 2H); 3.31 (dd, 1H); 3.60 (dd, 1H); 3.96 (dd, 1H); 4.16 (dd, 1H); 4.27 (dd, 1H); 4.31 (d, 1H); 4.86 (d, 2H); 5.01 (m, 1H); 5.18 (m, 1H); 7.42 (dd, 1H); 7.59 (dd, 1H); 7.69 (t, 1H); 7.76 (s, 1H); 8.00 (d, 1H); 8.07 (d, 1H); 8.18 (s, 1H); 8.54 (bs, 2H); 8.83 (s, 1H).

Example 37 is a non-limiting example of a suitable pro-drug for compounds of the invention, and is a suitable pro-drug of Example 1.

Example 38

[(5S)-3-(5-{2-fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl 5-[(N,N-dimethylglycyl)(methyl)amino]pentanoate hydroisoxazol-5-yl]methyl 5-(methylamino)pentanoate (Example 37: 134 mg, 0.23 mMol), N,N-dimethylglycine (140 mg, 1.36 mMol), 1,3-diisopropylcarbodiimide (121 mg, 0.96 mMol), and 4-dimethylaminopyridine (5 mg, 0.04 mMol) were suspended in 2 ml of DMF at room temperature. The mixture was stirred one day, diluted with ethyl acetate, washed with saturated aqueous sodium bicarbonate, dried over sodium sulfate and evaporated. The residue was purified by chromatography (silica gel; elution with 1 to 10% methanol in dichloromethane) to give the title compound as the free base. The sample was dissolved in methylene chloride (0.5 ml), treated with HCl (4M solution in dioxane, 0.05 ml) and diluted with diethyl ether (10 ml). The suspension was sonicated and triturated, the solution was decanted from the solids which were resuspended in diethyl ether followed by further sonication then filtration. The solid was dried in vacuo to yield the hydrochloride salt of the title compound as a light yellow solid (95 mg), melting point: 133° C.

MS (electrospray): 673 (MH$^+$) for $C_{31}H_{37}FN_8O_6$ $^1$H-NMR (300 MHz, DMSO-d$_6$) δ: 1.42–1.53 (bm, 4H); 2.36 (m, 2H); 2.78 (s, 6H) ; 2.85 (s, 3H); 3.27–3.36 (m, 3H); 3.60 (dd, 1H); 3.96 (dd, 1H); 4.13–4.32 (m, 5H); 4.86 (d, 2H); 5.00 (m, 1H); 5.19 (m, 1H); 7.42 (dd, 1H); 7.59 (dd, 1H); 7.69 (t, 1H); 7.77 (s, 1H); 8.00 (d, 1H). Compound 38 is a non-limiting example of a suitable pro-drug for compounds of the invention, and is a suitable pro-drug of Example 1.

Example 39

(5R)-3-{3-Fluoro-4-[6-((5S)-5-{[(2-methoxyethoxy)methoxy]methyl}-4,5-dihydroisoxazol-3-yl)pyridin-3-yl]phenyl}-5-(1H-1,2,3-triazol-1-ylmethyl)-1,3-oxazolidin-2-one

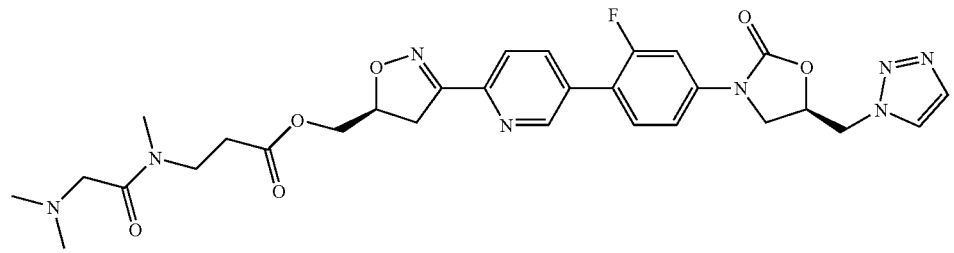

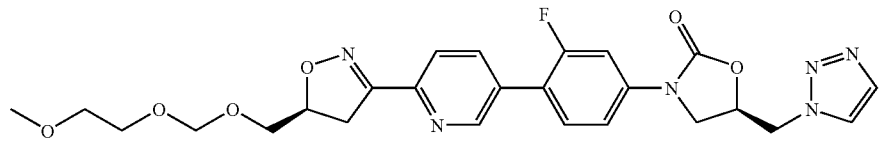

[(5S)-3-(5-{2-fluoro-4[(5R)-2-oxo-5-(1H-1,2,3-triazol-1-ylmethyl)-1,3-oxazolidin-3-yl]phenyl}pyridin-2-yl)-4,5-di- (5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 250 mg, 0.57 mmol), diisopropyl ethyl amine (238 μL, 1.37 mmol) and 2-methoxyethoxymethyl chloride (MEMCl) (78 μL, 0.68 mmol) were mixed in dry DMF (5 mL) and stirred at room temperature overnight. More diisopropyl ethylamine (250 μL, 1.44 mmol) and MEMCl (100 μL, 0.88 mmol) were added and it was stirred for another 6 hours. Again MEMCl (90 μL, 0.79 mmol) was added and it was stirred overnight. The solvent was evaporated under reduced pressure. Chromatography on silica gel with acetone/hexanes 3:1 and precipitation from dichloromethane/hexanes gave the product as off-white solid (261 mg).

MS (ESP): 527.57 (MH$^+$) for $C_{25}H_{27}FN_6O_6$ $^1$H-NMR 300 MHz (DMSO-d$_6$) δ: 3.23 (s, 3H); 3.26–3.70 (m, 8H); 3.96 (dd, 1H); 4.29 (dd, 1H); 4.66 (s, 2H); 4.86 (d, 2H); 4.93 (m, 1H); 5.18 (m, 1H); 7.41 (dd, 1H); 7.58 (dd, 1H); 7.68 (dd, 1H); 7.77 (s, 1H); 7.97–8.07 (m, 2H); 8.18 (s, 1H); 8.81 (s, 1H).

Example 39 is a non-limiting example of a suitable pro-drug for compounds of the invention, and is a suitable pro-drug of Example 1.

Example 40

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl β-D-glucopyranoside Intermediate 20: [(5S)-3-(5-Bromopyridin-2-yl)-4,5-dihydroisoxazol-5-yl]methyl β-D-glucopyranoside

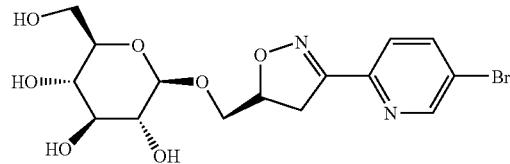

To a solution of [(5S)-3-(5-bromopyridin-2-yl)-4,5-dihydroisoxazol-5-yl]methanol (Intermediate 11, 0.369 g, 1.43 mmol) and 2,3,4,6-tetra-O-acetyl-1-O-(2,2,2-trichloroethanimidoyl)-α-D-glucopyranose (R. R. Schmidt and J. Michel, Angew. Chem. Int. Ed. Engl. 19 (1980), 731–732) in dry dichloromethane (20 mL) over molecular sieves (perled, 4 Å) was added dropwise at −20° C. a solution of trimethylsilyl trifluoromethanesulfonate in dichloromethane (0.02 M, 10 mL). The reaction mixture was allowed to reach room temperature over 2 hours, additional catalyst solution (5 mL) was added and it was left overnight at room temperature. The reaction was quenched by addition of triethylamine (3 drops), filtered and solvent was removed under reduced pressure. Chromatography on silica gel with hexanes/acetone 2:1 gave crude [(5S)-3-(5-bromopyridin-2-yl)-4,5-dihydroisoxazol-5-yl]methyl 2,3,4,6-tetra-O-acetyl-β-D-

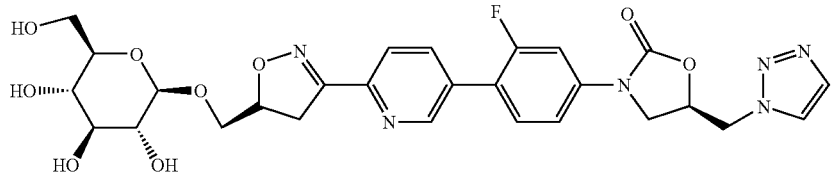

[(5S)-3-(5-Bromopyridin-2-yl)-4,5-dihydroisoxazol-5-yl]methyl β-D-glucopyranoside (Intermediate 20, 0.150 g, 0.36 mmol), (5R)-3-[3-fluoro-4-(4,4,5,5-tetramethyl-1,3,2-dioxaborolan-2-yl)phenyl]-5-(1H-1,2,3-triazol-1-ylmethyl)-1,3-oxazolidin-2-one (Intermediate 7, 0.153 g, 0.39 mmol), sodium carbonate (0.152 g, 1.43 mmol), and tetrakis(triphenylphosphino)palladium(0) (0.041 g, 0.036 mmol) were mixed in DMF/water (10:1, 5 mL) under nitrogen and heated at 70° C. bath temperature for 4 hours. The solvent was evaporated under reduced pressure. Chromatography on silica gel with dichloromethane/methanol 5:1 followed by crystallization from ethanol gave the product as colourless solid (83 mg). MS (ESP): 601.06 (MH$^+$) for $C_{27}H_{29}FN_6O_9$ $^1$H-NMR 300 MHz (MeOD-d$_4$) δ: 3.17–3.60 (m, 7H); 3.75–3.90 (m, 2H); 4.00–4.10 (m, 2H); 4.28–4.39 (m, 2H); 4.85–4.95 (m, 2H); 5.03 (m, 1H); 5.19 (m, 1H); 7.35 (dd, 1H); 7.53–7.60 (m, 2H); 7.76 (s, 1H); 8.00 (m, 2H); 8.09 (s, 1H); 8.74 (s, 1H).

Example 40 is a non-limiting example of a suitable pro-drug for compounds of the invention, and is a suitable pro-drug of Example 1.

glucopyranoside, as a mixture with intermediate 11. To a solution of this mixture in dry methanol (5 mL) was added potassium carbonate (20 mg) and it was vigorously stirred for 4 hours at room temperature. The reaction mixture was neutralized over Amberlite CG-50-II (H$^+$-form), filtered and solvent was removed under reduced pressure. Chromatography on silica gel with dichloromethane/methanol 8:1 gave the product as a colourless solid (157 mg).

MS (ESP): 419/421 (MH$^+$) for $C_{15}H_{19}BrN_2O_7$ $^1$H-NMR 300 MHz (DMSO-d+D$_2$O) δ: 2.90–3.16 (m, 4H); 3.25 (dd, 1H); 3.37–3.48 (m, 2H); 3.59–3.65 (m, 2H); 3.89 (dd, 1H); 4.18 (d, 1H, J$_{H1,H2}$ 7.7 Hz, H-1); 4.92 (m, 1H); 7.82 (d, 1H); 8.08 (dd, 1H); 8.71 (brs, 1H).

Example 41

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl N-methylglycinate

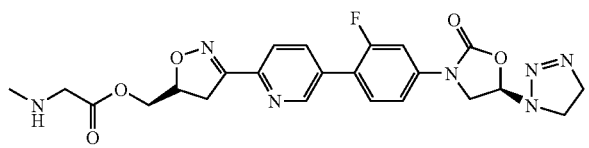

(5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 200 mg, 0.46 mmol), diisopropyl ethylamine (122 mg, 0.94 mmol), O-(7-azabenzotriazole-1-yl-N,N,N',N'-tetramethyluronium hexafluorophosphate (HATU) (188 mg, 0.49 mmol), 1-hydroxybenzotriazole (HOBT) (64 mg, 0.47 mmol) and N-(tert-butoxycarbonyl)glycine (98 mg, 0.52 mmol) were mixed in dry DMF (4 mL) and stirred at room temperature overnight. More HATU (94 mg, 0.25 mmol) was added and it was stirred for another 24 hours. Ethyl acetate (10 mL) was added, it was washed with water (2 times 5 mL) and dried over magnesium sulfate. The solvent was evaporated under reduced pressure. Chromatography on silica gel with 3% methanol in dichloromethane gave the BOC-protected intermediate as colourless solid; this solid was dissolved in dry 1,4-dioxane (2 mL), HCl in dioxane was added (4M, 4 mL), and the mixture was stirred at room temperature for 10 minutes. The resulting precipitate was collected by filtration, washed with dry diethyl ether, and dried under reduced pressure at 60° C. to give the HCl salt of the product as a colourless solid (173 mg).

MS (ESP): 510.54 (MH$^+$) for $C_{24}H_{24}FN_7O_5$ $^1$H-NMR 300 MHz (DMSO-d$_6$) δ: 2.60 (s, 3H); 3.35 (dd, 1H); 3.60 (dd, 1H); 3.95 (m, 3H); 4.29 (dd, 2H); 4.40 (m, 1H); 4.86 (d, 2H); 5.05 (m, 1H); 5.18 (m, 1H); 7.41 (dd, 1H); 7.60 (dd, 1H); 7.68 (dd, 1H); 7.77 (s, 1H); 7.97–8.07 (m, 2H); 8.18 (s, 1H); 8.81 (s, 1H); 9.21 (brs, 2H). Example 41 is a non-limiting example of a suitable pro-drug for compounds of the invention, and is a suitable pro-drug of Example 1.

Example 42

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl L-alaninate Preparation followed the procedure described for Example 41, except, for the amino acid building block N-(tert-butoxycarbonyl)-L-alanine (98 mg, 0.52 mmol) was used. The HCl salt of the product was obtained as colourless solid (175 mg).

MS (ESP): 510.58 (MH$^+$) for $C_{24}H_2N_7O_5$ $^1$H-NMR 300 MHz (DMSO-d$_6$) δ: 1.35 (d, 3H); 2.70 (d, 2H); 3.35 (dd, 1H); 3.65 (dd, 1H); 3.95 (m, 1H); 4.29 (dd, 1H); 4.40 (m, 1H); 4.86 (d, 2H); 5.05 (m, 1H); 5.18 (m, 1H); 7.41 (dd, 1H); 7.60 (dd, 1H); 7.68 (dd, 1H); 7.75 (s, 1H); 7.97–8.07 (m, 2H); 8.18 (s, 1H); 8.45 (brs, 2H); 8.85 (s, 1H). Example 42 is a non-limiting example of a suitable prodrug for compounds of the invention, and is a suitable pro-drug of Example 1.

Example 43

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl L-valinate

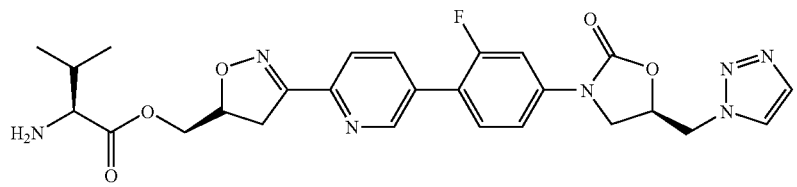

(5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 200 mg, 0.46 mmol) was reacted with N-(tert-butoxycarbonyl)-L-valine (113 mg, 0.52 mmol) following the procedure described under Example 41, except, instead of HATU/HOBt 1-(3-dimethylaminopropyl)-3-ethylcarbodiimide hydrochloride (EDC) (175 mg, 0.91 mmol) was used, and 4-dimethylaminopyridine (DMAP) (14 mg, 0.11 mmol) was used instead of diisopropyl ethylamine. The HCl salt of the product was obtained as a colourless solid (200 mg).

MS (ESP): 538.56 (MH$^+$) for $C_{26}H_{28}FN_7O_5$ $^1$H-NMR 300 MHz (DMSO-d$_6$) δ: 0.91 (2xd, 6H); 2.12 (m, 1H); 3.35 (dd, 1H); 3.60 (dd, 1H); 3.95 (m, 2H); 4.29 (dd, 2H); 4.40 (m, 1H); 4.86 (d, 2H); 5.05 (m, 1H); 5.18 (m, 1H); 7.41 (dd, 1H); 7.60 (dd, 1H); 7.68 (dd, 1H); 7.77 (s, 1H); 7.97–8.07 (m, 2H); 8.18 (s, 1H); 8.61 (brs, 1H); 8.81 (s, 1H). Example 43 is a non-limiting example of a suitable pro-drug for compounds of the invention, and is a suitable pro-drug of Example 1.

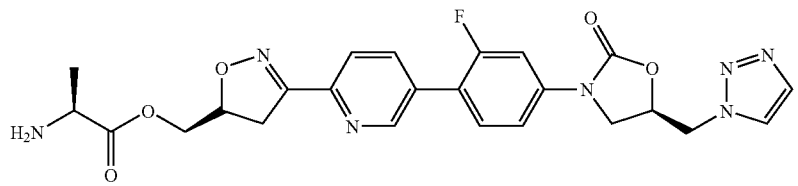

Example 44

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl L-leucinate

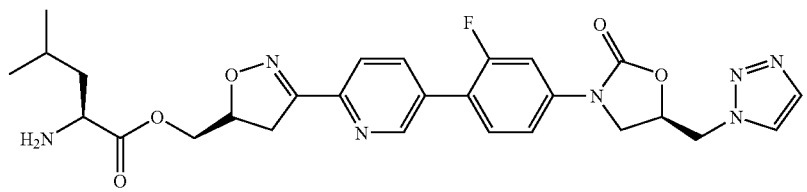

The preparation followed the procedure described for Example 43, except, as amino acid building block N-(tert-butoxycarbonyl)-L-leucine (208 mg, 0.9 mmol) was used. The HCl salt of the product was obtained as a colourless solid (161 mg).

MS (ESP): 552.60 (MH$^+$) for $C_{27}H_{30}FN_7O_5$ $^1$H-NMR 300 MHz (DMSO-d$_6$) δ: 0.71 (2xd, 6H); 1.5 (dd, 2H); 1.65 (m, 1H); 3.35 (dd, 1H); 3.60 (m, 1H); 3.95 (m, 2H); 4.31 (m, 3H); 4.86 (d, 2H); 5.08 (m, 1H); 5.18 (m, 1H); 7.41 (dd, 1H); 7.60 (dd, 1H); 7.68 (dd, 1H); 7.77 (s, 1H); 7.97–8.07 (m, 2H); 8.18 (s, 1H); 8.51 (brs, 2H); 8.81 (s, 1H). Example 44 is a non-limiting example of a suitable pro-drug for compounds of the invention, and is a suitable pro-drug of Example 1.

Example 45

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl glycinate

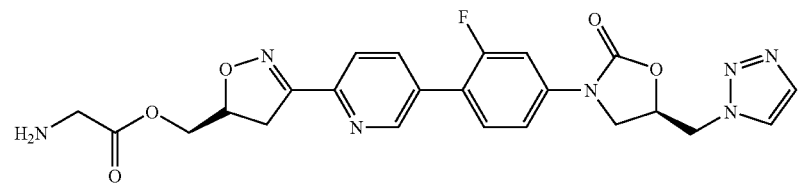

The preparation followed the procedure described for Example 43, except, as amino acid building block N-(tert-butoxycarbonyl)-glycine (158 mg, 0.9 mmol) was used. The HCl salt of the product was obtained as a colourless solid (140 mg).

MS (ESP): 496.52 (MH$^+$) for $C_{23}H_{22}FN_7O_5$ $^1$H-NMR 300 MHz (DMSO-d$_6$) δ: 3.35 (dd, 1H); 3.60 (m, 1H); 3.95 (m, 3H); 4.31 (m, 3H); 4.86 (d, 2H); 5.08 (m, 1H); 5.18 (m, 1H); 7.41 (dd, 1H); 7.60 (dd, 1H); 7.68 (dd, 1H); 7.77 (s, 1H); 7.97–8.07 (m, 2H); 8.18 (s, 1H); 8.31 (brs, 2H); 8.81 (s, 1H). Example 45 is a non-limiting example of a suitable pro-drug for compounds of the invention, and is a suitable pro-drug of Example 1.

Example 46

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl L-isoleucinate

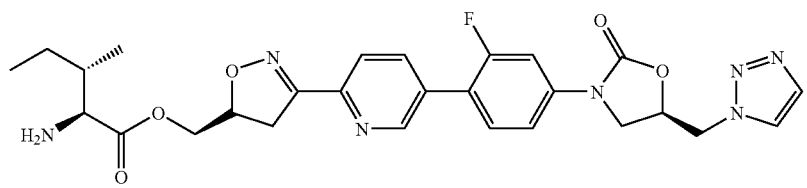

(5R)-3-(3-Fluoro-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 2000 mg, 4.6 mmol), N-(tert-butoxycarbonyl)-L-isoleucine (2.1 g, 9.13 mmol), EDC (1.84 g, 9.13 mmol) and DMAP (150 mg, 1.23 mmol) were reacted as described under Example 43 in dry DMF (10 mL). The HCl salt of the product was obtained as an off-white solid (2.0 g).

MS (ESP): 552.17 (MH$^+$) for $C_{27}H_{30}FN_7O_5$ $^1$H-NMR 300 MHz (DMSO-d$_6$) δ: 0.71 (t, 3H); 0.87 (d, 3H); 1.20 (m, 1H); 1.40 (m, 1H); 1.85 (m, 1H); 3.35 (dd, 1H); 3.65 (m, 1H); 3.95 (m, 2H); 4.31 (m, 3H); 4.86 (d, 2H); 5.08 (m, 1H); 5.18 (m, 1H); 7.41 (dd, 1H); 7.60 (dd, 1H); 7.68 (t, 1H); 7.77 (s, 1H); 7.97–8.07 (m, 2H); 8.18 (s, 1H);

8.55 (br, 2H); 8.81 (s, 1H). Example 46 is a non-limiting example of a suitable pro-drug for compounds of the invention, and is a suitable pro-drug of Example 1.

Example 47

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl L-glutaminate The preparation followed the procedure described for Example 43, except, as amino acid building block N-(tert-butoxycarbonyl)-L-glutamine (222 mg, 0.9 mmol) was used. The HCl salt of the product was obtained as a colourless solid (200 mg).

MS (ESP): 496.52 (MH$^+$) for $C_{26}H_{27}FN_8O_6$ $^1$H-NMR 300 MHz (DMSO-$d_6$) δ: 2.00 (m, 2H); 2.26 (m, 2H); 3.40 (dd, 1H); 3.60 (m, 1H); 3.95 (m, 2H); 4.31 (m, 3H); 4.86 (d, 2H); 5.08 (m, 1H); 5.18 (m, 1H); 6.98 (brs, 1H); 7.41 (dd, 1H); 7.60 (dd, 1H); 7.68 (dd, 1H); 7.77 (s, 1H); 7.97–8.07 (m, 2H); 8.18 (s, 1H); 8.71 (brs, 2H); 8.81 (s, 1H). Example 47 is a non-limiting example of a suitable pro-drug for compounds of the invention, and is a suitable pro-drug of Example 1.

The preparation followed the procedure described for Example 43, except, as amino acid building block N-(tert-butoxycarbonyl)-L-aspartic acid-4-tert-butyl ester, dicyclohexylammonium salt (423 mg, 0.9 mmol) was used. The crude HCl salt of the product was further purified by reverse phase HPLC with 5%–95% acetonitrile in water to give the product as a colourless solid (98 mg).

MS (ESP): 552.57 (M–H$^-$) for $C_{25}H_{24}FN_7O_7$

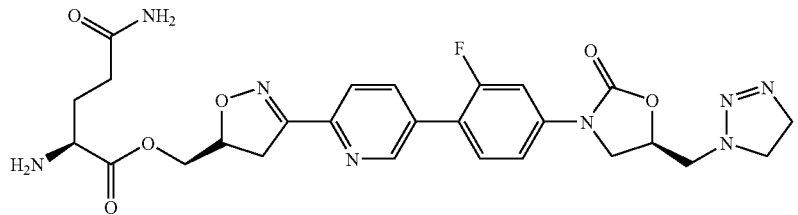

$^1$H-NMR 300 MH (DMSO-$d_6$) δ: 2.82 (dd, 2H); 3.35 (dd, 1H); 3.60 (m, 1H); 3.95 (m, 1H); 4.31 (m, 4H); 4.86 (d, 2H); 5.08 (m, 1H); 5.18 (m, 1H); 7.41 (dd, 1H); 7.60 (dd, 1H); 7.68 (dd, 1H); 7.77 (s, 1H); 7.97–8.07 (m, 2H); 8.18 (s, 1H); 8.41 (brs, 2H); 8.81 (s, 1H); 13.00 (brs, 1H). Example 48 is a non-limiting example of a suitable pro-drug for compounds of the invention, and is a suitable pro-drug of Example 1.

Example 48

1-[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl L-aspartate

Example 49

4-[(5S)-3-(5-{2-Fluoro-4-[(5R)-2-oxo-5-(1-1,2,3-triazol-1-ylmethyl)-1,3-oxazolidin-3-yl]phenyl}pyridin-2-yl)-4,5-dihydroisoxazol-5-yl]methyl L-aspartate

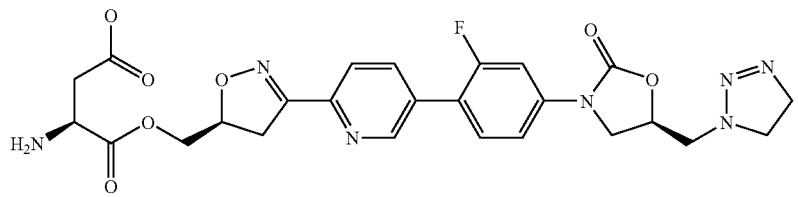

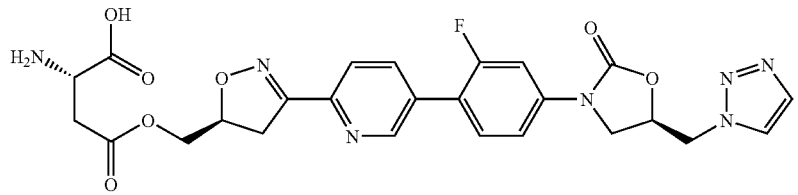

The preparation followed the procedure described for Example 43, except, as amino acid building block N-(tert-butoxycarbonyl)-L-aspartic acid-1-tert-butyl ester (266 mg, 0.9 mmol) was used. The crude HCl salt of the product was further purified by reverse phase HPLC with 5%~95% acetonitrile in water to give the product as a colourless solid (98 mg).

MS (ESP): 554.56 (MH$^+$) for $C_{25}H_{24}FN_7O_7$ $^1$H-NMR 300 MHz (DMSO-d$_6$) δ: 2.85 (m, 2H); 3.35 (m, 1H); 3.60 (m, 1H); 3.95 (m, 2H); 4.15–4.35 (m, 3H); 4.86 (d, 2M); 5.08 (m, 1H); 5.18 (m, 1H); 7.42 (dd, 1H); 7.60 (dd, 1H); 7.68 (dd, 1H); 7.76 (s, 1H); 7.97–8.07 (m, 2H); 8.18 (s, 1H); 8.82 (s, 1H). Example 49 is a non-limiting example of a suitable pro-drug for compounds of the invention, and is a suitable pro-drug of Example 1.

Example 50

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl L-lysinate (5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 375 mg, 0.86 mmol), EDC (345 mg, 1.28 mmol), DMAP (25 mg, 0.20 mmol) and N$^2$,N$^6$-bis(tert-butoxycarbonyl)-L-lysine (444 mg, 0.52 mmol) were mixed in dry DMF (6 mL) and reacted following the procedure described for Example 43. The bis HCl salt of the product was obtained as a colourless solid (400 mg).

MS (ESP): 567.48 (MH$^+$) for $C_{27}H_{31}FN_8O_5$ $^1$H-NMR 300 MHz (DMSO-d$_6$) δ: 1.45 (m, 4H); 1.76 (m, 2H); 2.70 (m, 2H); 3.35 (dd, 1H); 3.60 (dd, 1H); 4.0 (m, 2H); 4.29 (dd, 1H); 4.40 (d, 2H); 4.86 (d, 2H); 5.05 (m, 1H); 5.18 (m, 1H); 7.41 (dd, 1H); 7.60 (dd, 1H); 7.68 (dd, 1H); 7.77 (s, 1H); 7.90–8.10 (m, 4H); 8.18 (s, 1H); 8.55 (m, 2H); 8.81 (s, 1H).

Example 50 is a non-limiting example of a suitable pro-drug for compounds of the invention, and is a suitable pro-drug of Example 1.

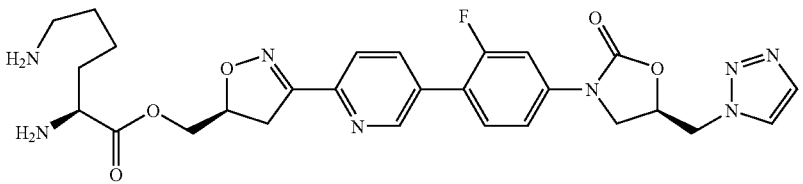

Example 51

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl L-Phenylalaninate

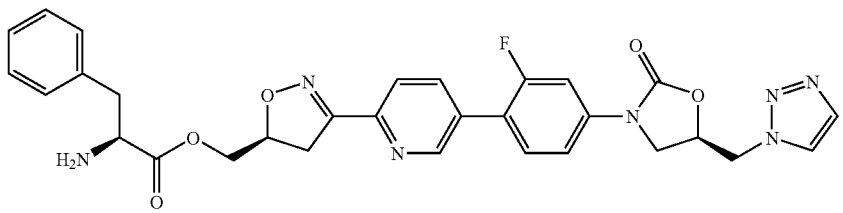

The preparation followed the procedure described for Example 43, except, as amino acid building block N-(tert-butoxycarbonyl)-L-phenylalanine (244 mg, 0.9 mmol) was used. The HCl salt of the product was obtained as a colourless solid (255 mg).

MS (ESP): 586.12 (MH$^+$) for $C_{30}H_{28}FN_7O_5$ $^1$H-NMR 300 MHz (DMSO-d$_6$) δ: 3.35 (dd, 1H); 3.45 (dd, 2H); 3.60 (dd, 1H); 4.0 (dd, 1H); 4.31 (m, 3H); 4.86 (d, 2H); 5.08 (m, 1H); 5.18 (m, 1H); 7.21 (m, 5H); 7.41 (dd, 1H); 7.60 (dd, 1H); 7.68 (dd, 1H); 7.77 (s, 1H); 7.97–8.07 (m, 2H); 8.18 (s, 1H); 8.51 (brs, 2H); 8.81 (s, 1H). Example 51 is a non-limiting example of a suitable pro-drug for compounds of the invention, and is a suitable pro-drug of Example 1.

Example 52

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl L-prolinate 1H); 4.0 (dd, 1H); 4.31 (m, 2H); 4.4 (m, 2H); 4.86 (d, 2H); 5.08 (m, 1H); 5.18 (m, 1H); 7.41 (dd, 1H); 7.60 (dd, 1H); 7.68 (dd, 1H); 7.77 (s, 1H); 7.97–8.07 (m, 2H); 8.18 (s, 1H); 8.81 (s, 1H); 9.05 (brs, 1H); 10.12 (brs, 1H). Example 52 is a non-limiting example of a suitable pro-drug for compounds of the invention, and is a suitable pro-drug of Example 1.

Example 53

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl {2-[(methoxycarbonyl)(methyl)amino]ethoxy}acetate

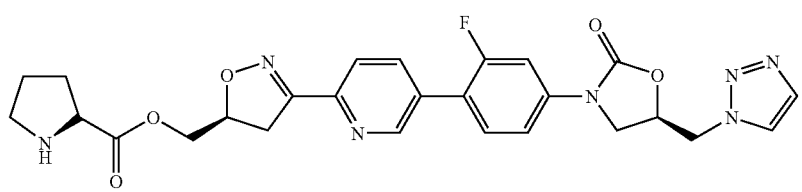

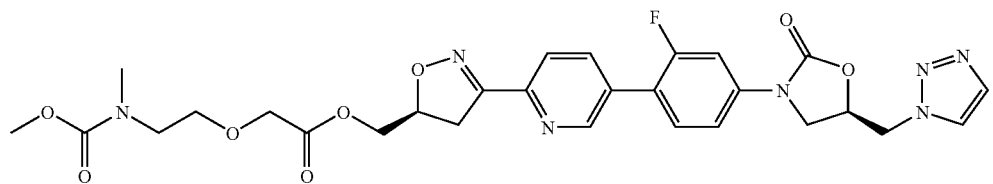

The preparation followed the procedure described for Example 43, except, as amino acid building block N-(tert-butoxycarbonyl)-L-proline (198 mg, 0.9 mmol) was used. The HCl salt of the product was obtained as a colourless solid (290 mg).

MS (ESP): 636.19 (MH$^+$) for $C_{26}H_{26}FN_7O_5$ $^1$H-NMR 300 MHz (DMSO-d$_6$)(HCl salt) δ: 1.95 (m, 3H); 2.16 (m, 1H); 3.18 (m, 2H); 3.35 (dd, 1H); 3.60 (dd, (5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 250 mg, 0.57 mmol), EDC (200 mg, 1.0 mmol), DMAP (20 mg, 0.16 mmol) and Intermediate 21 (100 mg, 0.52 mmol) were mixed in dry DMF (4 mL) and stirred at room temperature overnight. Ethyl acetate (10 ml) was added and the resulting mixture was washed with water and dried over magnesium sulfate. Chromatography on silica gel with 3% methanol in dichloromethane gave the product as a colourless solid (110 mg).

MS (ESP): 612.14 (MH⁺) for $C_{28}H_{30}FN_7O_8$

¹H-NMR 300 MHz (CDCl₃) δ: 2.95 (s, 3H); 3.35 (dd, 1H); 3.45 (m, 2H); 3.60–3.67 (m, 3H); 3.70 (s, 3H); 4.0 (dd, 1H); 4.12 (s, 2H); 4.25 (dd, 1H); 4.36 (m, 2H); 4.82 (d, 2H); 5.0~5.2 (m, 2H); 7.21 (dd, 1H); 7.41 (m, 2H); 7.75 (s, 1H); 7.79 (s, 1H); 7.87 (dd, 1H); 8.05 (dd, 1H); 8.78 (s, 1H). Example 53 is a non-limiting example of a suitable pro-drug for compounds of the invention, and is a suitable pro-drug of Example 1.

Intermediate 21: {2-[(Methoxycarbonyl)(methyl)amino]ethoxy}acetic acid

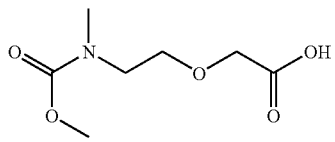

[2-(Methylamino)ethoxy]acetic acid (Bull. Soc. Chim.; 1956, 1210) (130 mg, 0.98 mmol) was mixed with triethylamine (0.56 mL, 4 mmol) in dry DMF (2 mL). Methylchloroformate (185 mg, 1.95 mmol) was added and the mixture was stirred at room temperature for 20 minutes, then quenched with water. Aqueous HCl (2M) was added to adjust the pH to ~2. Product was extracted with ethyl acetate, the organic phase was dried over magnesium sulfate and concentrated under reduced pressure to give the crude product as an oil (100 mg), which was used without further purification.

MS (ESP): 190.2 (M–H⁻) for $C_7H_{13}NO_5$

Example 54

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl[2-(methylamino)ethoxy]acetate mixed in dry DMF (4 mL) and stirred at room temperature overnight. Ethyl acetate (10 mL) was added, it was washed with water and dried over magnesium sulfate. Chromatography and cleavage of the BOC group were performed as described under Example 21 to give the HCl salt of the product as a colourless solid 200 mg).

MS (ESP): 554.05 (MH⁺) for $C_{26}H_{28}FN_7O_6$

¹H-NMR 300 MHz (CDCl₃) δ: 2.50 (s, 3H); 2.55 (t, 2H); 3.07 (m, 2H); 3.35 (dd, 1H); 3.55 (m, 2H); 3.95 (dd, 1H); 4.23 (s, 2H); 4.30 (m, 2H); 4.82 (d, 2H); 5.05 (m,1H); 5.20 (m, 1H); 7.45 (dd, 1H); 7.60 (dd,1H); 7.70 (dd, 1H); 7.77 (s, 1H); 7.95–8.10 (m, 2H); 8.20 (s, 1H); 8.85 (brs, 2H). Example 54 is a non-limiting example of suitable pro-drug for compounds of the invention, and is a suitable pro-drug of Example 1.

Intermediate 22: {2-[(tert-Butoxycarbonyl)(methyl)amino]ethoxy}acetic acid

[2-(methylamino)ethoxy]acetic acid (Bull. Soc. Chim.; 1956, 1210) (130 mg, 0.98 mmol) was mixed with triethylamine (0.56 mL, 4.0 mmol) and di-tert-butyl dicarbonate (647 mg, 3.0 mmol) were reacted in dry DMF (5 mL) like described for Intermediate 21 to give the crude product as an oil (229 mg), which was used without further purification.

MS (ESP): 232.22 (M–H⁻) for $C_{10}H_{19}NO_5$

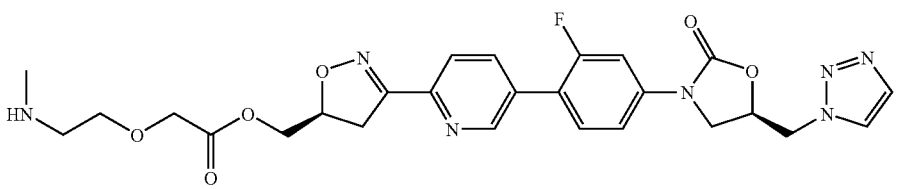

(5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 200 mg, 0.46 mmol), EDC (175 mg, 0.91 mmol), DMAP (14 mg, 0.11 mmol) and Intermediate 22 (229 mg, 0.98 mmol) were Example 55

[(5S)-3-(5-{2-Fluoro-4-[(5R)-2-oxo-5-(1H-1,2,3-triazol-1-ylmethyl)-1,3-oxazolidin-3-yl]phenyl}pyridin-2-yl)-4,5-dihydroisoxazol-5-yl]methyl N-methyl-L-isoleucinate

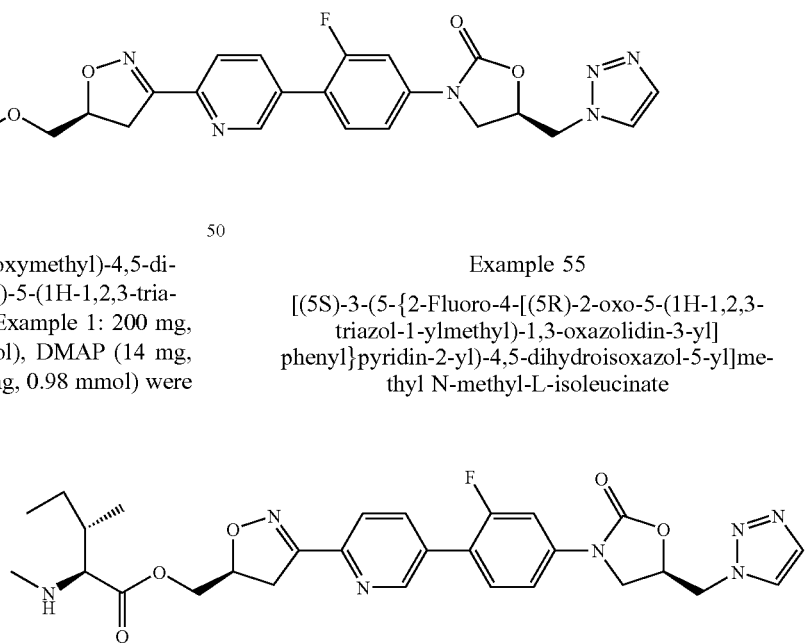

(5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one (Example 1: 250 mg, 0.57 mmol), EDC (230 mg, 1.14 mmol), DMAP (20 mg, 0.16 mmol) and N-(tert-butoxycarbonyl)-N-methyl-L-isoleucine (280 mg, 1.14 mmol) were mixed in dry DMF (2 mL) and reacted following the procedure described for Example 43. The HCl salt of the product was obtained as a colourless solid (150 mg).

MS (ESP): 566.45 (MH$^+$) for $C_{28}H_{32}FN_7O_5$ $^1$H-NMR 300 MHz (DMSO-d$_6$) δ: 0.71 (t, 3H); 0.87 (d, 3H); 1.20 (m, 1H); 1.40 (m, 1H); 1.85 (m, 1H); 2.57 (s, 3H); 3.35 (dd, 1H); 3.65 (m, 1H); 3.95 (m, 2H); 4.31 (m, 3H); 4.86 (d, 2H); 5.08 (m, 1H); 5.18 (m, 1H); 7.41 (dd, 1H); 7.60 (dd, 1H); 7.68 (dd, 1H); 7.77 (s, 1H); 7.97–8.07 (m, 2H); 8.18 (s, 1H); 8.81 (s, 1H); 9.20 (brs, 1H); 9.50 (brs, 1H). Example 55 is a non-limiting example of suitable pro-drug for compounds of the invention, and is a suitable pro-drug of Example 1.

The invention claimed is:

1. A compound of formula (I),

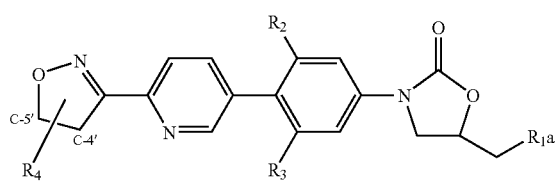

(I)

wherein:

$R_1a$ is —NH(C═W)$R_5$ or

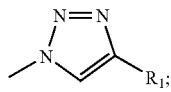

W is O or S;

$R_2$ and $R_3$ are independently selected from H, F, Cl, $CF_3$, OMe, SMe, Me and Et;

$R_1$ is selected from hydrogen, halogen, cyano, (1–4C) alkyl, cyano(1–4C)alkyl, halo(1–4C)alkyl, dihalo (1–4C)alkyl, trihalo(1–4C)alkyl, amino, (1–4C)alkylamino, di-(1–4C)alkylamino, (1–4C)alkylthio, (1–4C) alkoxy, (1–4C)alkoxy(1–4C)alkyl, (2–4C)alkenyloxy, (2–4C)alkenyl, (2–4C)alkynyl, (3–6C)cycloalkyl, (3–6C)cycloalkeny and (1-4C)alkoxycarbonyl;

and wherein at each occurrence of an $R_1$ substituent containing an alkyl, alkenyl, alkynyl, cycloalkyl or cycloalkenyl moiety each such moiety is optionally substituted on an available carbon atom with one, two, three or more substituents independently selected from F, Cl, Br, OH and CN;

$R_5$ is selected from hydrogen, (2–6C)alkyl (optionally substituted by 1, 2 or 3 substituents independently selected from methyl, chloro, bromo, fluoro, methoxy, methylthio, azido and cyano), methyl (optionally substituted by 1, 2 or 3 substituents independently selected from methyl, chloro, bromo, fluoro, methoxy, methylthio, hydroxy, benzyloxy, ethynyl, (1–4C)alkoxycarbonyl, azido and cyano), 5-halo-2-thienyl, —N($R_6$) ($R_7$), —O$R_6$, —S$R_6$, (2–4C)alkenyl, -(1–8C)alkylaryl, per-halo(1–8C)alkyl, —(CH$_2$)p(3–6C)cycloalkyl and —(CH$_2$)p(3–6C)cycloalkenyl wherein p is 0, 1 or 2;

$R_6$ and $R_7$ are independently selected from hydrogen, and (1–4C)alkyl (optionally substituted with one, two, three or more halogen atoms);

wherein $R_4$ is either a hydroxymethyl substituent on C-4' of the isoxazoline ring; or $R_4$ is a hydroxymethyl substituent on C-5' of the isoxazoline ring and the stereochemistry at C-5' of the isoxazoline ring and at C-5 of the oxazolidinone ring is selected, such that the compound of formula (I) is a single diastereomer;

or a pharmaceutically acceptable salt, solvate or pro-drug thereof.

2. The compound of claim 1, which is a compound of formula (IC:

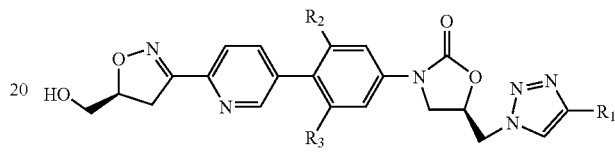

(IC)

wherein $R_2$ and $R_3$ are independently selected from hydrogen and fluorine;

$R_1$ is selected from hydrogen, halogen, cyano, (1–4C) alkyl, halo(1–4C)alkyl, dihalo(1–4C)alkyl and (2–4C) alkynyl.

3. The compound of claim 1, which is a compound of formula (ID):

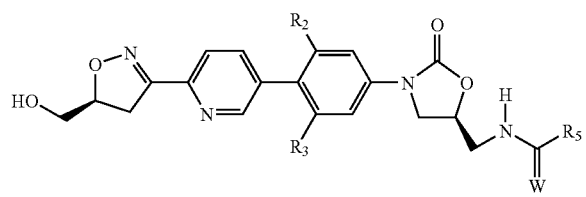

(ID)

wherein

W is O;

$R_2$ and $R_3$ are independently selected from hydrogen and fluorine;

$R_5$ is selected from methyl, ethyl, dichloromethyl and cyclopropyl.

4. The compound of claim 1, which is a compound of formula (IE):

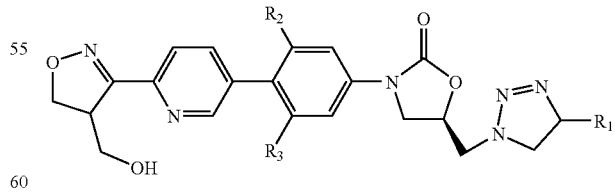

(IE)

wherein $R_2$ and $R_3$ are independently selected from hydrogen and fluorine;

$R_1$ is selected from hydrogen, halogen, cyano, (1–4C) alkyl, halo(1–4C)alkyl, dihalo(1–4C)alkyl and (2–4C) alkynyl.

5. The compound of claim 1, which is a compound of formula (IF):

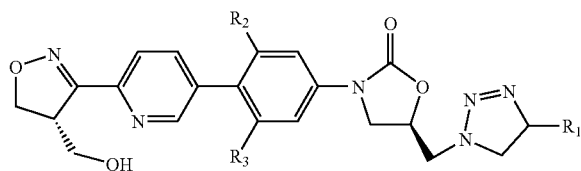

(IF)

wherein
 $R_2$ and $R_3$ are independently selected from hydrogen and fluorine;
 $R_1$ is selected from hydrogen, (1–4C)alkyl, halo(1–4C)alkyl and hydrogen, halogen, (1–4C)alkyl, halo(1–4C)alkyl, dihalo(1–4C)alkyl and (2–4C)alkynyl.

6. The compound of claim 1, which is a compound of formula (IG):

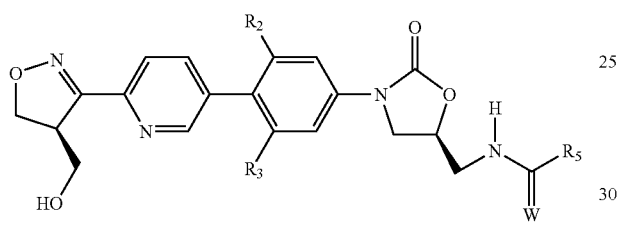

(IG)

wherein
 W is O;
 $R_2$ and $R_3$ are independently selected from hydrogen and fluorine;
 $R_5$ is selected from methyl, ethyl, dichloromethyl and cyclopropyl.

7. The compound of the claim 1, which is a compound of formula (IH):

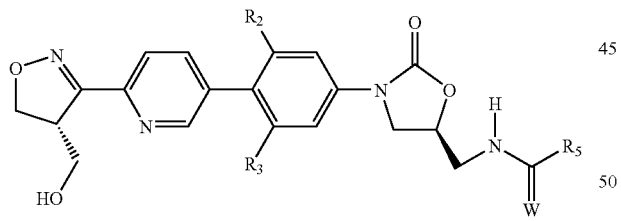

(IH)

wherein
 W is O;
 $R_2$ and $R_3$ are independently selected from hydrogen and fluorine;
 $R_5$ is selected from methyl, ethyl, dichloromethyl and cyclopropyl.

8. A compound which is (5R)-3-(3-Fluoro-4-{6-[(5S)-5-(hydroxymethyl)-4,5-dihydroisoxazol-3-yl]pyridin-3-yl}phenyl)-5-(1H-1,2,3-triazol-1-ylmethyl)-1,3-oxazolidin-2-one; or a pharmaceutically-acceptable salt, solvate, in-vivo hydrolysable ester, or pro-drug thereof.

9. The in-vivo hydrolysable ester of claim 1, which is an ester formed from an amino acid, or a pharmaceutically-acceptable salt thereof.

10. The in-vivo hydrolysable ester of claim 9, wherein the amino acid is selected from leucine, iso-leucine, N-methyl isoleucine, N-tert-butyl-isoleucine, lysine, glycine, N,N-dimethyl glycine, alanine, sarcosine, valine, phenylalanine and proline.

11. A method for producing an antibacterial effect in a warm blooded animal which comprises administering to said animal an effective amount of a compound of claim 1.

12. A pharmaceutical composition which comprises a compound of claim 1 and a pharmaceutically-acceptable diluent or carrier.

13. A process for the preparation of a compound of claim 1, which process comprises any one of processes (a) to (l):
 a) by modifying a substituent in, or introducing a substituent into another compound of the invention;
 b) by reaction of one part of a compound of formula (II) (wherein X is a leaving group useful in palladium [0]coupling) with one part of a compound IIa, again with a leaving group X, such that the pyridyl-phenyl bond replaces the phenyl-X and pyridyl-X bonds;

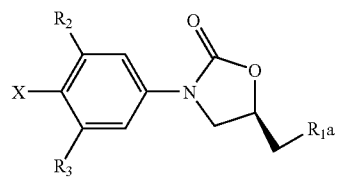

(II)

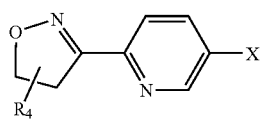

(IIa)

c) by reaction of a pyridyl-phenyl carbamate derivative (III) with an appropriately substituted oxidant to form an oxazolidinone ring;

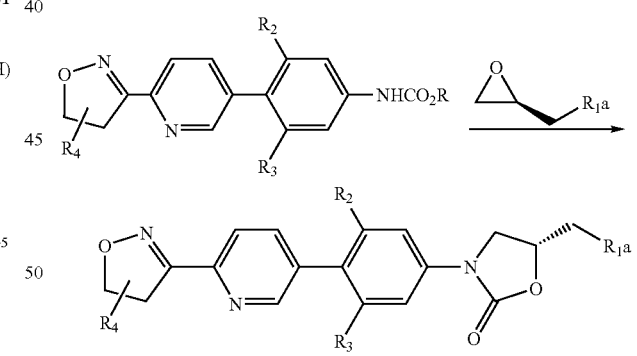

(d) by reaction of a compound of formula (IV):

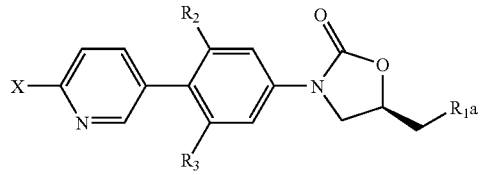

(IV)

where X is a replaceable substituent with a compound of the formula (V):

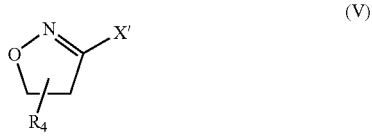

wherein X' is a replaceable substituent wherein the substituents X and X' are chosen to be complementary pairs of substituents known in the art to be suitable as complementary substrates for coupling reactions catalysed by transition metals such as palladium(0);

e) by reaction of a 3-pyridylphenylbiaryl aldehyde derivative (VI) to form an isoxazoline ring at the undeveloped heteroaryl position;

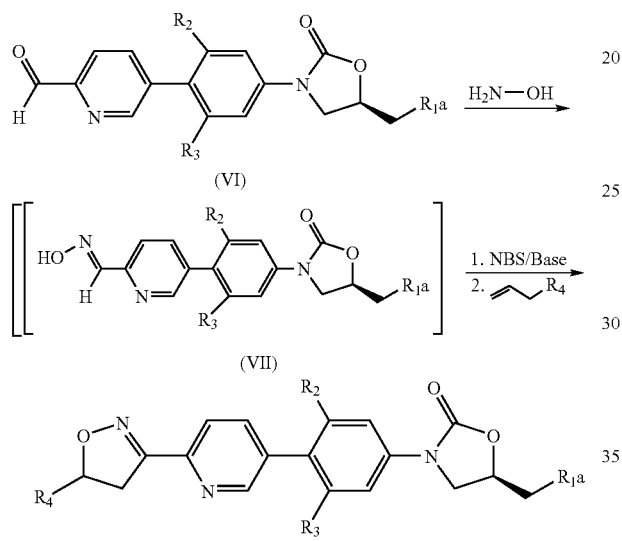

f) when $R_1a$ is an N-linked 1,2,3-triazole, by formation of the triazole ring from a suitably functionalised intermediate in which the isoxazole-pyridyl-phenyl ring system is already formed;

g) for $R_1a$ as a 1,2,3-triazole, by cycloaddition via the azide to acetylenes;

h) for $R_1a$ as 4-substituted 1,2,3-triazole, compounds of formula (I) may be made by reacting aminomethyloxazolidinones with 1,1-dihaloketone sulfonylhydrazones;

i) for $R_1a$ as 4-halogenated 1,2,3-triazoles, compounds of formula (I) by reacting azidomethyl oxazolidinones with halovinylsulfonyl chlorides;

j) for $R_1a$ as $NHCOCH_3$, compounds of formula (I) may be prepared by:

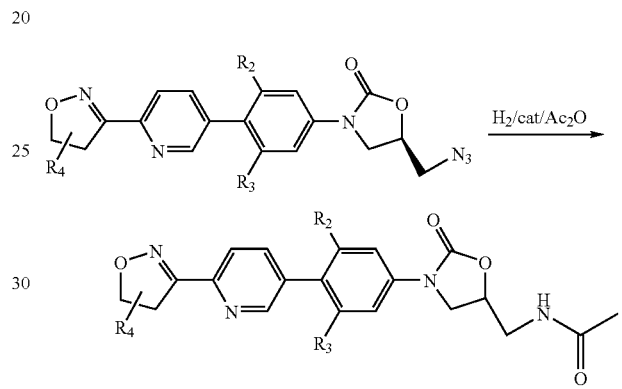

k) for $R_4$ on C'4, a suitably disubstituted olefin may be used where Y is a regioselective directing group in the cycloaddition which is subsequently removed in a final step as illustrated below:

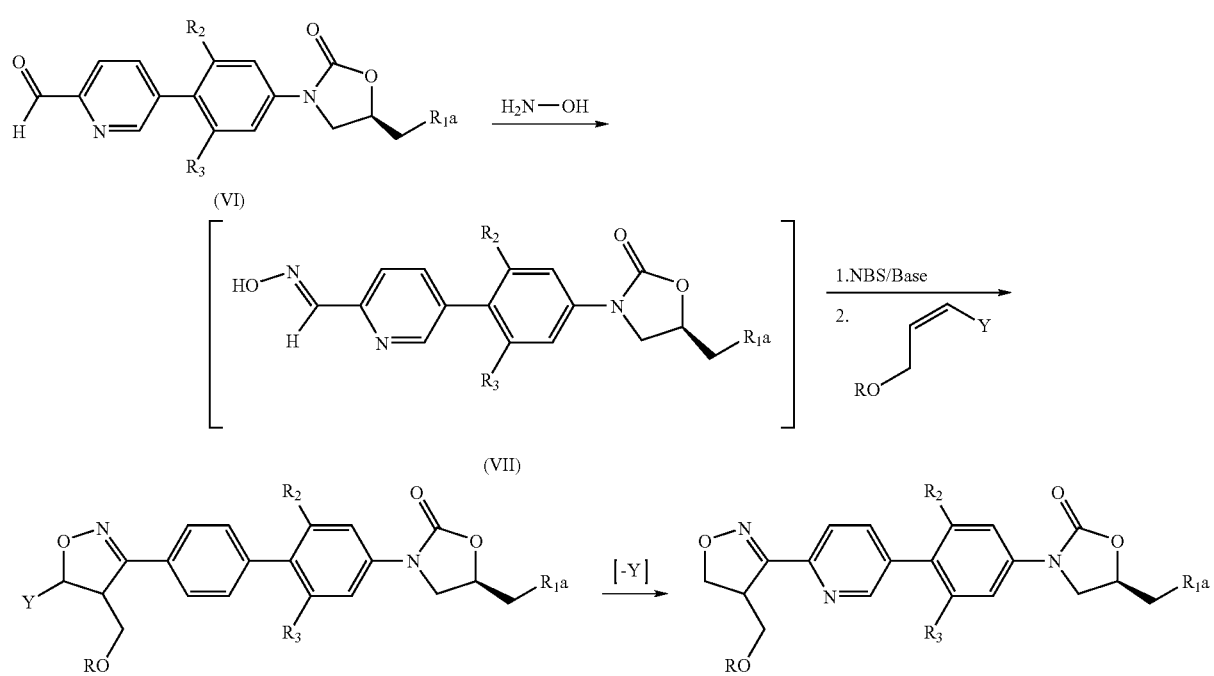

l) an alternative route to a preferred single hydroxyalkyl $R_4$ epimer at C4' or C5' is via enantioselective esterase hydrolysis of a racemic mixture of esters at that prochiral centre;

and thereafter if necessary:

i) removing any protecting groups;

ii) forming a pro-drug (for example an in-vivo hydrolysable ester); and/or iii) forming a pharmaceutically-acceptable salt.

14. A pharmaceutical composition which comprises a compound claim 1 co-formulated with an antibacterial agent which is active against gram-positive bacteria.

15. A pharmaceutical composition which comprises a compound of claim 1 co-formulated with an antibacterial agent which is active against gram-negative bacteria.

16. A pharmaceutical composition which comprises a compound of claim 1 together with an antibacterial agent which is active against gram-positive bacteria, for co-administration.

17. A pharmaceutical composition which comprises a compound of claim 1 together with an antibacterial agent which is active against gram-negative bacteria, for co-administration.

* * * * *